US006913889B2

(12) United States Patent
Gerbi et al.

(10) Patent No.: US 6,913,889 B2
(45) Date of Patent: Jul. 5, 2005

(54) METHODS TO SCREEN FOR ANTIBIOTIC AGENTS AND THEIR USE IN TREATMENT OF OPPORTUNISTIC INFECTIONS

(75) Inventors: Susan Gerbi, Seekonk, MA (US); Thilo Sascha Lange, Providence, RI (US); Anton Borovjagin, Providence, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 10/320,210

(22) Filed: Dec. 16, 2002

(65) Prior Publication Data

US 2003/0203378 A1 Oct. 30, 2003

Related U.S. Application Data

(63) Continuation of application No. PCT/US01/20520, filed on Jun. 28, 2001.
(60) Provisional application No. 60/215,572, filed on Jun. 30, 2000.

(51) Int. Cl.[7] .................................................. C12Q 1/68
(52) U.S. Cl. ......................................................... 435/6
(58) Field of Search .............................................. 435/6

(56) References Cited

PUBLICATIONS

Hartshorne and Toyofuku, Two 5' ETS Regions Implicated in Interactions with U3 snoRNA are Required for Small Subunit rRNA Maturation in *Trypanosoma brucei*, *Nucleic Acids Research*, vol. 27, No. 16, p. 3300–3309, 1999.

*Primary Examiner*—Mark Navarro
(74) *Attorney, Agent, or Firm*—Kathleen M. Williams; Palmer & Dodge, LLP

(57) ABSTRACT

The present invention provides novel targets in eukaryotic cells for antibiotic agents and methods for identification of antibiotic agents affecting such targets and the use of the identified antibiotic agents in treatment of opportunistic infections in eukaryotic hosts. The invention is based upon the identification of species specific 5' hinge and 3' hinge regions of U3 small nucleolar ribonucleic acid (snoRNA). The present invention discloses that the external transcribed spacer (ETS) of the ribosomal RNA precursor (pre-rRNA) comprises sequences that are complementary to the 5' and 3' hinge regions of U3 snoRNA. The invention further discloses that sequence substitutions of the 5' hinge or 3' hinge region of U3 snoRNA severely compromise or fully inhibit the cleavage events at sites 1 and 2 in rRNA processing necessary to form mature 18S rRNA which is a vital component of the small subunit of ribosomes of all eukaryotes.

27 Claims, 27 Drawing Sheets

```
                  30              40
5'-...UUUCUAUAGGU UGUA CCUG GUG AAAUG... -3'   (SEQ ID NO: 87)
                 ╱╲    ╱╲
                ╱  ╲  ╱  ╲
               'UA' 'UU'
          ┌──────────────────┐
          │  4 nt ins / loop I │
          └──────────────────┘

40         50
5'-...GUA CCUG GU GAAAUG UG CUCGAAA... -3'   (SEQ ID NO: 89)
              ╱╱         ╲╲
            'CC'         'CA'
          ┌──────────────┐
          │   sub / 2+2   │
          └──────────────┘

40         50
5'-...GUA CCUG GU GAAAUG UG CUCGAAA... -3'   (SEQ ID NO: 89)
              ╱╱         ╲╲
            'UA'         'AU'
          ┌──────────────┐
          │    no bulge   │
          └──────────────┘

40          50
5'-...GUACCUG,GUGAAAUGUG,CUCGAAA... -3'   (SEQ ID NO: 89)
              ╱╲          ╱╲
            'CC'         'CA'
          ┌──────────────┐
          │    ins / 2+2  │
          └──────────────┘

40         50
5'-...GUACCUG·GU,GAAAUG·UG,CUCGAAA... -3'   (SEQ ID NO: 89)
              ╲╱          ╲╱
          ┌──────────────┐
          │      Δ 2+2    │
          └──────────────┘

60          70
5'-... CUCGAAAGUGU CUGAACUCACAAA...-3'   (SEQ ID NO: 94)
                  ╲    ╱   hinge
                   ╲  ╱
          ┌──────────────────┐
          │  Δ 4 nt /Bottom   │
          └──────────────────┘
```

FIG. 2D-2

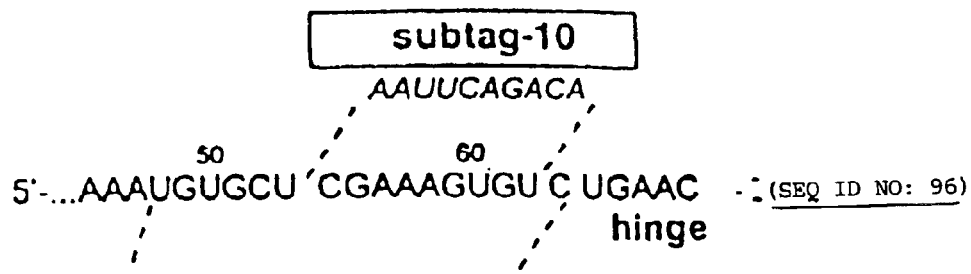
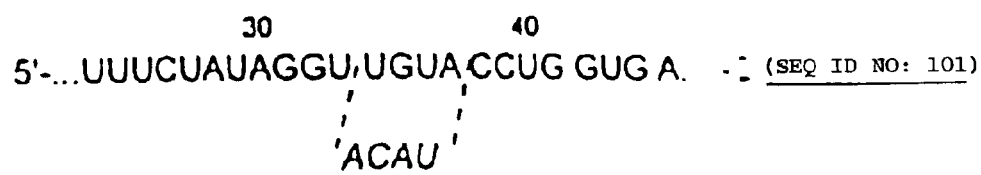
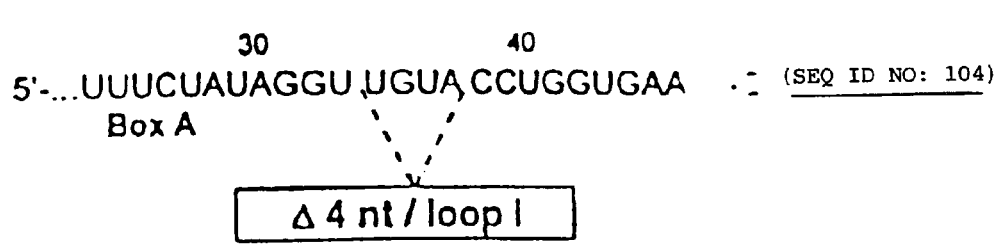
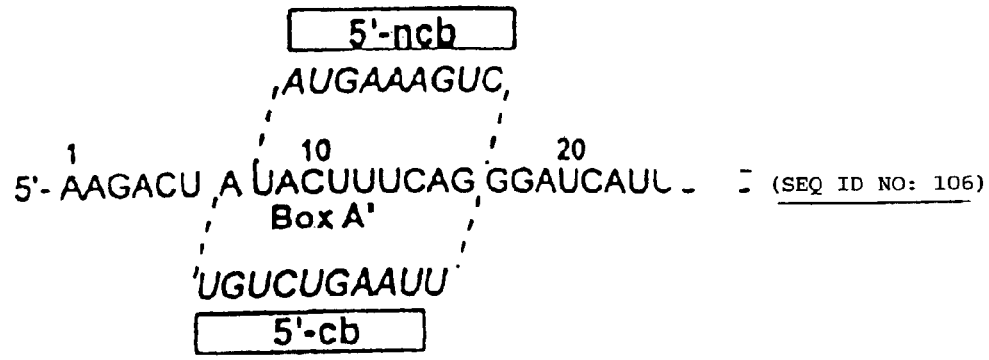
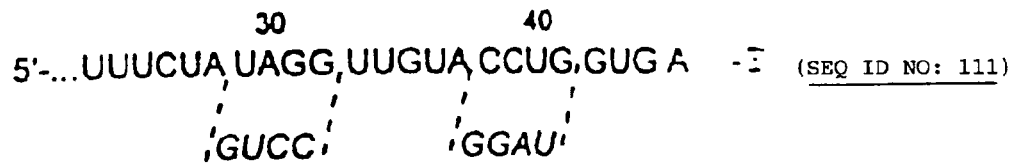
FIG. 2D-3

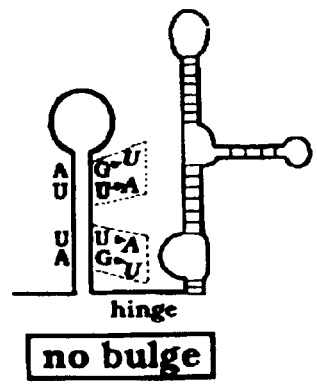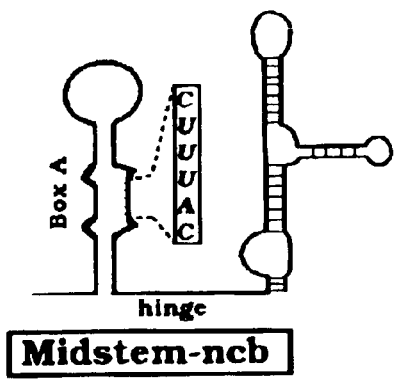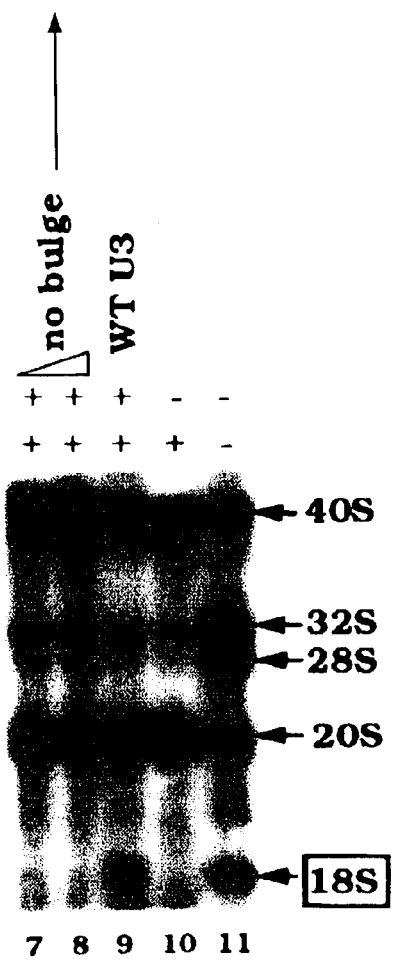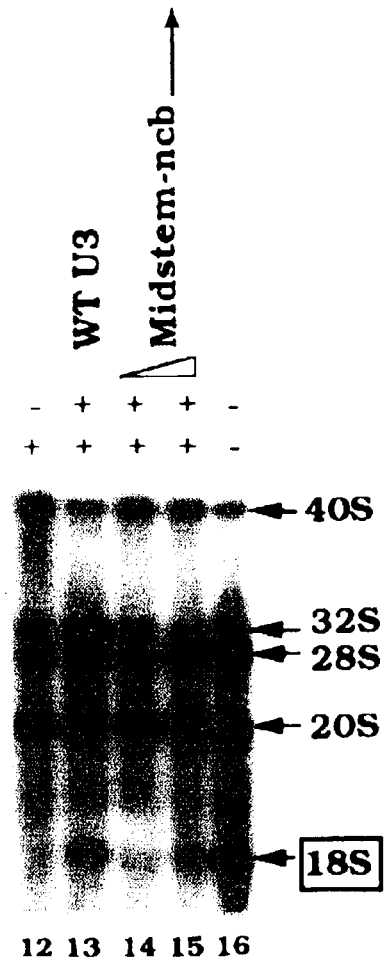
FIG. 5B               FIG. 5C

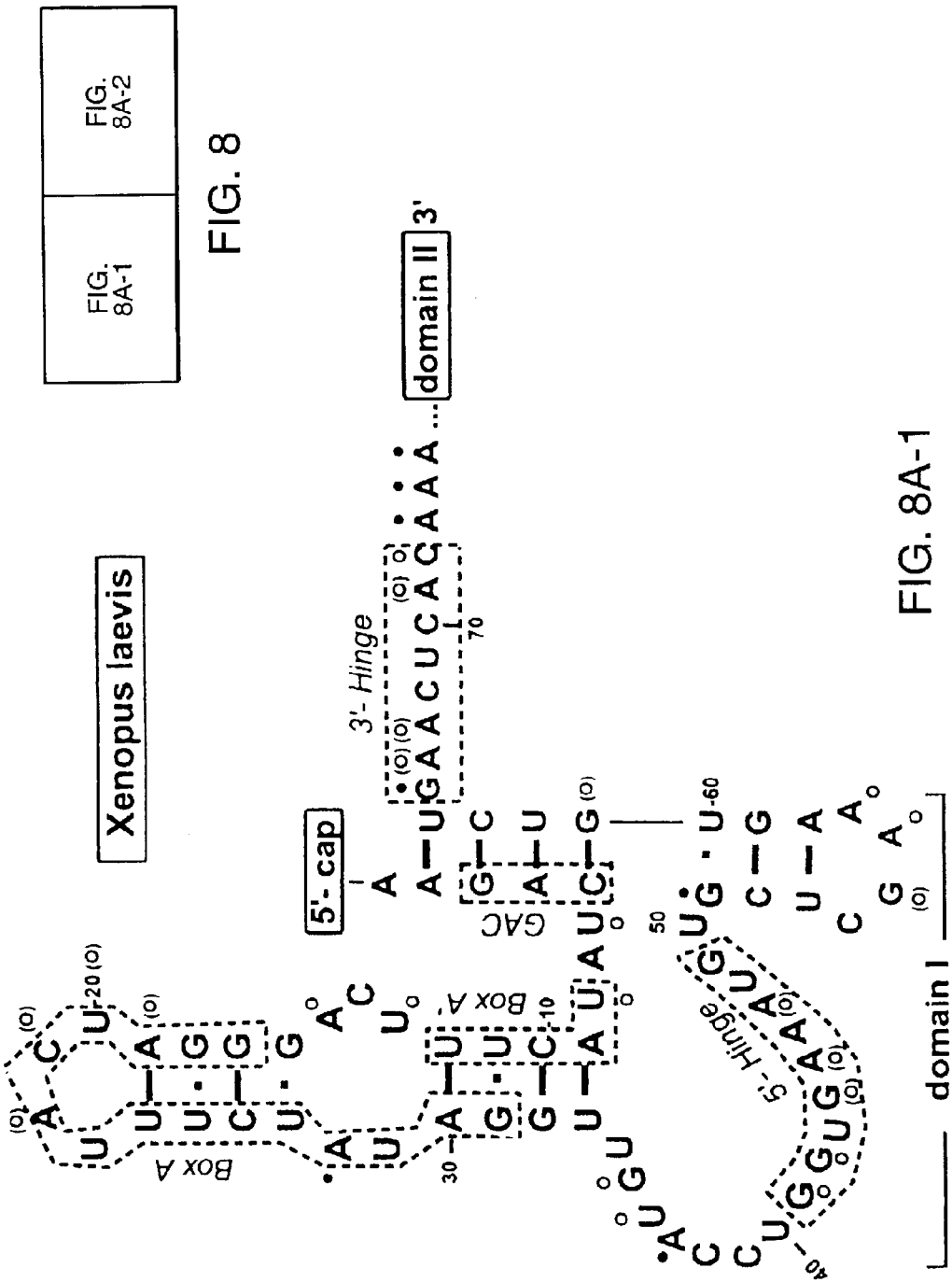

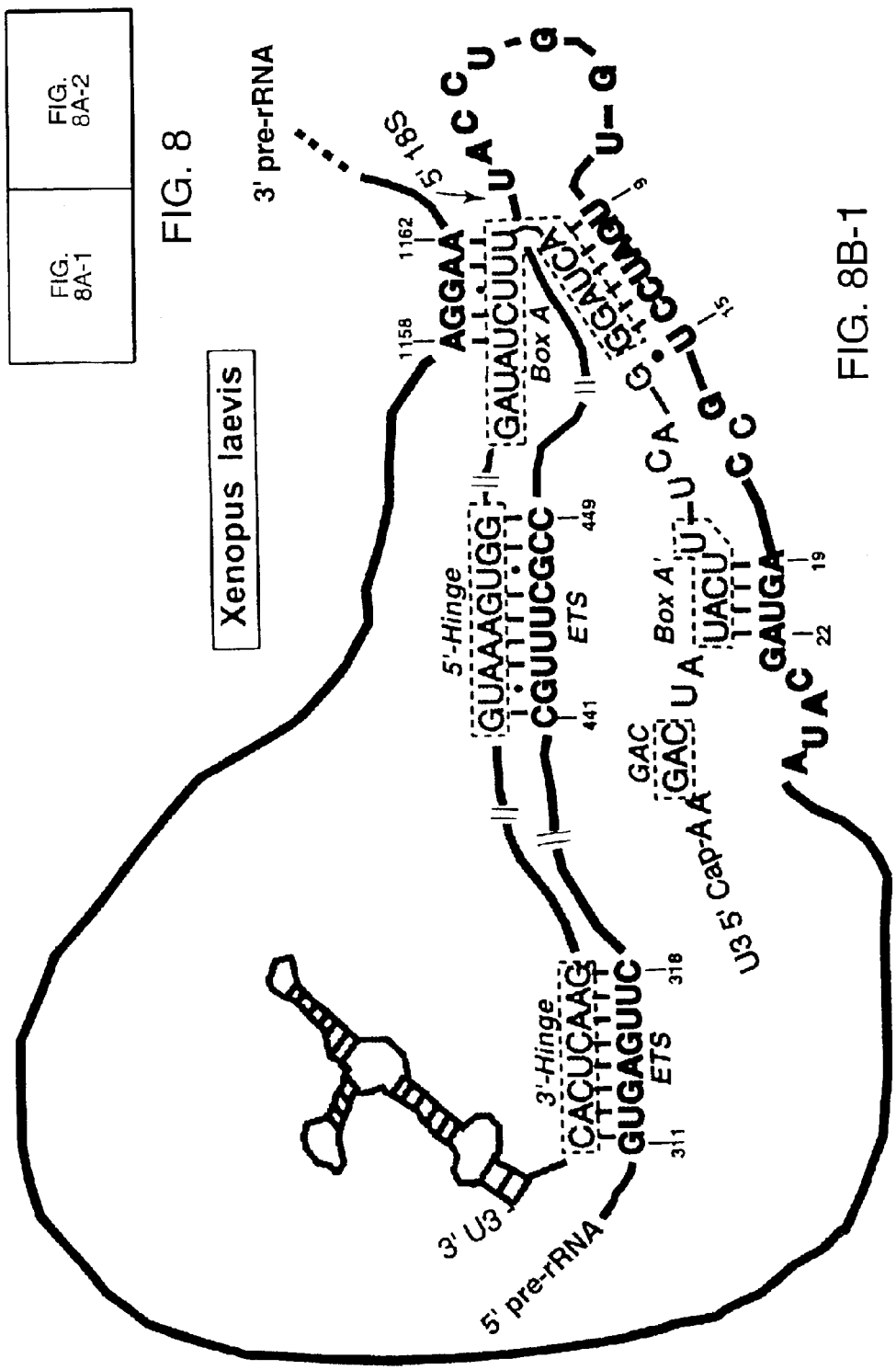

SEQUENCE LISTING

<160> NUMBER OF SEQ ID NOS: 128

<210> SEQ ID NO 1
<211> LENGTH: 5
<212> TYPE: RNA
<213> ORGANISM: Artificial Sequence
<220> FEATURE:
<223> OTHER INFORMATION: Evolutionarily conserved sequence within the domain I of U3 snoRNA

<400> SEQUENCE: 1 uacuu                                                                   5

<210> SEQ ID NO 2
<211> LENGTH: 15

```
<212> TYPE: RNA
<213> ORGANISM: Artificial Sequence
<220> FEATURE:
<223> OTHER INFORMATION: Evolutionarily conserved sequence within the domain I of U3
      snoRNA
<220> FEATURE:
<221> NAME/KEY: misc_feature
<222> LOCATION: (6)..(6)
<223> OTHER INFORMATION: n is a, g, c, or u

<400> SEQUENCE: 2
graucnkuuy wwkak                                                    15

<210> SEQ ID NO 3
<211> LENGTH: 10
<212> TYPE: RNA
<213> ORGANISM: Saccharomyces cerevisiae

<400> SEQUENCE: 3
cacucuuuga                                                          10

<210> SEQ ID NO 4
<211> LENGTH: 11
<212> TYPE: RNA
<213> ORGANISM: Saccharomyces cerevisiae

<400> SEQUENCE: 4
ccacugaauc c                                                        11

<210> SEQ ID NO 5
<211> LENGTH: 12
<212> TYPE: RNA
<213> ORGANISM: Hansenula wingei

<400> SEQUENCE: 5
cccucuuugu cu                                                       12

<210> SEQ ID NO 6
<211> LENGTH: 14
<212> TYPE: RNA
<213> ORGANISM: Hansenula wingei

<400> SEQUENCE: 6
gagccacuga aucc                                                     14

<210> SEQ ID NO 7
<211> LENGTH: 6
<212> TYPE: RNA
<213> ORGANISM: Schizosaccharomyces pombe

<400> SEQUENCE: 7 uggguu                                                               6

<210> SEQ ID NO 8
<211> LENGTH: 5
<212> TYPE: RNA
<213> ORGANISM: Schizosaccharomyces pombe

<400> SEQUENCE: 8 cagaa                                                                5

<210> SEQ ID NO 9
<211> LENGTH: 6
<212> TYPE: RNA
<213> ORGANISM: Trypanosoma brucei
```

```
<400> SEQUENCE: 9 uuaaau                                                              6

<210> SEQ ID NO 10
<211> LENGTH: 12
<212> TYPE: RNA
<213> ORGANISM: Trypanosoma brucei

<400> SEQUENCE: 10
aaauaaccaa ca                                                      12

<210> SEQ ID NO 11
<211> LENGTH: 9
<212> TYPE: RNA
<213> ORGANISM: Homo sapiens

<400> SEQUENCE: 11 cuagagaag                                                           9

<210> SEQ ID NO 12
<211> LENGTH: 7
<212> TYPE: RNA
<213> ORGANISM: Homo sapiens

<400> SEQUENCE: 12 agagcac                                                             7

<210> SEQ ID NO 13
<211> LENGTH: 7
<212> TYPE: RNA
<213> ORGANISM: Artificial Sequence
<220> FEATURE:
<223> OTHER INFORMATION: Evolutionarily conserved U3 snoRNA Domain II regions

<400> SEQUENCE: 13 aggaaga                                                             7

<210> SEQ ID NO 14
<211> LENGTH: 8
<212> TYPE: RNA
<213> ORGANISM: Artificial Sequence
<220> FEATURE:
<223> OTHER INFORMATION: Evolutionarily conserved U3 snoRNA Domain II regions

<400> SEQUENCE: 14 agcgugaa                                                            8

<210> SEQ ID NO 15
<211> LENGTH: 8
<212> TYPE: RNA
<213> ORGANISM: Artificial Sequence
<220> FEATURE:
<223> OTHER INFORMATION: Evolutionarily conserved U3 snoRNA Domain II regions

<400> SEQUENCE: 15 auugauga                                                            8

<210> SEQ ID NO 16
<211> LENGTH: 5
<212> TYPE: RNA
<213> ORGANISM: Artificial Sequence
<220> FEATURE:
<223> OTHER INFORMATION: Evolutionarily conserved U3 snoRNA Domain II regions
```

-continued

```
<400> SEQUENCE: 16 gcuga                                                                  5

<210> SEQ ID NO 17
<211> LENGTH: 10
<212> TYPE: RNA
<213> ORGANISM: Saccharomyces cerevisiae

<400> SEQUENCE: 17
ucaaagagug                                                            10

<210> SEQ ID NO 18
<211> LENGTH: 11
<212> TYPE: RNA
<213> ORGANISM: Saccharomyces cerevisiae

<400> SEQUENCE: 18
ggauuuggug g                                                          11

<210> SEQ ID NO 19
<211> LENGTH: 12
<212> TYPE: RNA
<213> ORGANISM: Hansenula wingei

<400> SEQUENCE: 19
aaacaaagag gg                                                         12

<210> SEQ ID NO 20
<211> LENGTH: 15
<212> TYPE: RNA
<213> ORGANISM: Hansenula wingei

<400> SEQUENCE: 20
ggauuuuagu ggauu                                                      15

<210> SEQ ID NO 21
<211> LENGTH: 7
<212> TYPE: RNA
<213> ORGANISM: Schizosaccharomyces pombe

<400> SEQUENCE: 21 aaccuca                                                                7

<210> SEQ ID NO 22
<211> LENGTH: 5
<212> TYPE: RNA
<213> ORGANISM: Schizosaccharomyces pombe

<400> SEQUENCE: 22 uucug                                                                  5

<210> SEQ ID NO 23
<211> LENGTH: 7
<212> TYPE: RNA
<213> ORGANISM: Trypanosoma brucei

<400> SEQUENCE: 23 auuuaua                                                                7

<210> SEQ ID NO 24
<211> LENGTH: 12
<212> TYPE: RNA
<213> ORGANISM: Trypanosoma brucei
```

```
<400> SEQUENCE: 24
uguugguugu gu                                                              12

<210> SEQ ID NO 25
<211> LENGTH: 9
<212> TYPE: RNA
<213> ORGANISM: Homo sapiens

<400> SEQUENCE: 25 cuucucuag                                                                   9

<210> SEQ ID NO 26
<211> LENGTH: 7
<212> TYPE: RNA
<213> ORGANISM: Homo sapiens

<400> SEQUENCE: 26 gugcucu                                                                     7

<210> SEQ ID NO 27
<211> LENGTH: 42
<212> TYPE: DNA
<213> ORGANISM: Artificial Sequence
<220> FEATURE:
<223> OTHER INFORMATION: (sense) primer for PCR mutagenesis of various U3 snoRNA

<400> SEQUENCE: 27
taatacgact cactataggg aagactatac tttcagggat ca                              42

<210> SEQ ID NO 28
<211> LENGTH: 31
<212> TYPE: DNA
<213> ORGANISM: Artificial Sequence
<220> FEATURE:
<223> OTHER INFORMATION: (anti-sense) primer for PCR mutagenesis of various U3 snoRNA

<400> SEQUENCE: 28
taaaaccact cagcctgtgt tctctccctc c                                         31

<210> SEQ ID NO 29
<211> LENGTH: 41
<212> TYPE: DNA
<213> ORGANISM: Artificial Sequence
<220> FEATURE:
<223> OTHER INFORMATION: 5'-ncb 5' (sense) PCR primer for mutagenesis of U3 snoRNA

<400> SEQUENCE: 29
taatacgact cactataggg aagactaatg aaagtcggat c                              41

<210> SEQ ID NO 30
<211> LENGTH: 41
<212> TYPE: DNA
<213> ORGANISM: Artificial Sequence
<220> FEATURE:
<223> OTHER INFORMATION: 5'-cb 5' (sense) PCR primer for mutagenesis of U3 snoRNA

<400> SEQUENCE: 30
taatacgact cactataggg aagacttgtc tgaattggat c                              41

<210> SEQ ID NO 31
<211> LENGTH: 36
<212> TYPE: DNA
<213> ORGANISM: Artificial Sequence
<220> FEATURE:
```

-continued

<223> OTHER INFORMATION: 4 nt sub/loop I: sense primer for making U3 sno Mutants

<400> SEQUENCE: 31
cagggatcat ttctataggt acatcctggt gaaatg           36

<210> SEQ ID NO 32
<211> LENGTH: 32
<212> TYPE: DNA
<213> ORGANISM: Artificial Sequence
<220> FEATURE:
<223> OTHER INFORMATION: Delta 4 nt/loop I: sense primer for making U3 sno Mutants

<400> SEQUENCE: 32
cagggatcat ttctataggt cctggtgaaa tg           32

<210> SEQ ID NO 33
<211> LENGTH: 33
<212> TYPE: DNA
<213> ORGANISM: Artificial Sequence
<220> FEATURE:
<223> OTHER INFORMATION: 4 nt ins/loop I: sense primer for making U3 sno Mutants

<400> SEQUENCE: 33
cagggatcat ttctataggt tatgtattcc tgg           33

<210> SEQ ID NO 34
<211> LENGTH: 36
<212> TYPE: DNA
<213> ORGANISM: Artificial Sequence
<220> FEATURE:
<223> OTHER INFORMATION: Topstem-ncb/R: sense primer for making U3 sno Mutants

<400> SEQUENCE: 34
cagggatcat ttctataggt tgtaggatgt gaaatg           36

<210> SEQ ID NO 35
<211> LENGTH: 28
<212> TYPE: DNA
<213> ORGANISM: Artificial Sequence
<220> FEATURE:
<223> OTHER INFORMATION: Topstem-ncb/L: sense primer for making U3 sno Mutants

<400> SEQUENCE: 35
cagggatcat ttctagtcct tgtacctg           28

<210> SEQ ID NO 36
<211> LENGTH: 36
<212> TYPE: DNA
<213> ORGANISM: Artificial Sequence
<220> FEATURE:
<223> OTHER INFORMATION: Topstem-cb: sense primer for making U3 sno Mutants

<400> SEQUENCE: 36
cagggatcat ttctagtcct tgtaggatgt gaaatg           36

<210> SEQ ID NO 37
<211> LENGTH: 38
<212> TYPE: DNA
<213> ORGANISM: Artificial Sequence
<220> FEATURE:
<223> OTHER INFORMATION: Delta (2+2): sense primer for making U3 sno Mutants

<400> SEQUENCE: 37
cagggatcat ttctataggt tgtacctgga aatgctcg           38

<210> SEQ ID NO 38
<211> LENGTH: 33
<212> TYPE: DNA
<213> ORGANISM: Artificial Sequence
<220> FEATURE:
<223> OTHER INFORMATION: Sense primer for amplification of U3 5'H/intag-16 mutant

<400> SEQUENCE: 38
ggaagaattc agacaatgaa ctcacaaacc acg           33

<210> SEQ ID NO 39
<211> LENGTH: 34
<212> TYPE: DNA
<213> ORGANISM: Artificial Sequence
<220> FEATURE:
<223> OTHER INFORMATION: Anti-sense primer for amplification of U3 5'H/intag-16 mutant

<400> SEQUENCE: 39
aagggaattc acttgacact ttcgagcaca tttc          34

<210> SEQ ID NO 40
<211> LENGTH: 39
<212> TYPE: DNA
<213> ORGANISM: Artificial Sequence
<220> FEATURE:
<223> OTHER INFORMATION: Sense primer for amplification of 3'/H/intag-16 mutant

<400> SEQUENCE: 40
ctgaactcac aaaaagtgaa ttcagacaac cacgaggaa     39

<210> SEQ ID NO 41
<211> LENGTH: 34
<212> TYPE: DNA
<213> ORGANISM: Artificial Sequence
<220> FEATURE:
<223> OTHER INFORMATION: Anti-sense primer for amplification of 3'/H/intag-16 mutant

<400> SEQUENCE: 41
tcctcgtggg aattcacttt tgtgagttc agac           34

<210> SEQ ID NO 42
<211> LENGTH: 33
<212> TYPE: DNA
<213> ORGANISM: Artificial Sequence
<220> FEATURE:
<223> OTHER INFORMATION: Sense primer for amplification of 3'H/intag-10 mutant

<400> SEQUENCE: 42
ctgaactcac aaaaagtgaa ttcccacgag gaa           33

<210> SEQ ID NO 43
<211> LENGTH: 39
<212> TYPE: DNA
<213> ORGANISM: Artificial Sequence
<220> FEATURE:
<223> OTHER INFORMATION: Anti-sense primer for amplification of U3 subtag-16 mutant

<400> SEQUENCE: 43
gagttcagac actgaattca cttttttcacc aggtacaac    39

<210> SEQ ID NO 44
<211> LENGTH: 41
<212> TYPE: DNA
<213> ORGANISM: Artificial Sequence
<220> FEATURE:
<223> OTHER INFORMATION: First step anti-sense primer for amplification of U3 subtag-10 mutant

```
<400> SEQUENCE: 44
tataggttgt acctggtgaa atgtgctaat tcagacactg a                              41

<210> SEQ ID NO 45
<211> LENGTH: 28
<212> TYPE: DNA
<213> ORGANISM: Artificial Sequence
<220> FEATURE:
<223> OTHER INFORMATION: Second step anti-sense primer for amplification of U3 subtag-10
      mutant

<400> SEQUENCE: 45
cagggatcat ttctataggt tgtacctg                                             28

<210> SEQ ID NO 46
<211> LENGTH: 30
<212> TYPE: DNA
<213> ORGANISM: Artificial Sequence
<220> FEATURE:
<223> OTHER INFORMATION: sub/2+2: primer for creating additional mutants in U3 domain I

<400> SEQUENCE: 46
tataggttgt acctgccgaa atgacctcga                                           30

<210> SEQ ID NO 47
<211> LENGTH: 34
<212> TYPE: DNA
<213> ORGANISM: Artificial Sequence
<220> FEATURE:
<223> OTHER INFORMATION: ins/2+2: primer for creating additional mutants in U3 domain I

<400> SEQUENCE: 47
tataggttgt acctgccgtg aaatgtgcac tcga                                      34

<210> SEQ ID NO 48
<211> LENGTH: 33
<212> TYPE: DNA
<213> ORGANISM: Artificial Sequence
<220> FEATURE:
<223> OTHER INFORMATION: Midstem-ncb: primer for creating additional mutants in U3 domain
      I

<400> SEQUENCE: 48
tataggttgt acctggtctt tactgctcga aag                                       33

<210> SEQ ID NO 49
<211> LENGTH: 30
<212> TYPE: DNA
<213> ORGANISM: Artificial Sequence
<220> FEATURE:
<223> OTHER INFORMATION: no bulge: primer for creating additional mutants in U3 domain I

<400> SEQUENCE: 49
tataggttgt acctgtagaa atgatctcga                                           30

<210> SEQ ID NO 50
<211> LENGTH: 38
<212> TYPE: DNA
<213> ORGANISM: Artificial Sequence
<220> FEATURE:
<223> OTHER INFORMATION: Delta 4nt/Bottom: primer for creating additional mutants in U3
      domain I

<400> SEQUENCE: 50
tataggttgt acctggtgaa atgtgctcga aactgaac                                  38
```

<210> SEQ ID NO 51
<211> LENGTH: 59
<212> TYPE: DNA
<213> ORGANISM: Artificial Sequence
<220> FEATURE:
<223> OTHER INFORMATION: 5'H/intag-10: primer for creating additional mutants in U3 domain I

<400> SEQUENCE: 51
tataggttgt acctggtgaa atgtgctcga aagtgtaatt cagacactga actcacaaa    59

<210> SEQ ID NO 52
<211> LENGTH: 46
<212> TYPE: DNA
<213> ORGANISM: Artificial Sequence
<220> FEATURE:
<223> OTHER INFORMATION: 5'H/intag-4: primer for creating additional mutants in U3 domain I

<400> SEQUENCE: 52
tataggttgt acctggtgaa atgtgctcga aagtgtgaca ctgaac    46

<210> SEQ ID NO 53
<211> LENGTH: 6
<212> TYPE: DNA
<213> ORGANISM: Trypanosoma brucei

<400> SEQUENCE: 53 atttaa    6

<210> SEQ ID NO 54
<211> LENGTH: 12
<212> TYPE: DNA
<213> ORGANISM: Trypanosoma brucei

<400> SEQUENCE: 54
tgttggttgt gt    12

<210> SEQ ID NO 55
<211> LENGTH: 224
<212> TYPE: RNA
<213> ORGANISM: Artificial Sequence
<220> FEATURE:
<223> OTHER INFORMATION: U3 snoRNA

<400> SEQUENCE: 55
aagacuauac uuucagggau cauuucuaua gguuguaccu ggugaaaugu gcucgaaagu    60
gucugaacuc acaaaccacg aggaagagcg ucagguuucu cuccgagcg ugaagugagc    120 ucacagugcu gcuucauugu ggcugcuguu ugcuauugau gaacguucug cuccccuuua    180
uuauugggga gauggaggga gagaacacag gcugaguggu uuua    224

<210> SEQ ID NO 56
<211> LENGTH: 75
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 56
aagacuauac uuucagggau cauuucuaua gguuguaccu ggugaaaugu gcucgaaagu    60
gucugaacuc acaaa    75

```
<210> SEQ ID NO 57
<211> LENGTH: 79
<212> TYPE: RNA
<213> ORGANISM: Artificial Sequence
<220> FEATURE:
<223> OTHER INFORMATION: 4 nt ins/loop I Mutant

<400> SEQUENCE: 57
aagacuauac uuucagggau cauuucuaua gguuauguau uccggugaa augugcucga      60 aagugucuga acucacaaa                                                 79

<210> SEQ ID NO 58
<211> LENGTH: 75
<212> TYPE: RNA
<213> ORGANISM: Artificial Sequence
<220> FEATURE:
<223> OTHER INFORMATION: sub 2+2 Mutant

<400> SEQUENCE: 58
aagacuauac uuucagggau cauuucuaua gguuguaccu gccgaaaugc acucgaaagu    60
gucugaacuc acaaa                                                     75

<210> SEQ ID NO 59
<211> LENGTH: 75
<212> TYPE: RNA
<213> ORGANISM: Artificial Sequence
<220> FEATURE:
<223> OTHER INFORMATION: no bulge mutant

<400> SEQUENCE: 59
aagacuauac uuucagggau cauuucuaua gguuguaccu guagaaauga ucucgaaagu    60
gucugaacuc acaaa                                                     75

<210> SEQ ID NO 60
<211> LENGTH: 79
<212> TYPE: RNA
<213> ORGANISM: Artificial Sequence
<220> FEATURE:
<223> OTHER INFORMATION: ins/2+2 Mutant

<400> SEQUENCE: 60
aagacuauac uuucagggau cauuucuaua gguuguaccu gccgugaaau gugcacucga    60
aagugucuga acucacaaa                                                 79

<210> SEQ ID NO 61
<211> LENGTH: 71
<212> TYPE: RNA
<213> ORGANISM: Artificial Sequence
<220> FEATURE:
<223> OTHER INFORMATION: Delta 2+2 Mutant

<400> SEQUENCE: 61
aagacuauac uuucagggau cauuucuaua gguuguaccu ggaaaugcuc gaaagugucu    60
gaacucacaa a                                                         71

<210> SEQ ID NO 62
<211> LENGTH: 71
<212> TYPE: RNA
<213> ORGANISM: Artificial Sequence
<220> FEATURE:
<223> OTHER INFORMATION: Delta 4 nt/Bottom Mutant

<400> SEQUENCE: 62
```
aagacuauac uuucagggau cauuucuaua gguuguaccu ggugaaaugu gcucgaaacu    60
gaacucacaa a                                                         71

<210> SEQ ID NO 63
<211> LENGTH: 63
<212> TYPE: RNA
<213> ORGANISM: Artificial Sequence
<220> FEATURE:
<223> OTHER INFORMATION: U3 snoRNA Domain I

<400> SEQUENCE: 63
aagacuauac uuucagggau cauuucuaua gguuguaccu ggugaaaugu gcucgaaagu    60
guc                                                                  63

<210> SEQ ID NO 64
<211> LENGTH: 25
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 64
gugucugaac ucacaaacca cgagg                                          25

<210> SEQ ID NO 65
<211> LENGTH: 8
<212> TYPE: RNA
<213> ORGANISM: Artificial Sequence
<220> FEATURE:
<223> OTHER INFORMATION: Tag*

<400> SEQUENCE: 65 uuuagaua                                                             8

<210> SEQ ID NO 66
<211> LENGTH: 10
<212> TYPE: RNA
<213> ORGANISM: Artificial Sequence
<220> FEATURE:
<223> OTHER INFORMATION: 3'H/intag-10

<400> SEQUENCE: 66
aagugaauuc                                                           10

<210> SEQ ID NO 67
<211> LENGTH: 16
<212> TYPE: RNA
<213> ORGANISM: Artificial Sequence
<220> FEATURE:
<223> OTHER INFORMATION: 3'H/intag-16

<400> SEQUENCE: 67
aagugaauuc agacaa                                                    16

<210> SEQ ID NO 68
<211> LENGTH: 25
<212> TYPE: RNA
<213> ORGANISM: Artificial Sequence
<220> FEATURE:
<223> OTHER INFORMATION: Tag* Mutant

<400> SEQUENCE: 68
gugucuuuua gauaaaacca cgagg                                          25

<210> SEQ ID NO 69
<211> LENGTH: 41
<212> TYPE: RNA
<213> ORGANISM: Artificial Sequence
<220> FEATURE:
<223> OTHER INFORMATION: 3'H/intag-16 Mutant

<400> SEQUENCE: 69
gugucugaac ucacaaaaag ugaauucaga caaccacgag g        41

<210> SEQ ID NO 70
<211> LENGTH: 35
<212> TYPE: RNA
<213> ORGANISM: Artificial Sequence
<220> FEATURE:
<223> OTHER INFORMATION: 3'H/intag-10 Mutant

<400> SEQUENCE: 70
gugucugaac ucacaaaaag ugaauuccca cgagg        35

<210> SEQ ID NO 71
<211> LENGTH: 20
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 71
aaagugucug aacucacaaa        20

<210> SEQ ID NO 72
<211> LENGTH: 10
<212> TYPE: RNA
<213> ORGANISM: Artificial Sequence
<220> FEATURE:
<223> OTHER INFORMATION: 5'H intag-10

<400> SEQUENCE: 72
aauucagaca        10

<210> SEQ ID NO 73
<211> LENGTH: 4
<212> TYPE: DNA
<213> ORGANISM: Artificial Sequence
<220> FEATURE:
<223> OTHER INFORMATION: 5'H intag-4

<400> SEQUENCE: 73 gaca        4

<210> SEQ ID NO 74
<211> LENGTH: 16
<212> TYPE: RNA
<213> ORGANISM: Artificial Sequence
<220> FEATURE:
<223> OTHER INFORMATION: 5'H intag-16

<400> SEQUENCE: 74
aagugaauuc agacaa        16

<210> SEQ ID NO 75
<211> LENGTH: 30
<212> TYPE: RNA
<213> ORGANISM: Artificial Sequence
<220> FEATURE:
<223> OTHER INFORMATION: 5'H/intag-10 Mutant

```
<400> SEQUENCE: 75
aaaguguaau ucagacacug aacucacaaa                    30

<210> SEQ ID NO 76
<211> LENGTH: 24
<212> TYPE: RNA
<213> ORGANISM: Artificial Sequence
<220> FEATURE:
<223> OTHER INFORMATION: 5'H/intag-4 Mutant

<400> SEQUENCE: 76
aaagugugac acugaacuca caaa                          24

<210> SEQ ID NO 77
<211> LENGTH: 36
<212> TYPE: RNA
<213> ORGANISM: Artificial Sequence
<220> FEATURE:
<223> OTHER INFORMATION: 5'H/intag-16 Mutant

<400> SEQUENCE: 77
aaagugucaa gugaauucag acaaugaacu cacaaa             36

<210> SEQ ID NO 78
<211> LENGTH: 23
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 78
cauuucuaua gguuguaccu ggu                           23

<210> SEQ ID NO 79
<211> LENGTH: 4
<212> TYPE: RNA
<213> ORGANISM: Artificial Sequence
<220> FEATURE:
<223> OTHER INFORMATION: Topstem-ncb/L

<400> SEQUENCE: 79 gucg                                                4

<210> SEQ ID NO 80
<211> LENGTH: 23
<212> TYPE: RNA
<213> ORGANISM: Artificial Sequence
<220> FEATURE:
<223> OTHER INFORMATION: Topstem-ncb/L  Mutant

<400> SEQUENCE: 80
cauuucuagu cguuguaccu ggu                           23

<210> SEQ ID NO 81
<211> LENGTH: 23
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 81
uauagguugu accuggugaa aug                           23

<210> SEQ ID NO 82
```

```
<211> LENGTH: 4
<212> TYPE: RNA
<213> ORGANISM: Artificial Sequence
<220> FEATURE:
<223> OTHER INFORMATION: Topstem-ncb/R

<400> SEQUENCE: 82 ggau                                                                       4

<210> SEQ ID NO 83
<211> LENGTH: 23
<212> TYPE: RNA
<213> ORGANISM: Artificial Sequence
<220> FEATURE:
<223> OTHER INFORMATION: Topstem-ncb/R

<400> SEQUENCE: 83
uauagguugu aggaugugaa aug                                                 23

<210> SEQ ID NO 84
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 84
guaccuggug aaaugugcuc gaaa                                                24

<210> SEQ ID NO 85
<211> LENGTH: 6
<212> TYPE: RNA
<213> ORGANISM: Artificial Sequence
<220> FEATURE:
<223> OTHER INFORMATION: Midstem-ncb

<400> SEQUENCE: 85 cuuuac                                                                     6

<210> SEQ ID NO 86
<211> LENGTH: 24
<212> TYPE: RNA
<213> ORGANISM: Artificial Sequence
<220> FEATURE:
<223> OTHER INFORMATION: Midstem-ncb Mutant

<400> SEQUENCE: 86
guaccugguc uuuacugcuc gaaa                                                24

<210> SEQ ID NO 87
<211> LENGTH: 27
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 87
uuucuauagg uuguaccugg ugaaaug                                             27

<210> SEQ ID NO 88
<211> LENGTH: 31
<212> TYPE: RNA
<213> ORGANISM: Artificial Sequence
<220> FEATURE:
<223> OTHER INFORMATION: 4 ntins/loop I Mutant

<400> SEQUENCE: 88
```
uuucuauagg uuauguauuc cuggugaaau g                                      31

<210> SEQ ID NO 89
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 89
guaccuggug aaaugugcuc gaaa                                              24

<210> SEQ ID NO 90
<211> LENGTH: 24
<212> TYPE: RNA
<213> ORGANISM: Artificial Sequence
<220> FEATURE:
<223> OTHER INFORMATION: sub 2+2 Mutant

<400> SEQUENCE: 90
guaccugccg aaaugcacuc gaaa                                              24

<210> SEQ ID NO 91
<211> LENGTH: 24
<212> TYPE: RNA
<213> ORGANISM: Artificial Sequence
<220> FEATURE:
<223> OTHER INFORMATION: No Bulge Mutant

<400> SEQUENCE: 91
guaccuguag aaaugaucuc gaaa                                              24

<210> SEQ ID NO 92
<211> LENGTH: 28
<212> TYPE: RNA
<213> ORGANISM: Artificial Sequence
<220> FEATURE:
<223> OTHER INFORMATION: ins/2+2 Mutant

<400> SEQUENCE: 92
guaccugccg ugaaaugugc acucgaaa                                          28

<210> SEQ ID NO 93
<211> LENGTH: 20
<212> TYPE: RNA
<213> ORGANISM: Artificial Sequence
<220> FEATURE:
<223> OTHER INFORMATION: Delta 2+2 Mutant

<400> SEQUENCE: 93
guaccuggaa augcucgaaa                                                   20

<210> SEQ ID NO 94
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 94
cucgaaagug ucugaacuca caaa                                              24

<210> SEQ ID NO 95
<211> LENGTH: 20
<212> TYPE: RNA

```
<213> ORGANISM: Artificial Sequence
<220> FEATURE:
<223> OTHER INFORMATION: Delta 4 nt/Bottom Mutant

<400> SEQUENCE: 95
cucgaaacug aacucacaaa                                               20

<210> SEQ ID NO 96
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 96
aaaugugcuc gaaagugucu gaac                                          24

<210> SEQ ID NO 97
<211> LENGTH: 16
<212> TYPE: RNA
<213> ORGANISM: Artificial Sequence
<220> FEATURE:
<223> OTHER INFORMATION: subtag-16

<400> SEQUENCE: 97
aagugaauuc agacaa                                                   16

<210> SEQ ID NO 98
<211> LENGTH: 10
<212> TYPE: RNA
<213> ORGANISM: Artificial Sequence
<220> FEATURE:
<223> OTHER INFORMATION: subtag-10

<400> SEQUENCE: 98
aauucagaca                                                          10

<210> SEQ ID NO 99
<211> LENGTH: 24
<212> TYPE: RNA
<213> ORGANISM: Artificial Sequence
<220> FEATURE:
<223> OTHER INFORMATION: subtag-16 Mutant

<400> SEQUENCE: 99
aaaaagugaa uucagacaau gaac                                          24

<210> SEQ ID NO 100
<211> LENGTH: 25
<212> TYPE: RNA
<213> ORGANISM: Artificial Sequence
<220> FEATURE:
<223> OTHER INFORMATION: subtag-10 Mutant

<400> SEQUENCE: 100
aaaugugcua auucagacac ugaac                                         25

<210> SEQ ID NO 101
<211> LENGTH: 23
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 101
uuucuauagg uuguaccugg uga                                           23
```

<210> SEQ ID NO 102
<211> LENGTH: 4
<212> TYPE: RNA
<213> ORGANISM: Artificial Sequence
<220> FEATURE:
<223> OTHER INFORMATION: 4 nt sub/loop I

<400> SEQUENCE: 102 acau                                                                    4

<210> SEQ ID NO 103
<211> LENGTH: 23
<212> TYPE: RNA
<213> ORGANISM: Artificial Sequence
<220> FEATURE:
<223> OTHER INFORMATION: 4 nt sub/loop I Mutant

<400> SEQUENCE: 103
uuucuauagg uacauccugg uga                                              23

<210> SEQ ID NO 104
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 104
uuucuauagg uuguaccugg ugaa                                             24

<210> SEQ ID NO 105
<211> LENGTH: 20
<212> TYPE: RNA
<213> ORGANISM: Artificial Sequence
<220> FEATURE:
<223> OTHER INFORMATION: Delta 4 nt/loop I

<400> SEQUENCE: 105
uuucuauagg uccuggugaa                                                  20

<210> SEQ ID NO 106
<211> LENGTH: 24
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 106
aagacuauac uuucagggau cauu                                             24

<210> SEQ ID NO 107
<211> LENGTH: 9
<212> TYPE: RNA
<213> ORGANISM: Artificial Sequence
<220> FEATURE:
<223> OTHER INFORMATION: 5'-ncb

<400> SEQUENCE: 107 augaaaguc                                                               9

<210> SEQ ID NO 108
<211> LENGTH: 10
<212> TYPE: RNA
<213> ORGANISM: Artificial Sequence
<220> FEATURE:

```
<223> OTHER INFORMATION: 5'-cb

<400> SEQUENCE: 108
ugucugaauu                                                              10

<210> SEQ ID NO 109
<211> LENGTH: 24
<212> TYPE: RNA
<213> ORGANISM: Artificial Sequence
<220> FEATURE:
<223> OTHER INFORMATION: 5'-ncb Mutant

<400> SEQUENCE: 109
aagacuaaug aaagucggau cauu                                              24

<210> SEQ ID NO 110
<211> LENGTH: 24
<212> TYPE: RNA
<213> ORGANISM: Artificial Sequence
<220> FEATURE:
<223> OTHER INFORMATION: 5'-cb Mutant

<400> SEQUENCE: 110
aagacuuguc ugaauuggau cauu                                              24

<210> SEQ ID NO 111
<211> LENGTH: 23
<212> TYPE: RNA
<213> ORGANISM: Artificial Sequence
<220> FEATURE:
<223> OTHER INFORMATION: Evolutionarily conserved sequence of U3 snoRNA

<400> SEQUENCE: 111
uuucuauagg uuguaccugg uga                                               23

<210> SEQ ID NO 112
<211> LENGTH: 23
<212> TYPE: RNA
<213> ORGANISM: Artificial Sequence
<220> FEATURE:
<223> OTHER INFORMATION: Topstem-cb Mutant

<400> SEQUENCE: 112
uuucuagucc uuguaggaug uga                                               23

<210> SEQ ID NO 113
<211> LENGTH: 75
<212> TYPE: RNA
<213> ORGANISM: Xenopus laevis

<400> SEQUENCE: 113
aagacuauac uuucagggau cauuucuaua gguuguaccu ggugaaaugu gcucgaaagu        60
gucugaacuc acaaa                                                        75

<210> SEQ ID NO 114
<211> LENGTH: 72
<212> TYPE: RNA
<213> ORGANISM: Saccharomyces cerevisiae

<400> SEQUENCE: 114
gucgacguac uuauaggauc auuucuauag gaaucgucac ucuuugacuc uucaaaagag        60
ccacugaauc ca                                                           72
```

```
<210> SEQ ID NO 115
<211> LENGTH: 8
<212> TYPE: RNA
<213> ORGANISM: Xenopus laevis

<400> SEQUENCE: 115 gugaguuc                                                                  8

<210> SEQ ID NO 116
<211> LENGTH: 9
<212> TYPE: RNA
<213> ORGANISM: Xenopus laevis

<400> SEQUENCE: 116 cguuucgcc                                                                 9

<210> SEQ ID NO 117
<211> LENGTH: 27
<212> TYPE: RNA
<213> ORGANISM: Xenopus laevis

<400> SEQUENCE: 117
uaccugguug auccugccag uagcaua                                            27

<210> SEQ ID NO 118
<211> LENGTH: 5
<212> TYPE: RNA
<213> ORGANISM: Xenopus laevis

<400> SEQUENCE: 118 aggaa                                                                     5

<210> SEQ ID NO 119
<211> LENGTH: 31
<212> TYPE: RNA
<213> ORGANISM: Xenopus laevis

<400> SEQUENCE: 119
aagacuauac uuucagggau cauuucuaua g                                       31

<210> SEQ ID NO 120
<211> LENGTH: 9
<212> TYPE: RNA
<213> ORGANISM: Xenopus laevis

<400> SEQUENCE: 120 ggugaaaug                                                                 9

<210> SEQ ID NO 121
<211> LENGTH: 8
<212> TYPE: RNA
<213> ORGANISM: Xenopus laevis

<400> SEQUENCE: 121 gaacucac                                                                  8

<210> SEQ ID NO 122
<211> LENGTH: 11
<212> TYPE: RNA
<213> ORGANISM: Saccharomyces cervisae

<400> SEQUENCE: 122
ggauuuggug g                                                             11
```

-continued

```
<210> SEQ ID NO 123
<211> LENGTH: 10
<212> TYPE: RNA
<213> ORGANISM: Saccharomyces cerevisiae

<400> SEQUENCE: 123
ucaaagagug                                                          10

<210> SEQ ID NO 124
<211> LENGTH: 27
<212> TYPE: RNA
<213> ORGANISM: Saccharomyces cerevisiae

<400> SEQUENCE: 124
uaucugguug auccugccag uagucua                                       27

<210> SEQ ID NO 125
<211> LENGTH: 31
<212> TYPE: RNA
<213> ORGANISM: Saccharomyces cerevisiae

<400> SEQUENCE: 125
gucgacguac uucauaggau cauuucuaua g                                  31

<210> SEQ ID NO 126
<211> LENGTH: 10
<212> TYPE: RNA
<213> ORGANISM: Saccharomyces cerevisiae

<400> SEQUENCE: 126
cacucuuuga                                                          10

<210> SEQ ID NO 127
<211> LENGTH: 11
<212> TYPE: RNA
<213> ORGANISM: Saccharomyces cerevisiae

<400> SEQUENCE: 127
ccacugaauc c                                                        11

<210> SEQ ID NO 128
<211> LENGTH: 59
<212> TYPE: RNA
<213> ORGANISM: Artificial Sequence
<220> FEATURE:
<223> OTHER INFORMATION: Delta 4 nt/loop I mutant of U3 snoRNA Domain I

<400> SEQUENCE: 128
aagacuauac uuucagggau cauuucuaua gguccuggug aaaugugcuc gaaaguguc    59
```

METHODS TO SCREEN FOR ANTIBIOTIC AGENTS AND THEIR USE IN TREATMENT OF OPPORTUNISTIC INFECTIONS

RELATED APPLICATION(S)

This application is the continuation of PCT/US01/20520, which designated the United States and was filed on Jun. 28, 2001, published in English, which, in turn, claims priority to U.S. Provisional Application No. 60/215,572, filed Jun. 30, 2000. The entire teachings of the above application(s) are incorporated herein by reference.

FIELD OF THE INVENTION

The invention relates, in general, to evaluation of ribonucleic acid (RNA)-interacting therapeutics, for example, antibiotic agents that prevent formation of mature 18S-rRNA and thereby inhibit protein synthesis and cell growth.

BACKGROUND OF THE INVENTION

An individual is constantly at risk for chronic infections by a variety of agents such as viruses, bacteria, fungi, protozoa and multicellular parasites. Some of the associated infectious diseases are seriously disabling or even life-threatening. Opportunistic infections caused by eukaryotic organisms such as fungi, protozoa and multicellular parasites present a particular challenge for antibiotic agent development because of the evolutionarily shared cellular processes in all eukaryotic cells including human and other animal cells.

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii, Cryptosporidium* sp. are becoming increasingly significant in the developed countries.

A protozoal infection of great economic importance is coccidiosis, a widespread disease of domesticated animals produced by infections by protozoa of the genus *Eimeria*. Some of the most significant of *Eimeria* species are those in poultry namely *E. tenella, E. acervulina, E. necatrix, E. brunetti* and *E. maxima*. The disease is responsible for high levels of morbidity and mortality in poultry and can result in extreme economic losses. In some protozoal diseases, such as Chagas disease, there is no satisfactory treatment; in others, drug-resistant strains of the protozoa may develop.

In addition to parasitic protozoa infections, there exist a myriad of opportunistic mycotic infections caused by such agents as *Cryptococcus* spp., *Candida* spp., *Aspergillus* spp., *Histoplasma* spp., *Coccidioides* spp., *Paracoccidioides* spp. *Blastomyces* spp., *Fusarium* spp., *Sporothrix* spp., *Trichosporon* spp., *Rhizopus* spp., *Pseudallescheria* spp., dermatophytes, *Paeciliomyces* spp., *Alternaria* spp., *Curvularia* spp., *Exophiala* spp., *Wangiella* spp., *Penicillium* spp., *Saccharomyces* spp., *Dematiaceous fungi* and *Pneumocystis carinii*. Many of the present treatments cause severe side effects and some of the currently available antibiotic agents are only fungistatic.

Accordingly, there exists a continued need to identify new and effective antibiotic or antipathogenic drugs. However, antibiotic drug discovery has been, for the most part, a random and laborious process through biological screening of natural products and synthetic compounds against a panel of parasites or fungi. This process can be greatly facilitated and made more specific if a target of antibiotic agents can be identified, and incorporated into a screening process for antibiotic agents. There is a need in the art for new drug targets to identify novel, effective antibiotic agents. Once such agents are identified, treatment of opportunistic infections may be achieved.

SUMMARY OF THE INVENTION

The present invention provides a novel target for antibiotic agents and methods for identification of such antibiotic agents and use of the identified antibiotic agents in treatment of opportunistic infections in eukaryotic hosts. The invention is based upon the identification of species specific 5' hinge and 3' hinge regions of U3 small nucleolar ribonucleic acid (snoRNA). The present invention discloses that the external transcribed spacer (ETS) of the ribosomal RNA precursor (pre-rRNA) comprises sequences that are complementary to the 5' and 3' hinge regions of U3 snoRNA. The invention further discloses that sequence substitutions of the 5' hinge or 3' hinge region of U3 snoRNA severely compromise or fully inhibit the cleavage events at sites 1 and 2 in rRNA processing necessary to form mature 18S rRNA which is a vital component of the small subunit of ribosomes of all eukaryotes.

In one embodiment, the present invention discloses a method of screening an antibiotic agent by providing a mixture of a first recombinant RNA comprising the 5' and 3' hinge regions of U3 snoRNA and a second recombinant RNA comprising pre-rRNA ETS sequences under conditions that allow binding of the first and the second recombinant RNAs and contacting said mixture with a candidate antibiotic agent under conditions which permit inhibition of said binding wherein inhibition of the binding is indicative of an antibiotic agent.

Another embodiment of the present invention provides for a screening method for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow processing of said second recombinant RNA and contacting said mixture with a candidate antibiotic agent under conditions which permit inhibition of said processing wherein inhibition of the processing is indicative of an antibiotic agent. In one embodiment the living cell is a eukaryotic cell. In another embodiment, the cell grows as single cell suspension. In another embodiment, the cell is a yeast cell. In yet another embodiment, the cell is a *Xenopus* oocyte.

Another embodiment of the invention is a method of screening for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow ribosome synthesis and contacting said mixture with a candidate antibiotic agent under conditions which permit inhibition of said ribosome synthesis wherein inhibition of the ribosome synthesis is indicative of an antibiotic agent. In one embodiment, the living cell is a eukaryotic cell. In another embodiment, the cell grows as single cell suspension. In another embodiment, the cell is a yeast cell. In yet another embodiment, the cell is a *Xenopus* oocyte.

The invention further provides a method of screening for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow protein synthesis and contacting said mixture with a candidate antibiotic agent under conditions which permit inhibition of said protein synthesis wherein inhibition of the protein synthesis is indicative of an antibiotic agent. In one embodiment, the living cell is a eukaryotic cell. In another embodiment, the cell grows as single cell suspension. In another embodiment, the cell is a yeast cell. In yet another embodiment, the cell is a *Xenopus* oocyte.

Another embodiment of the invention is a method of screening for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow growth of said cell and contacting said mixture with a candidate antibiotic agent under conditions which permit inhibition of said cell growth wherein inhibition of the cell growth is indicative of an antibiotic agent. In one embodiment, the living cell is a eukaryotic cell. In another embodiment, the cell grows as single cell suspension. In another embodiment, the cell is a yeast cell. In yet another embodiment, the cell is a *Xenopus* oocyte.

Moreover, the invention provides a method of screening for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow division of said cell and contacting said mixture with a candidate antibiotic agent under conditions which permit inhibition of said cell division wherein inhibition of the cell division is indicative of an antibiotic agent. In one embodiment, the living cell is a eukaryotic cell. In another embodiment, the cell grows as single cell suspension. In another embodiment, the cell is a yeast cell. In yet another embodiment, the cell is a *Xenopus* oocyte.

Further, the invention provides a method of screening for an antibiotic agent comprising the steps of providing in a living cell a mixture of a first recombinant RNA comprising the 5' and 3' hinge regions of U3 snoRNA and a second recombinant RNA comprising pre-rRNA ETS sequences under conditions that allow said cell to live and contacting said mixture with a candidate antibiotic agent under conditions which permit inhibition of cell viability wherein inhibition of the cell viability is indicative of an antibiotic agent. In one embodiment, the living cell is a eukaryotic cell. In another embodiment, the cell grows as single cell suspension. In another embodiment, the cell is a yeast cell. In yet another embodiment, the cell is a *Xenopus* oocyte.

Another embodiment of the invention is a method of inhibiting cell growth comprising contacting the cell with an antibiotic agent under conditions which permit inhibition of pre-rRNA processing wherein said inhibition of processing inhibits cell growth.

Also, another embodiment of the invention is a method of inhibiting cell growth comprising contacting the cell with an antibiotic agent under conditions which permit inhibition of protein synthesis wherein said inhibition of protein synthesis inhibits cell growth.

Another embodiment of the invention is a method of treating an opportunistic infection comprising administering an antibiotic agent to an individual suspect of or infected by a pathogen in an amount sufficient to reduce or prevent said opportunistic infection wherein said antibiotic agent inhibits processing of pre-rRNA of said pathogen.

Another embodiment of the invention is a method of treating an opportunistic infection comprising administering an antibiotic agent to an individual suspect of or infected by a pathogen in an amount sufficient to reduce or prevent said opportunistic infection wherein said antibiotic agent inhibits protein synthesis of said pathogen.

Another embodiment of the invention is a method of treating an opportunistic infection comprising administering an antibiotic agent to an individual suspect of or infected by a pathogen in an amount sufficient to reduce or prevent said opportunistic infection wherein said antibiotic agent inhibits cell growth of said pathogen.

Another embodiment of the invention is a method of treating an opportunistic infection comprising administering an antibiotic agent to an individual suspect of or infected by a pathogen in an amount sufficient to reduce or prevent said opportunistic infection wherein said antibiotic agent inhibits cell division of said pathogen thereby inhibiting the increase of the cell number of said pathogen.

Another embodiment of the invention is method of treating an opportunistic infection comprising administering an antibiotic agent to an individual suspect of or infected by a pathogen in an amount sufficient to reduce or prevent said opportunistic infection wherein said antibiotic agent inhibits protein synthesis of said pathogen.

Yet another embodiment of the invention is method of treating an opportunistic infection comprising administering an antibiotic agent to an individual suspect of or infected by a pathogen in an amount sufficient to reduce or prevent said opportunistic infection wherein said antibiotic agent promotes cell death of said pathogen.

Definitions "Antibiotic agent" is equal to antipathogenic agent and means any recombinant, modified or natural nucleic acid molecule; library of recombinant, modified or natural nucleic acid molecules; recombinant, modified or natural polypeptide molecule; library of recombinant, modified or natural polypeptide molecule; organic or inorganic compound; library of organic or inorganic compounds where the agent has the capacity to inhibit binding between a recombinant ribonucleic acid (RNA) comprising 5' and 3' hinge regions of domain I of U3 small nucleolar RNA (snoRNA) and a recombinant RNA comprising the external transcribed spacer sequences (ETS) of the ribosomal RNA precursor (pre-rRNA) by binding to one or both of the 5' or 3' hinge regions of the recombinant RNA comprising the 5' and 3' hinge regions of domain I of U3 snoRNA; by binding to one of the complementary sequences of 5' or 3' hinge regions or both in recombinant RNA comprising the ETS of the pre-rRNA; or by cleavage of 5' or 3' hinge regions or both 5' and 3' hinge regions of U3 snoRNA or the complementary sequences of 5' or 3' hinge regions or both in recombinant RNA comprising the ETS of the pre-rRNA. Preferably, the cleavage of or the inhibition of binding of the sequences will also result in inhibiting processing of functional 18S rRNA, and may also thereby inhibit ribosome synthesis and consequently also inhibit protein synthesis, and may additionally result in inhibiting cell growth, cell division, or viability of the pathogen.

"Recombinant RNA" means natural or synthetic oligoribonucleic acid sequence.

"Domain I of U3 snoRNA" means a recombinant RNA comprising at least (1) the 3' and 5' hinge regions and boxes A and A'; (2) said regions and boxes having a linear order from 5' to 3' direction: A', A, 5'-hinge and 3' hinge; and (3) the nucleotide distance in between the hinge regions and the boxes being sufficient to permit formation of a structure which results in (a) binding of the U3 snoRNA 5' hinge and 3' hinge regions to complementary sequences in the ETS of pre-rRNA and of binding of box A' and box A of U3 snoRNA to complementary regions in the 18S coding portion of the pre-rRNA and (b) in unbound form allows formation of a secondary structure wherein boxes A' and A form a double stranded hairpin structure and the 5' and 3' hinge regions are single-stranded.

"3' hinge" region means a species specific sequence in the domain I of U3 snoRNA that is complementary to and necessary for binding of U3 snoRNA to complementary sequences in the ETS region of pre-rRNA during the process of pre-rRNA cleavage into mature 18S rRNA and is located between the 5' hinge region and domain II of U3 snoRNA, and is in single stranded form when U3 snoRNA is not bound to pre-rRNA.

"Domain II of U3 snoRNA" means the RNA region of U3 snoRNA comprising some combination of or all of the boxes C', B, C and D and the regions in between, in order from 5' to 3' direction.

"5' hinge" region means a species specific sequence of recombinant domain I of U3 snoRNA that is complementary to and important for binding of U3 snoRNA to the complementary sequences in the ETS region of the pre-rRNA during the process of pre-rRNA cleavage into mature 18S rRNA and is located between the 5' hinge region and domain II of U3 snoRNA, and is in single stranded form when U3 snoRNA is not bound to pre-rRNA.

"Box A'" means an evolutionarily conserved sequence within the domain I of U3 snoRNA comprising the sequence 5'-UACUU/C-3' (SEQ ID NO: 1).

"Box A" means an evolutionarily conserved sequence within the domain I of U3 snoRNA comprising the sequence 5'-G G/A AUCN U/G UU U/C U/A U/A U/G A G/T-3' (SEQ ID NO: 2).

"Pre-rRNA" means a sequence comprising the precursor ribosomal RNA or intermediates thereof during rRNA processing leading to formation of mature 18S rRNA, and comprising at least (1) the ETS; (2) 18S rRNA coding portion; and (3) the internal transcribed spacer 1 sequence (ITS1). The ETS comprises the sequences that are complementary to the 5' hinge region and 3' hinge region of U3 snoRNA; the 18S rRNA coding portion comprises sequences that are complementary to box A' and box A of U3 snoRNA, and the cleavage sites 1 and 2, or A1 and A2 in lower organisms such as yeast, that define the boundaries of mature 118S rRNA.

"ETS" means the external, transcribed spacer sequence comprising the 5' region of pre-rRNA which is transcribed but removed during pre-rRNA processing so that it is absent in mature rRNA. The ETS sequence comprises sequences that are complementary to the 5' hinge and the 3' hinge regions of U3 snoRNA.

"18S rRNA" as used herein means both the mature rRNA found in the small subunit of the ribosome and the region in pre-rRNA that comprises the sequence of the mature 18S rRNA. 18S rRNA may be smaller than 18S in size, for example, it may be 17S in lower eukaryotic organisms. The 18S rRNA comprises sequences which can bind to box A' and box A of U3 snoRNA when 18S rRNA sequences are still part of pre-rRNA.

"ITS1" means internal transcribed spacer 1 sequence comprising the sequence immediately to the 3' side of 18S rRNA which is present in the pre-rRNA but is removed by processing so that it is absent from the mature 18S rRNA.

"Inhibit" means partial or complete prevention or disruption of binding as defined herein, or of 18S pre-rRNA processing as defined herein, or of protein synthesis. Thus an antibiotic agent that prevents or disrupts binding of the first and second RNAs may completely prevent binding, as defined by 98–100% loss of a band corresponding to a duplex of first and second RNA molecules on a non-reducing gel, such as gel shift assay, or the appearance of 98–100% of the single-stranded (i.e., non-duplex) first and/or second RNAs. An antibiotic agent that partially inhibits binding of the first and second RNA is determined by at least, up to, and including 10%, 15%, 20%, 25%, 40%, 50%, 75%, 98% of loss of a band corresponding to a duplex RNA (i.e. first and second RNA duplex) in a gel-shift assay, or the appearance of at least, up to, and including 10%, 15%, 20%, 25%, 40%, 50%, 75%, 98% of a band corresponding to a single-stranded first or second RNA.

Further, an antibiotic agent that prevents or disrupts processing of the second RNA may completely prevent processing, as defined by 98–100% loss of a band corresponding to the newly cleaved 18S-rRNA that is smaller than the second RNA molecule on a denaturing gel, such as a gel containing urea or formaldehyde. An antibiotic agent that partially inhibits processing of the second RNA is determined by at least, up to, and including 10%, 15%, 20%, 25%, 40%, 50%, 75%, 98% of a band corresponding to the size of the mature, cleaved 18S-rRNA on a denaturing gel.

Further, an antibiotic agent that prevents or disrupts protein synthesis may completely prevent protein synthesis, as defined by 98–100% loss of synthesized labeled protein as analyzed on an SDS-polyacrylamide gel. An antibiotic agent that partially inhibits protein synthesis is determined by at least, up to, and including 10%, 15%, 20%, 25%, 40%, 50%, 75%, 98% of loss of synthesized labeled protein as analyzed on an SDS-polyacrylamide gel or alternatively by an assay of uptake of labeled amino acids into a polypeptide chain that can be precipitated or trapped on a filter.

Further, an antibiotic agent that prevents or disrupts cell growth may completely prevent cell growth as defined by 98–100% retention of the same cell size without an increase in the cell size as observed by light microscopy. An antibiotic agent that partially inhibits cell growth is determined by at least, up to, and including 10%, 15%, 20%, 25%, 40%, 50%, 75%, 98% of the same cell size without an increase in the cell size.

Further, an antibiotic agent that prevents or disrupts cell division due to the inhibition of ribosome production and hence inhibition of protein synthesis may completely prevent cell division as defined by 98–100% retention of the same cell number without an increase in cell number over time as judged by microscopy of the cells. An antibiotic agent that partially inhibits cell division is determined by at least, up to, and including 10%, 15%, 20%, 25%, 40%, 50%, 75%, 98% of the same cell number without an increase in cell number as judged by microscopy of the cells.

Still further, an antibiotic agent that prevents or disrupts cell viability due to the inhibition of ribosome production and hence inhibition of protein synthesis may completely prevent cell viability as defined by 98–100% cell death as indicated by incorporation of Trypan Blue into the cells in a cell culture analyzed under microscope. An antibiotic agent that partially inhibits cell viability is determined by at least, up to, and including 10%, 15%, 20%, 25%, 40%, 50%, 75%, 98% of the loss of viability of the cell in a cell culture as indicated by increase of Trypan Blue stained cells.

"Cell" as used herein means the smallest structural unit of an eukaryotic organism that is capable of independent functioning, comprising one or more nuclei, cytoplasm, and various organelles that are surrounded by a semi-permeable plasma membrane.

"Binding" as used herein means complementary ribonucleic acid pairing between regions 5' and 3' of the U3 snoRNA and the corresponding nucleic acid sequences in the pre-rRNA ETS.

"Eukaryotic" means an organism whose cells have (1) chromosome or chromosomes and separated from the cytoplasm by a two-membrane nuclear envelope and (2) compartmentalization of a function in distinct cytoplasmic organelles.

"Cell growth" as used herein means growth in the size of a cell at least 10%, preferably 20%, 30%, and 50% up to and including 100% greater than the initial size of the cell immediately after cell division, as judged by microscopy. The analysis can be made manually or photographically by comparing antibiotic agent treated and untreated cells after cell division.

"Single cell" as used herein means cells that are able to grow, divide and live in a suspension in a growth medium without a solid support such as attachment to other cells; secreted extracellular matrix; or plastic surface.

"Ribosome synthesis" as used herein means biological process of assembly of the ribosomal RNAs into a functioning complex comprising 18S rRNA and the ribosomal proteins.

"Protein synthesis" as used herein means translation of genetic information encoded by DNA via messenger RNA (mRNA) into amino acid sequence by ribosomes. For example, protein synthesis can be monitored by transfecting a cell with a plasmid containing the sequences of interest. The cells are then cultured in a medium that induces the transcription and consequent translation of the sequences of interest. The antibiotic agent and labeled amino acids are added into the medium. A parallel cell culture is allowed to grow without candidate antibiotic agent. The newly made proteins are extracted from the two parallel cell cultures and analyzed on sodiumdodecylsulfate-polyacrylamide (SDS-PAGE) gels that are known to one skilled in the art. Up to and including 10%, 15%, 20%, 50%, 75%, and 100% reduction in the amount of incorporated label in the samples treated with candidate antibiotic agent compared to the untreated sample indicates antibiotic properties of the candidate agent.

"Cell division" as used herein means events leading to one cell splitting up into two by the process of mitosis. To assess cell division, cells can be counted, for example, under light microscope in specified time intervals and the division rate or efficiency can be calculated. Comparison between the candidate antibiotic agent treated and untreated cell cultures allows defining the potential reduction in the cell division rate. The reduction of up to and including 10%, 15%, 20%, 50%, 75%, and 100% in the number of cells indicates impairment of cell division.

"Living cell" as used herein means a cell that is capable of growing and/or dividing.

"Viability" as used herein means capability of a cell to live. Cell viability can be assayed by, for example, Trypan Blue dye which is actively excluded from living cells but readily enters and stains dead cells. The staining can be monitored, for example, by light microscopy. Up to and including 10%, 15%, 20%, 50%, 75%, and 100% increase in the number of the stained cells in the candidate antibiotic agent treated sample compared to the untreated control is indicative of reduced cell viability.

"Disruption" means inhibition of binding of the 5' or 3' or both 5' and 3' hinge regions the recombinant U3 snoRNA and the complementary nucleic acid sequences in the pre-rRNA ETS.

"Cleavage site 1" in pre-rRNA means the site in pre-rRNA comprising the sequence between the ETS and the precise 5' end of the 18S rRNA where the U3 snoRNA-dependent cutting of pre-rRNA occurs during the process of mature 18S rRNA production.

"Cleavage site A1" in pre-rRNA means the corresponding U3 snoRNA-dependent cleavage site 1 in the lower eukaryotes.

"Cleavage site 2" in pre-rRNA means the site in pre-rRNA comprising the sequence between the ETS and the precise 3' end of the 18S rRNA where the U3 snoRNA-dependent cutting of pre-rRNA occurs during the process of mature 18S rRNA production.

"Cleavage site A2" in pre-rRNA means the cleavage site 2 within the ITS2 in lower eukaryotes where U3 snoRNA-dependent cleavage occurs to result in mature 18S rRNA.

"Pathogen" means any eukaryotic agent that can cause an opportunistic infection, for example, a microorganism such as yeast or other fungi including but not limited to *Cryptococcus* spp., *Candida* spp., *Aspergillus* spp., *Histoplasma* spp., *Coccidioides* spp., *Paracoccidioides* spp. *Blastomyces* spp., *Fusarium* spp., *Sporothrix* spp., *Trichosporon* spp., *Rhizopus* spp., *Pseudallescheria* spp., dermatophytes, *Paeciliomyces* spp., *Alternaria* spp., *Curvularia* spp., *Exophiala* spp., *Wangiella* spp., *Penicillium* spp., *Saccharomyces* spp., *Dematiaceous fungi* and *Pneumocystis carinii*; *Histoplasma* sp., *Coccidiomycosis* sp., *Sacchromyces* sp., *Actinomycetes* sp. and the like; or protozoa such as *Trypanosoma* or *Leishmania, Neisseria* and the like.

"Eukaryotic host" as used herein means any eukaryotic organism including but not limited to vertebrae; mammals; human; domestic animals, such as bovines, pigs, sheep, horses, cats, and canines; and plants.

"Opportunistic infection" means invasion by a pathogen of a eukaryotic host in which the conditions are favorable for growth, proliferation, and possible toxin production and subsequent injury to the host.

"Processing" means cleavage of pre-rRNA by U3 snoRNA-dependent cleavage at sites 1 or A1 and 2 or A2.

"Sufficient" means that the processing of 18S pre-rRNA in the presence of between an antibiotic agent is at least 5%, 10%, 25%, 50%, 75%, 85% and up to 100% less than processing of pre-rRNA in the absence of the antibiotic agent.

Further features and advantages of the invention will become more fully apparent in the following description of the embodiments and drawings thereof, and from the claims.

A. Pathway A cleavage sites in pre-rRNA of *Xenopus* oocytes to form 18S rRNA; U3 snoRNA is needed for cleavage at sites 1, 2 and 3 (Savino and Gerbi, 1990; Lange et al., 1998; Borovjagin and Gerbi, 1999).

B. Secondary structure of U3 snoRNA showing conserved boxes.

Figure 6:
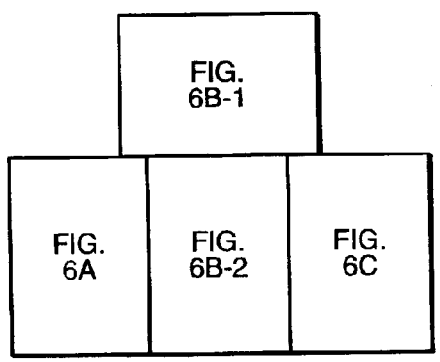
Figure 6A:
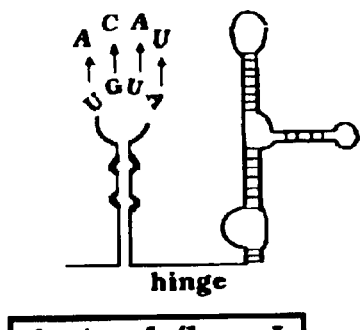
Figure 6A:
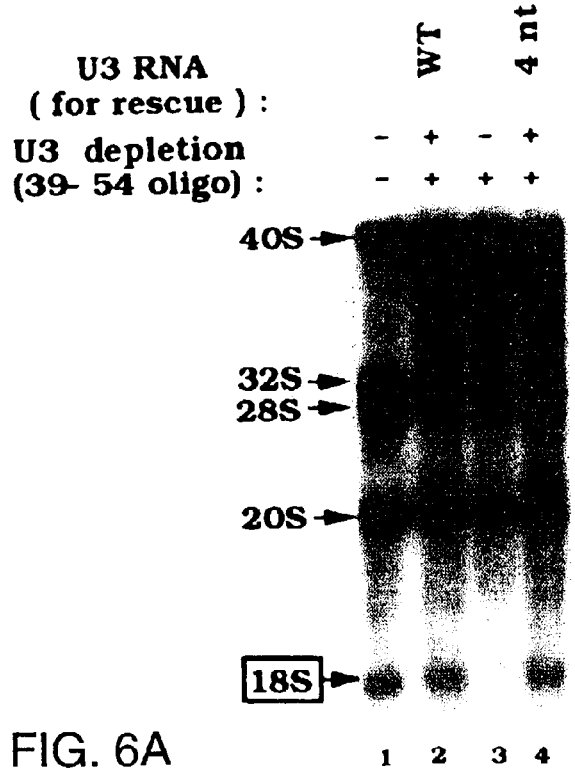
Figures 1, 6B:
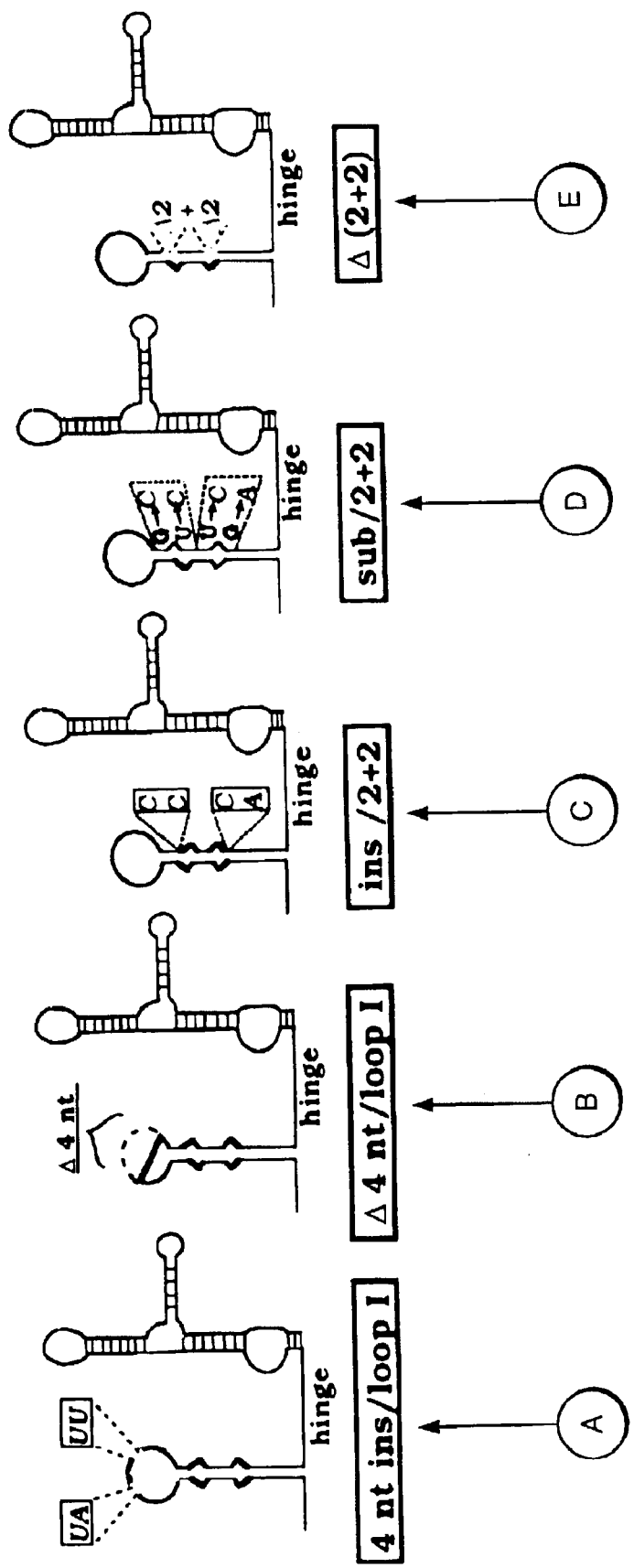
Figures 2, 6B:
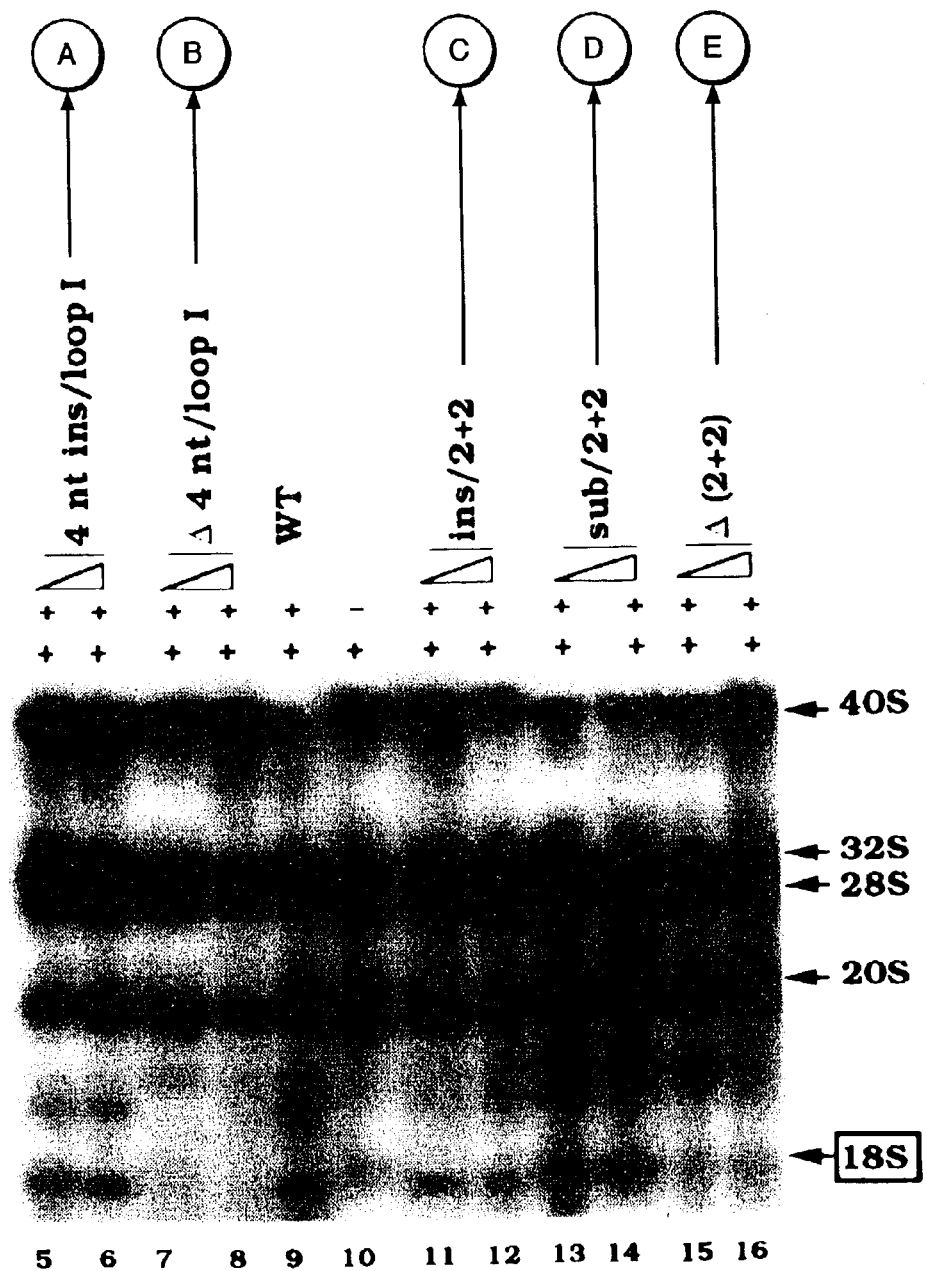
Figure 6C:
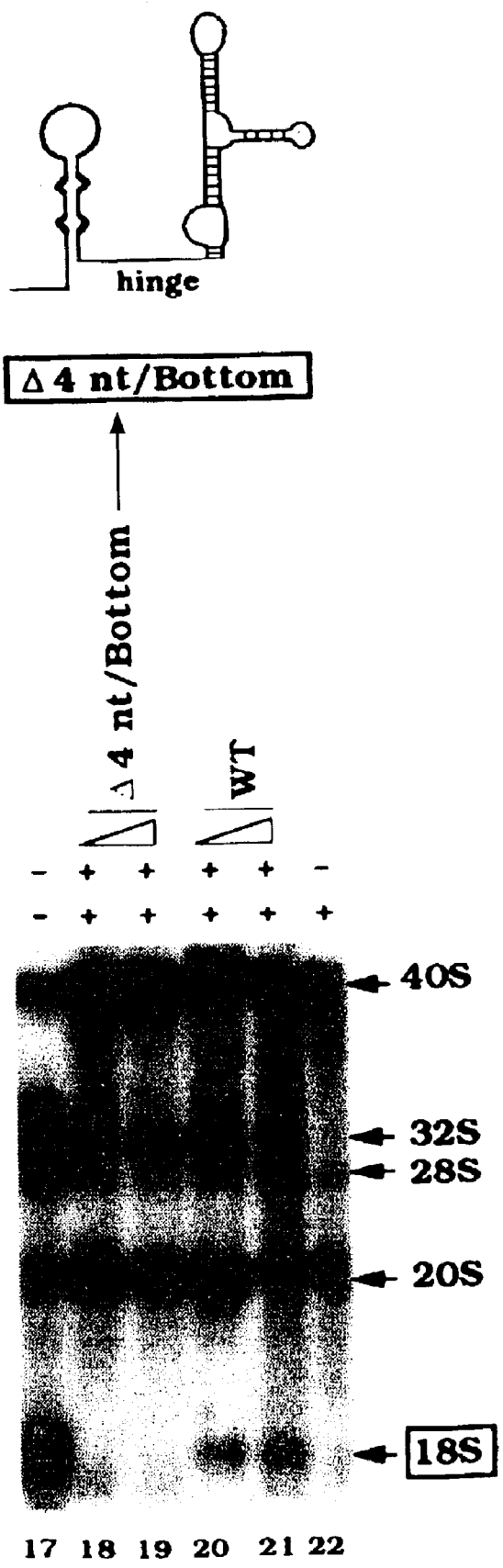
Figure 7A:
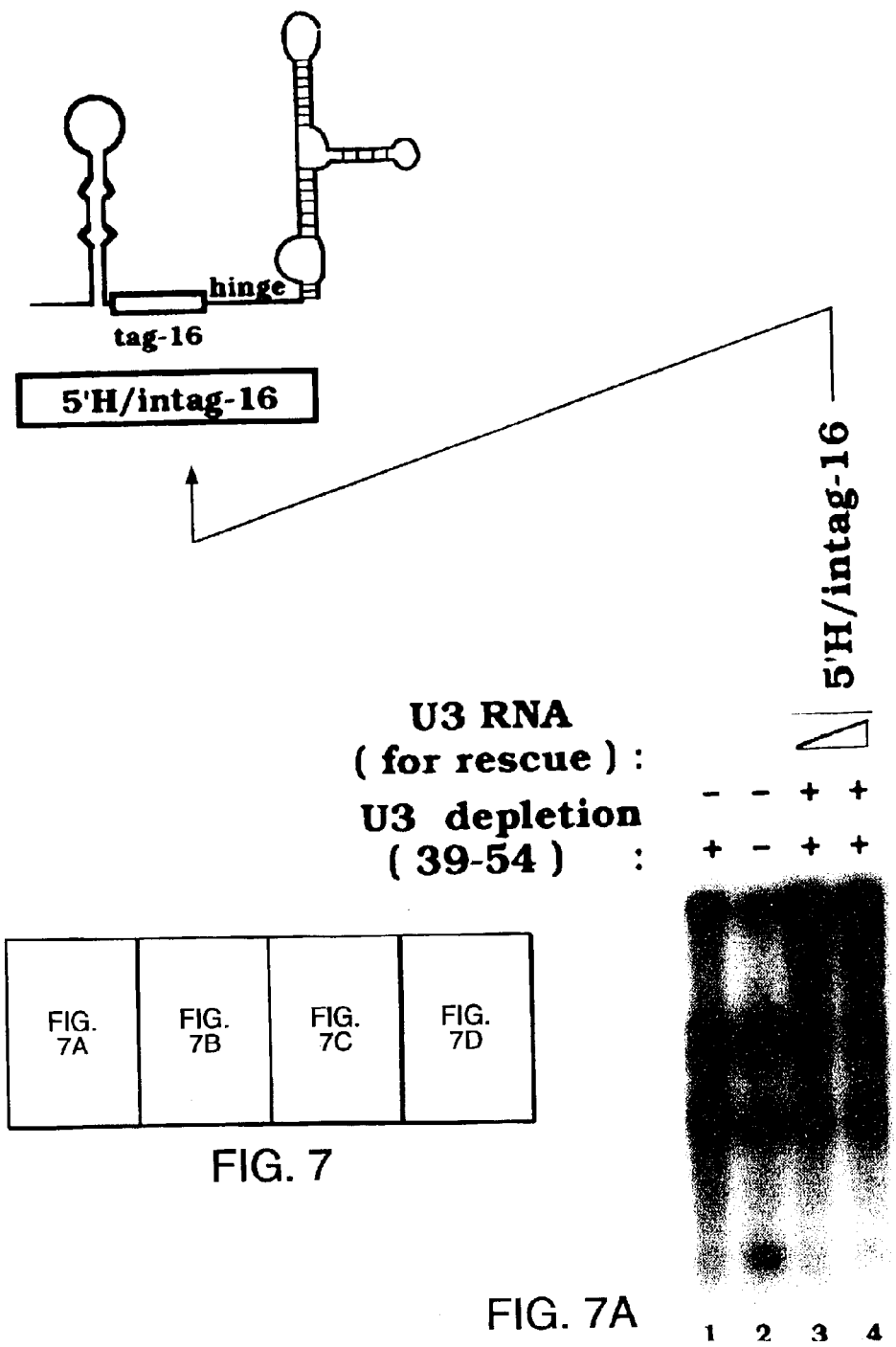
Figure 7B:
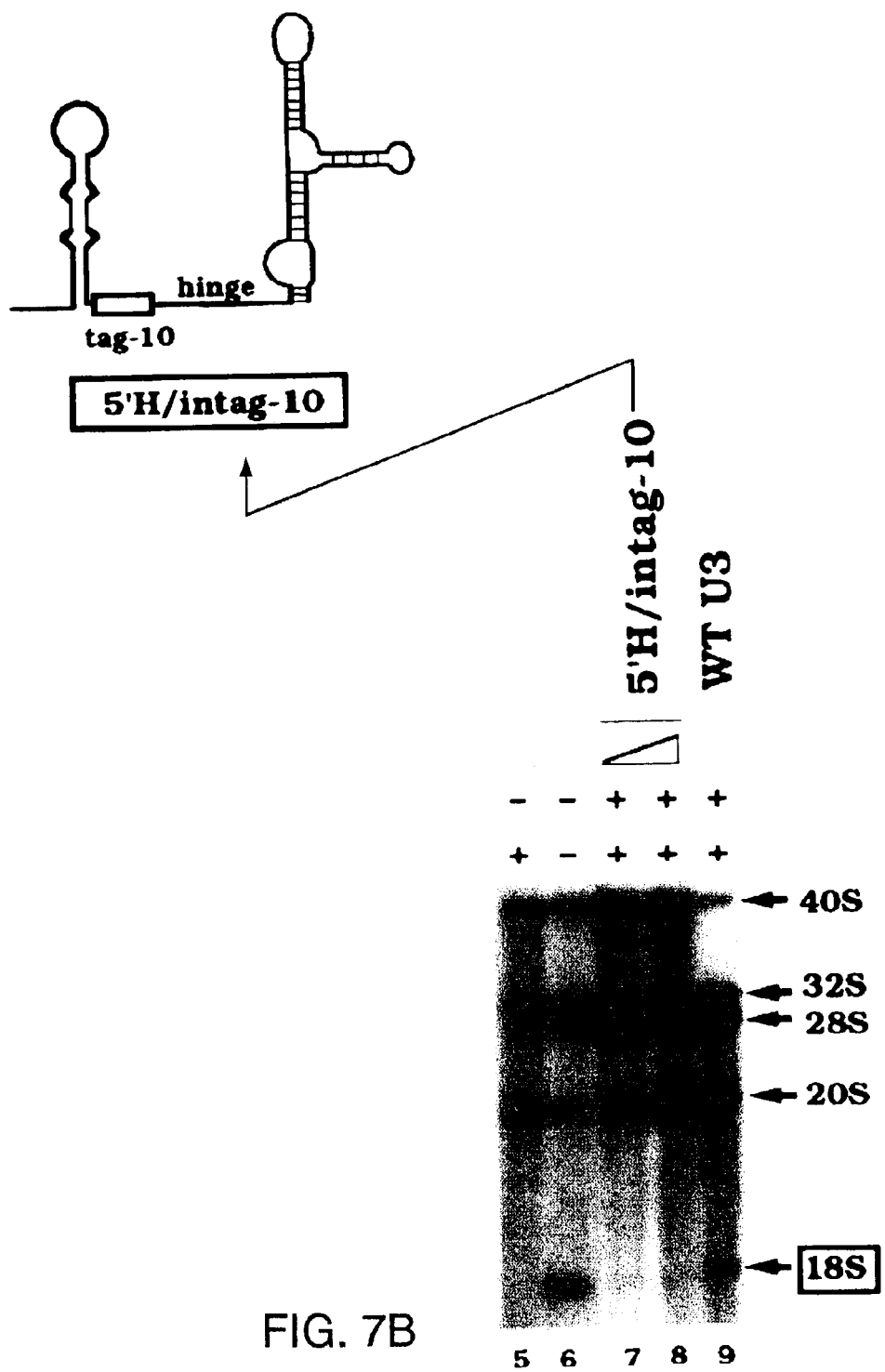
Figure 7C:
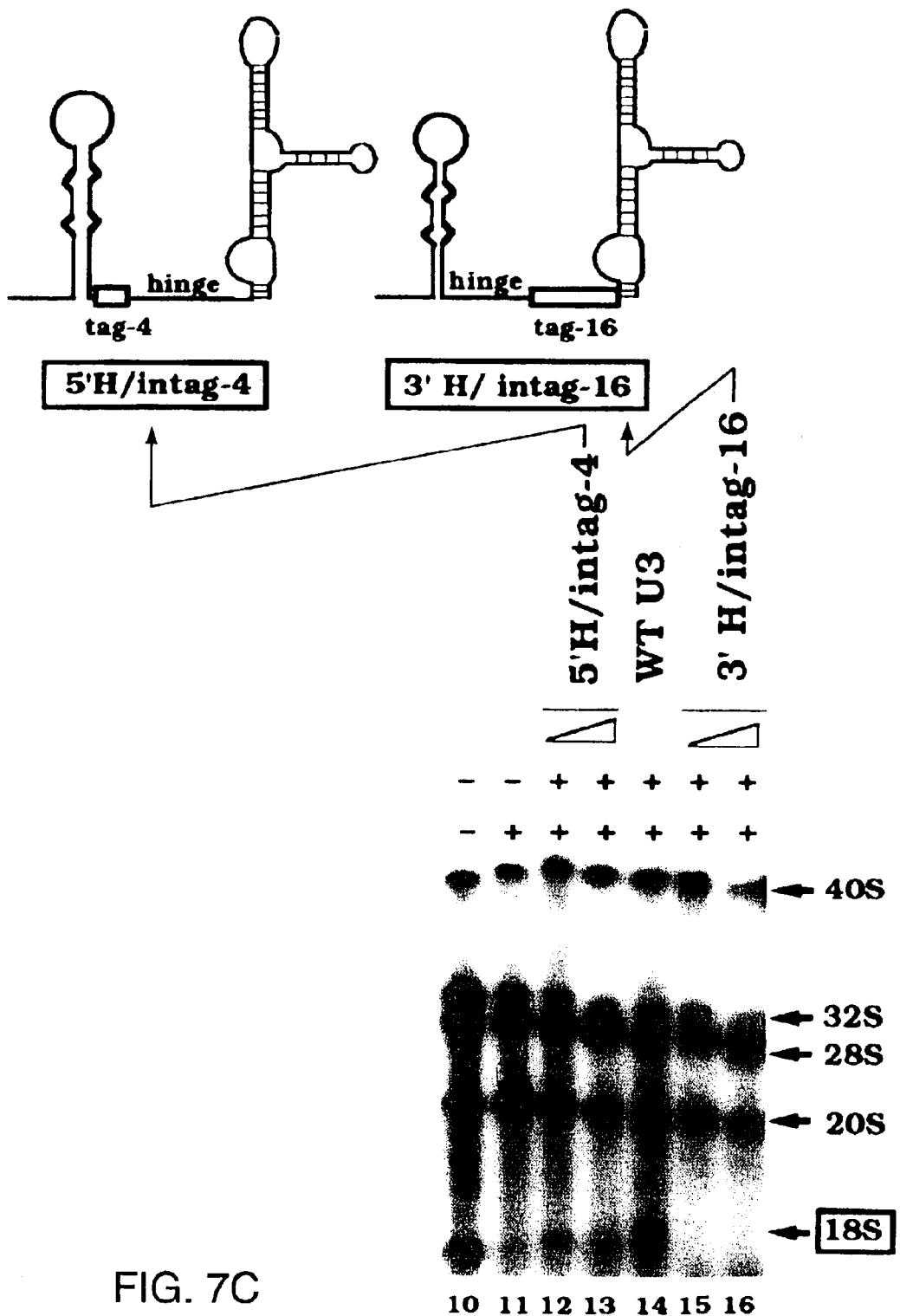
Figure 7D:
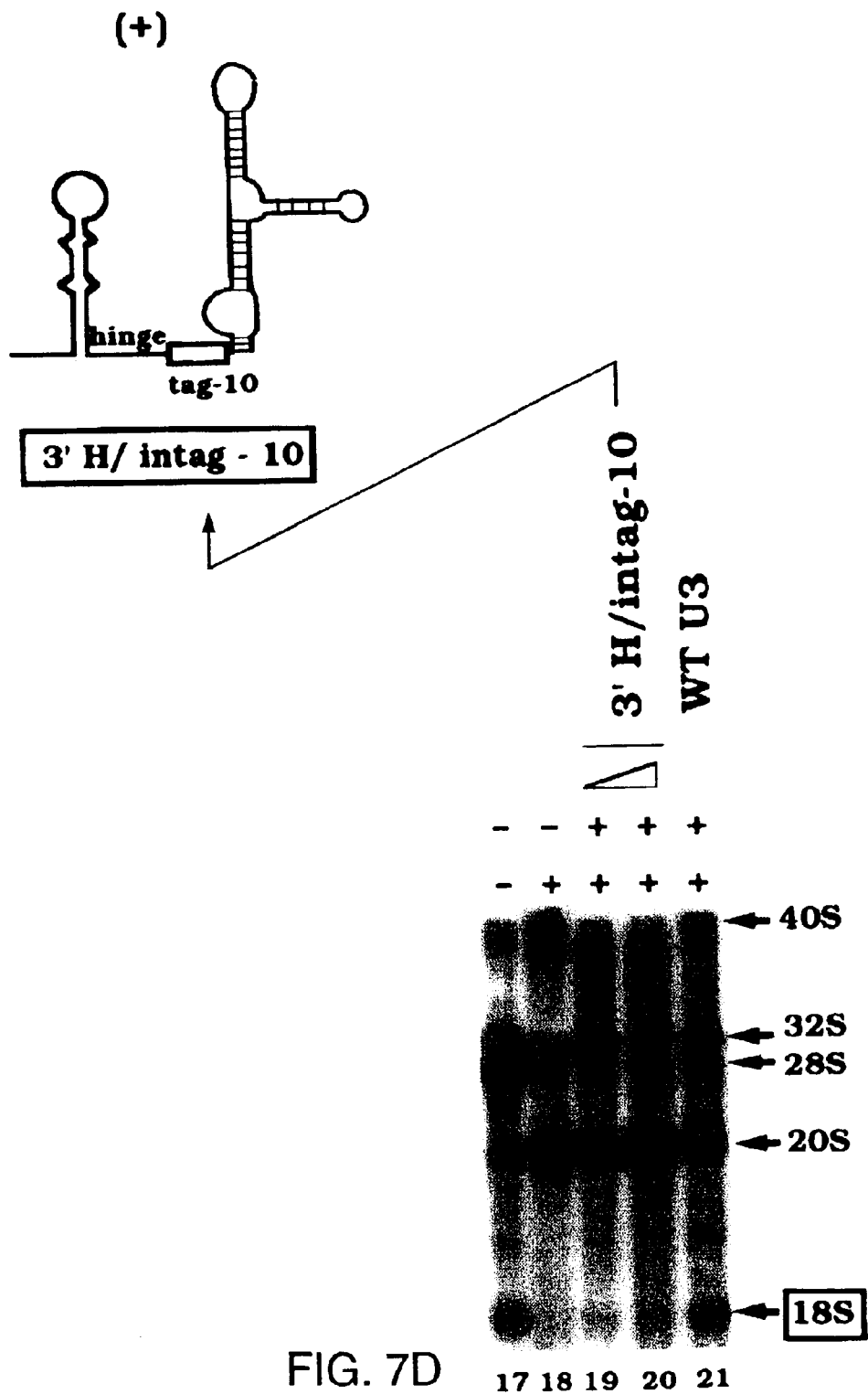

FIG. 2. Mutations of U3 snoRNA.

Figure 2A:
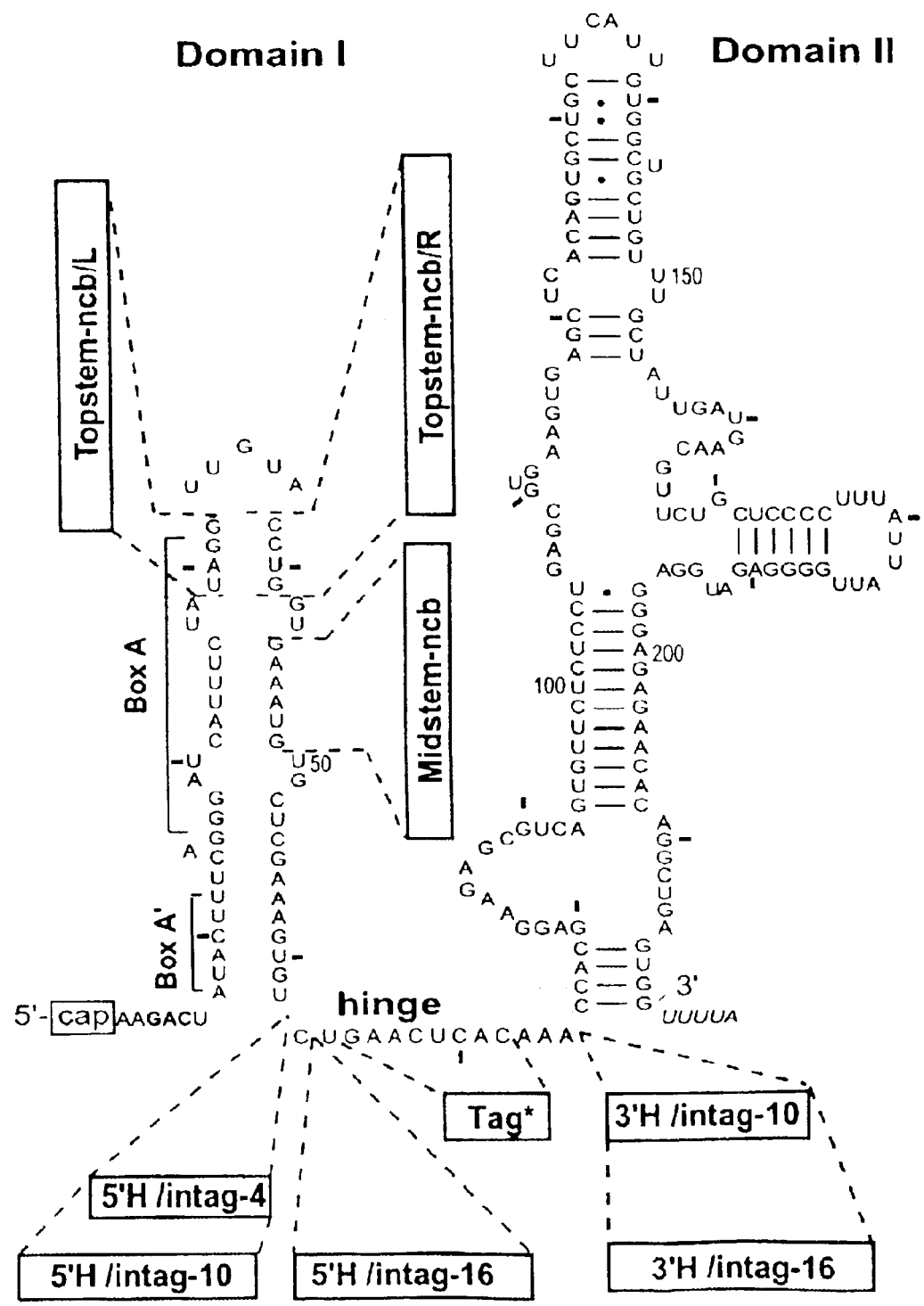
Figure 2B:
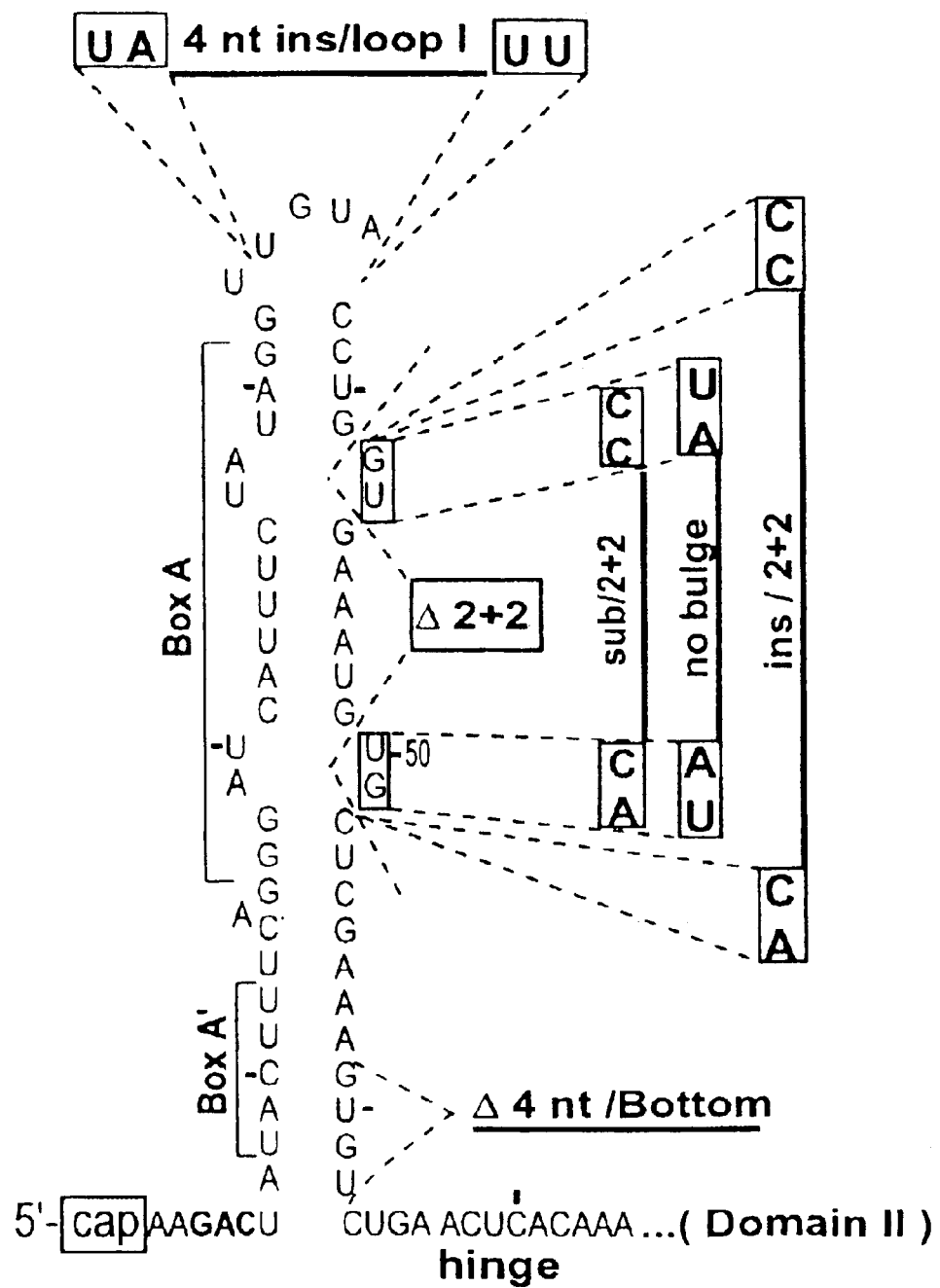
Figure 2C:
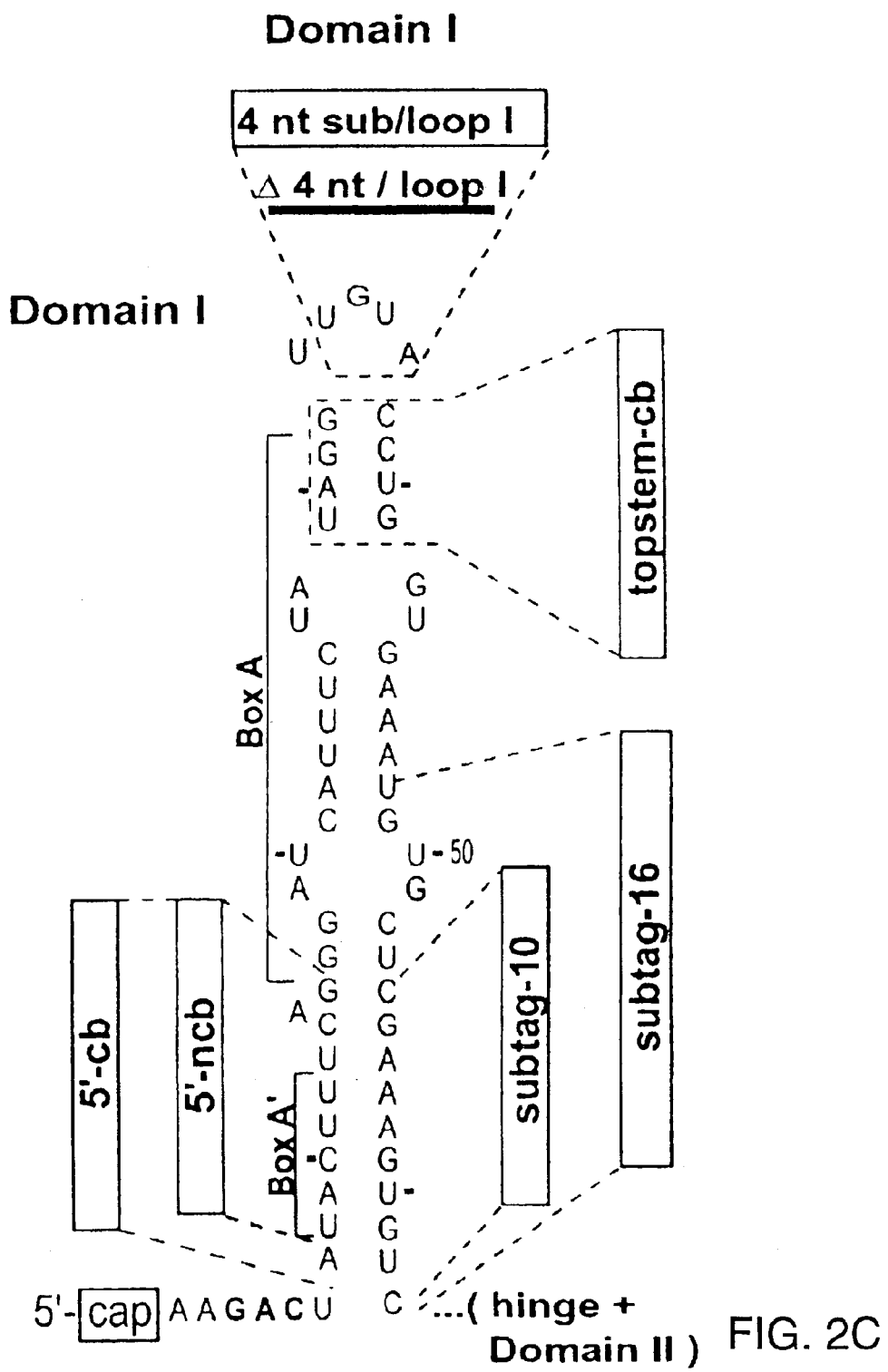

The secondary structure of the entire U3 snoRNA molecule or just domain I is shown in panels A–C, with the sequences of the mutations listed in panel D. U3 snoRNA consists of domain I (5' region), and domain II (3' region). Domain I contains evolutionarily conserved Boxes A' and A (as indicated in the figure); Boxes C', B, C and D in domain II are not indicated here. FIG. 2A shows the entire U3 snoRNA molecule (SEQ ID NO: 55). FIG. 2B shows Domain I of the U3 snoRNA molecule (SEQ ID NO: 56). The 4 nt ins/loop I mutant of SEQ ID NO: 56 is represented by SEQ ID NO: 57. The sub/2+2 mutant of SEQ ID NO: 56 is represented by SEQ ID NO: 58. The no bulge mutant of SEQ ID NO: 56 is represented by SEQ ID NO: 59. The ins/2+2 mutant of SEQ ID NO: 56 is represented by SEQ ID NO: 60. The Δ2+2 mutant of SEQ ID NO: 56 is represented by SEQ ID NO: 61. The Δ4 nt/Bottom mutant of SEQ ID NO: 56 is represented by (SEQ ID NO: 62. FIG. 2C shows Domain I of the U3 snoRNA molecule (SEQ ID NO: 63). The Δ4 nt/loop I mutant of SEQ ID NO: 63 is represented by SEQ ID NO: 128. Panel D also summarizes the effect of each U3 mutation to restore 18S rRNA production after disruption of endogenous U3 snoRNA: ++ indicates full rescue, + is partial rescue, (+) weak rescue and − is no rescue of 18S rRNA formation. Tag* is represented by SEQ ID NO: 65. The Tag* mutant of SEQ ID NO: 64 is represented by SEQ ID NO: 68. 3'H/intag-10 is represented by SEQ ID NO: 66. The 3'H/intag-10 mutant of SEQ ID NO: 64 is represented by SEQ ID NO: 70. 3'H/intag-16 is represented by SEQ ID NO: 67. The 3'H/intag-16 mutant of SEQ ID NO: 64 is represented by SEQ ID NO: 69. 5'H/intag-10 is represented by SEQ ID NO: 72. The 5'H/intag-10 mutant of SEQ ID NO: 70 is represented by SEQ ID NO: 75. 5'H/intag-4 is represented by SEQ ID NO: 73. The 5'H/intag-4 mutant of SEQ ID NO: 70 is represented by SEQ ID NO: 76. 5'H/intag-16 is represented by SEQ ID NO: 74. The 5'H/intag-16 mutant of SEQ ID NO: 70 is represented by SEQ ID NO: 74. Topstem-ncb/L is represented by SEQ ID NO: 79. The Topstem-ncb/L mutant of SEQ ID NO: 78 is represented by SEQ ID NO: 80. Topstem-ncb/R is represented by SEQ ID NO: 82. The Topstem-ncb/R mutant of SEQ ID NO: 81 is represented by SEQ ID NO: 83. Midstem-ncb is represented by SEQ ID NO: 85. The Midstem-ncb mutant of SEQ ID NO: 84 is represented by SEQ ID NO: 86. The 4 nt ins/loop I mutant of SEQ ID NO: 87 is represented by SEQ ID NO: 88. The sub/2+2 mutant of SEQ ID NO: 89 is represented by SEQ ID NO: 90. The no bulge mutant of SEQ ID NO: 89 is represented by SEQ ID NO: 91. The ins/2+2 mutant of SEQ ID NO: 89 is represented by SEQ ID NO: 92. The Δ2+2 of SEQ ID NO: 89 is represented by SEQ ID NO: 93. The Δ4 nt/Bottom mutant of SEQ ID NO: 94 is represented by SEQ ID NO: 95. Subtag-10 is represented by SEQ ID NO: 98. The subtag-10 mutant of SEQ ID NO: 96 is represented by SEQ ID NO: 100. Subtag-16 is represented by SEQ ID NO: 97. The subtag-16 mutant of SEQ ID NO: 96 is represented by SEQ ID NO: 99. The 4 nt sub/loop I mutant of SEQ ID NO: 101 is represented by SEQ ID NO: 103. The Δ4 nt/loop I mutant of SEQ ID NO: 104 is represented by SEQ ID NO: 105. 5'-ncb is represented by SEQ ID NO: 107. The 5'-ncb mutant of of SEQ ID NO: 106 is represented by SEQ ID NO: 109. 5'-cb is represented by SEQ ID NO: 108. The 5'-ncb mutant of SEQ ID NO: 106 is represented by SEQ ID NO: 110. The Topstem-cb mutant of SEQ ID NO: 111 is represented by SEQ ID NO: 112.

Figure 3:
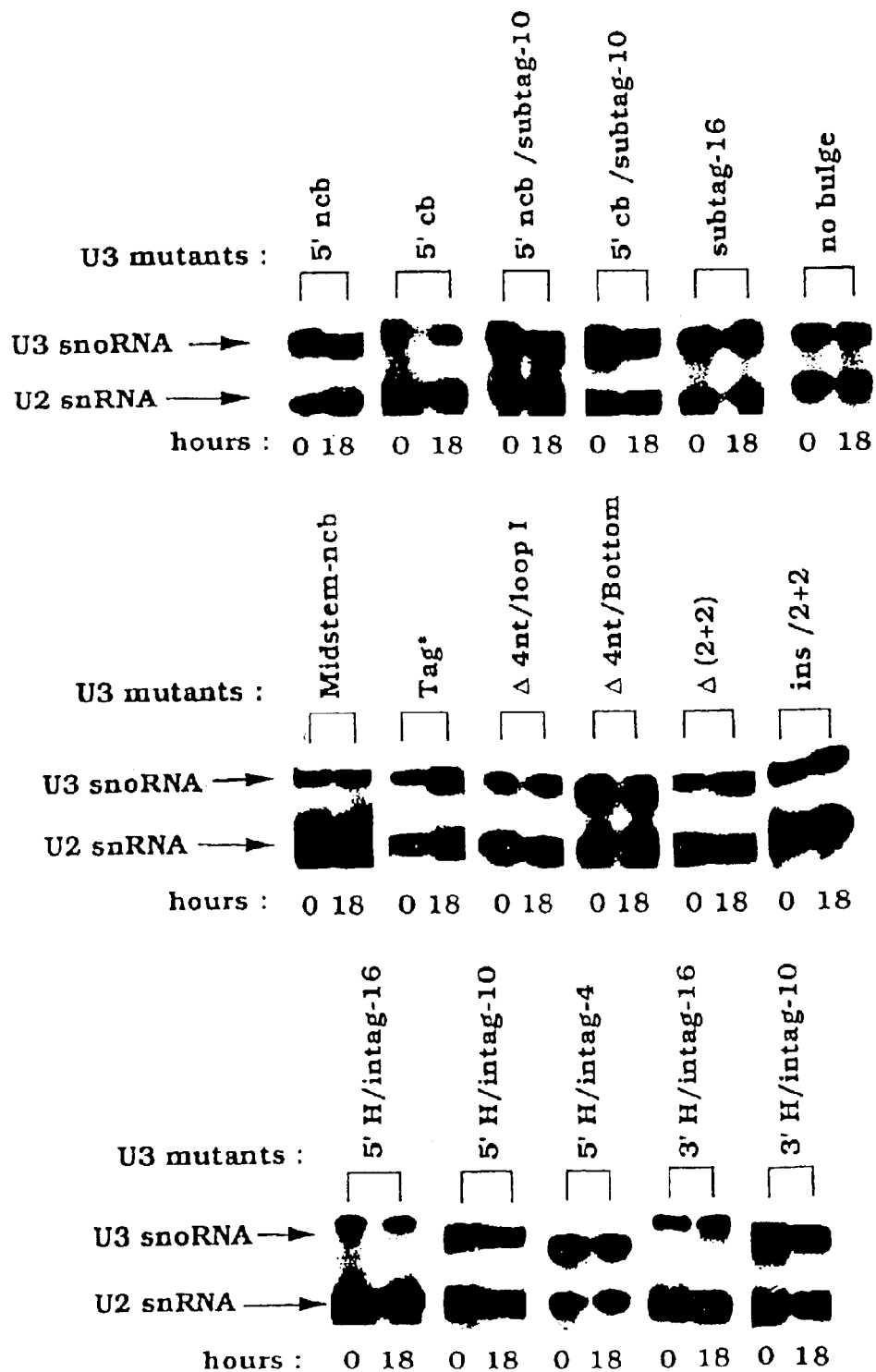

FIG. 3. Stability of U3 snoRNA mutants.

$^{32}$P-labelled in vitro transcripts of capped, U3 snoRNA mutants were injected into *Xenopus* oocyte nuclei together with $^{32}$P-labelled in vitro transcripts of U2 snRNA as an internal control. Zero and eighteen hours after injection, the nuclear RNA was isolated and analyzed by acrylamide gel electrophoresis. U3 snoRNA mutants that were functional in rescuing 18S rRNA processing clearly must have been stable and are not shown here.

Figure 4A:
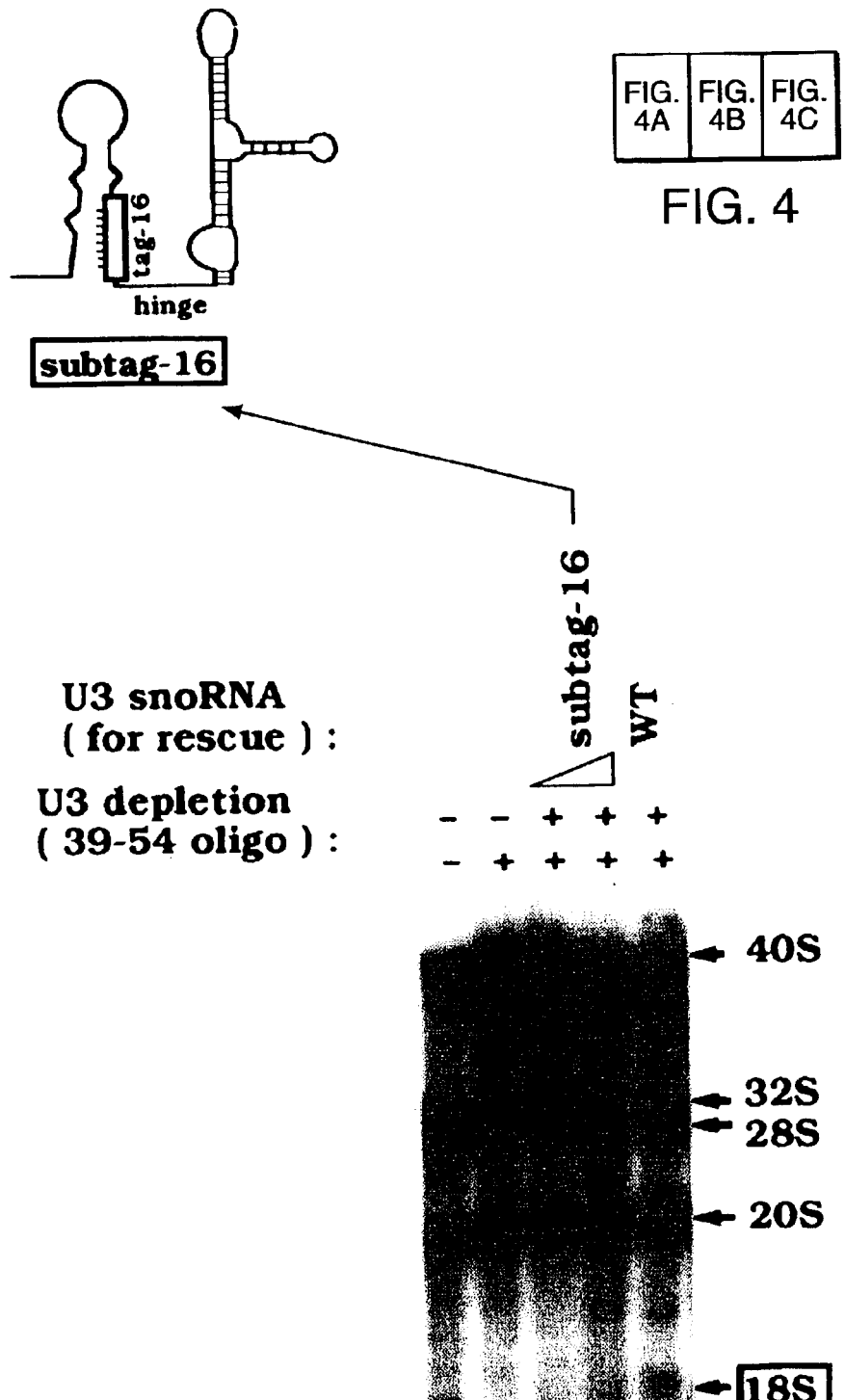
Figure 4B:
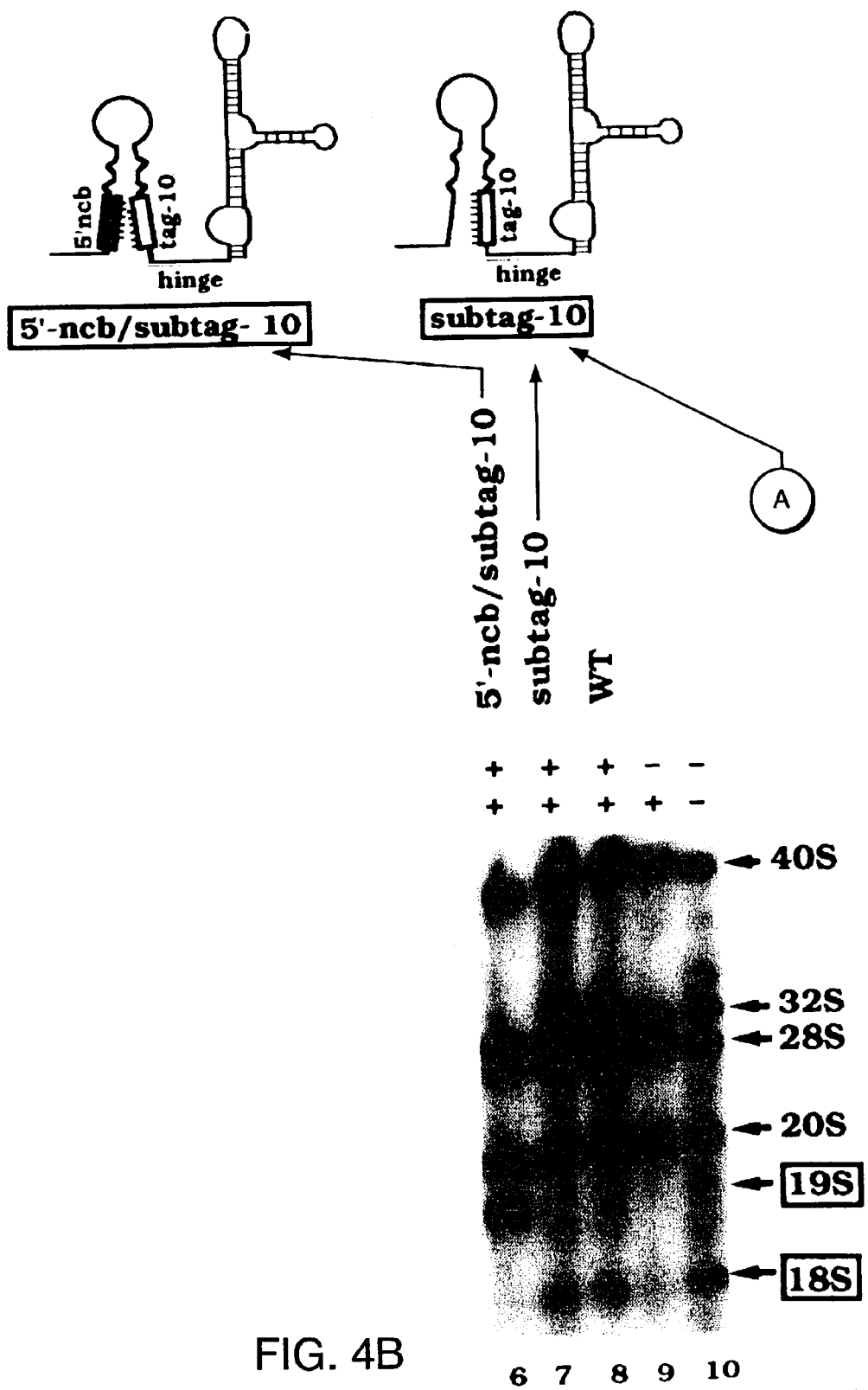
Figure 4C:
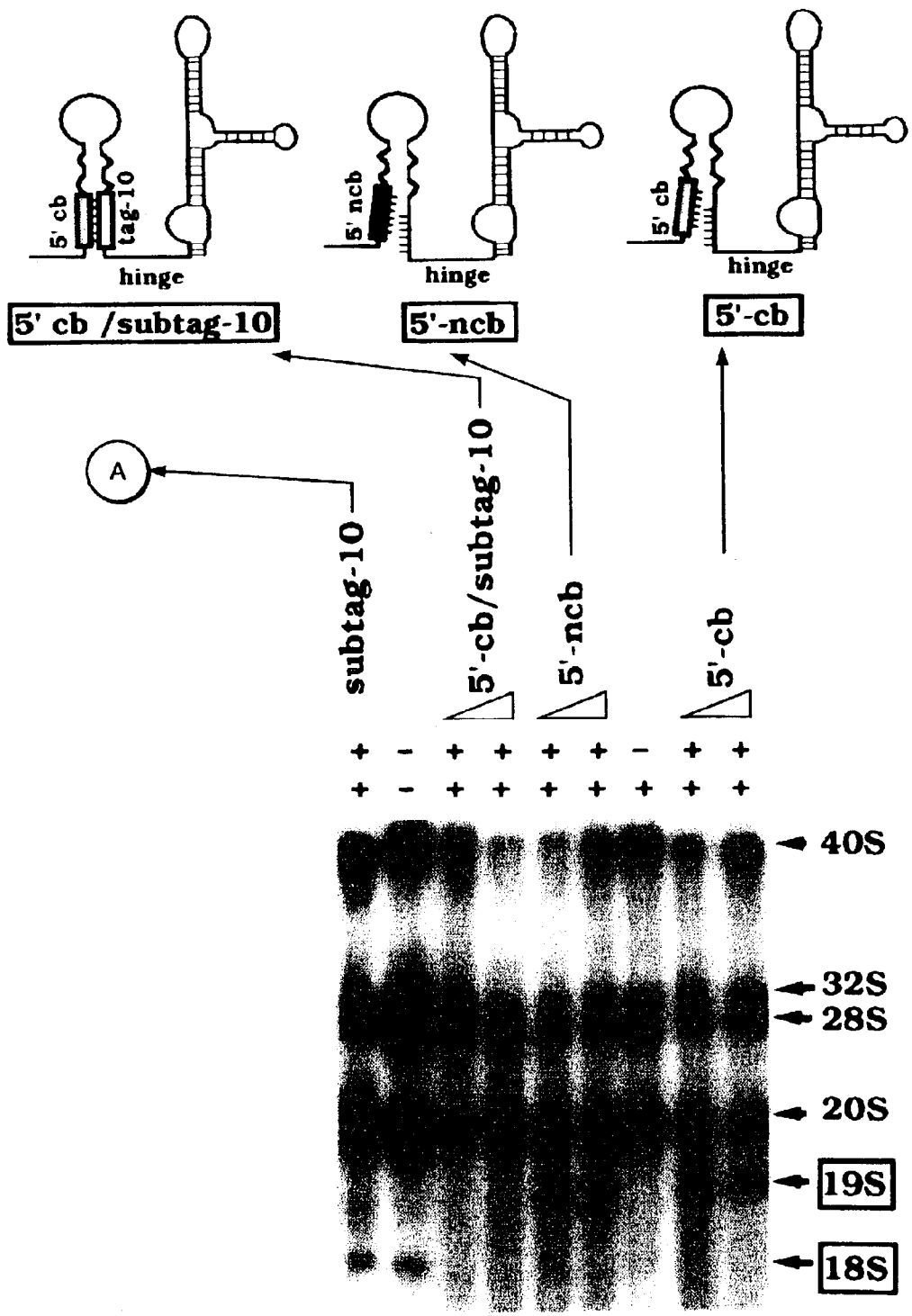

FIG. 4. U3 snoRNA function in 18S rRNA processing requires that the base of the putative stem of domain I remains single stranded and contains the sequences of Box A'.

Agarose gel electrophoresis of in vivo labelled pre-rRNA and rRNA from nuclei of *Xenopus* oocytes after no treatment (positive control), depletion of intact endogenous U3 snoRNA by two sequential injections of an antisense oligonucleotide complementary to nt 39–54 without (negative control) or after U3 depletion with subsequent injection of in vitro synthesized snoRNA.

Figure 5A:
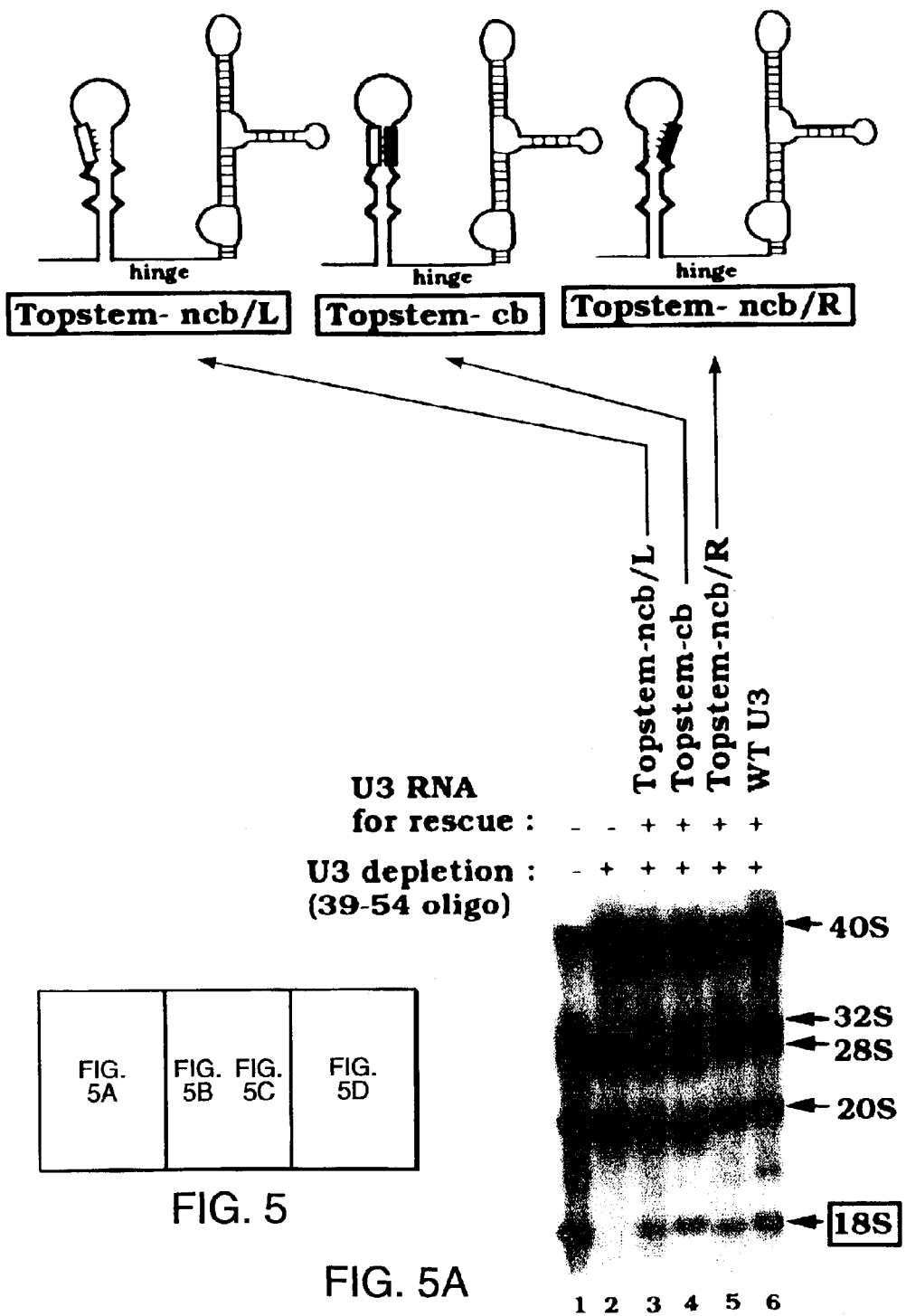
Figure 5D:
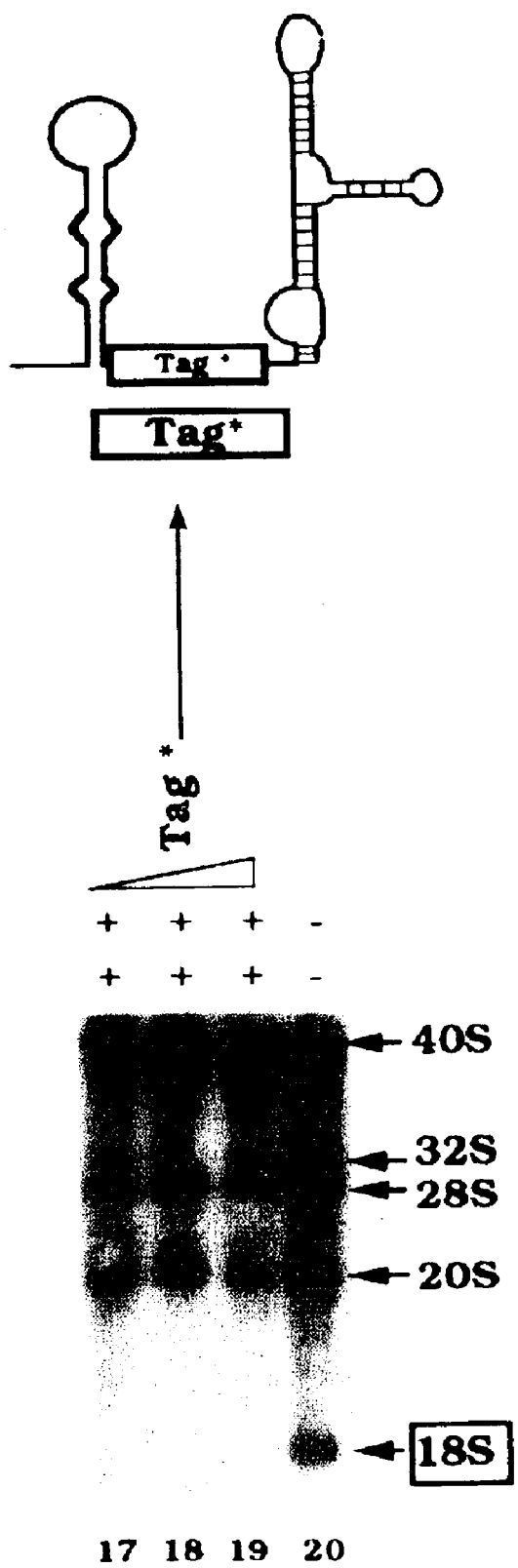

FIG. 5. Base-pairing at the top of the putative stem of domain I is not required but the 5' hinge and 3' hinge are important for U3 snoRNA function in 18S rRNA processing.

The sequence mutated in Topstem-ncb/L is indicated by an unshaded box, and that mutated in Topstem-ncb/R is shown by a shaded box; these mutations open up the top of the putative stem of domain I. Both mutations are present in the double mutant Topstem-cb, and restore the potential to base-pair because the wild type sequence on the left and right sides at the top of the putative stem have simply been swapped.

FIG. 6. The distance between elements in U3 domain I and the rest of the molecule is critical for 18S rRNA processing.

U3 snoRNA mutants were tested that decreased (Δ) or increased (ins) the distance between Boxes A'+A and the hinge region.

FIG. 7. The spacing between U3 domain I and domain II is critical for 18S rRNA processing.

U3 snoRNA mutants containing insertions directly upstream (5'H) or downstream (3'H) of the hinge region (renamed the "3' hinge") were tested for their ability to restore 18S rRNA processing after anti-sense oligonucleotide destruction of intact endogenous U3 snoRNA (as in FIG. 4).

Figures 2, 8A:
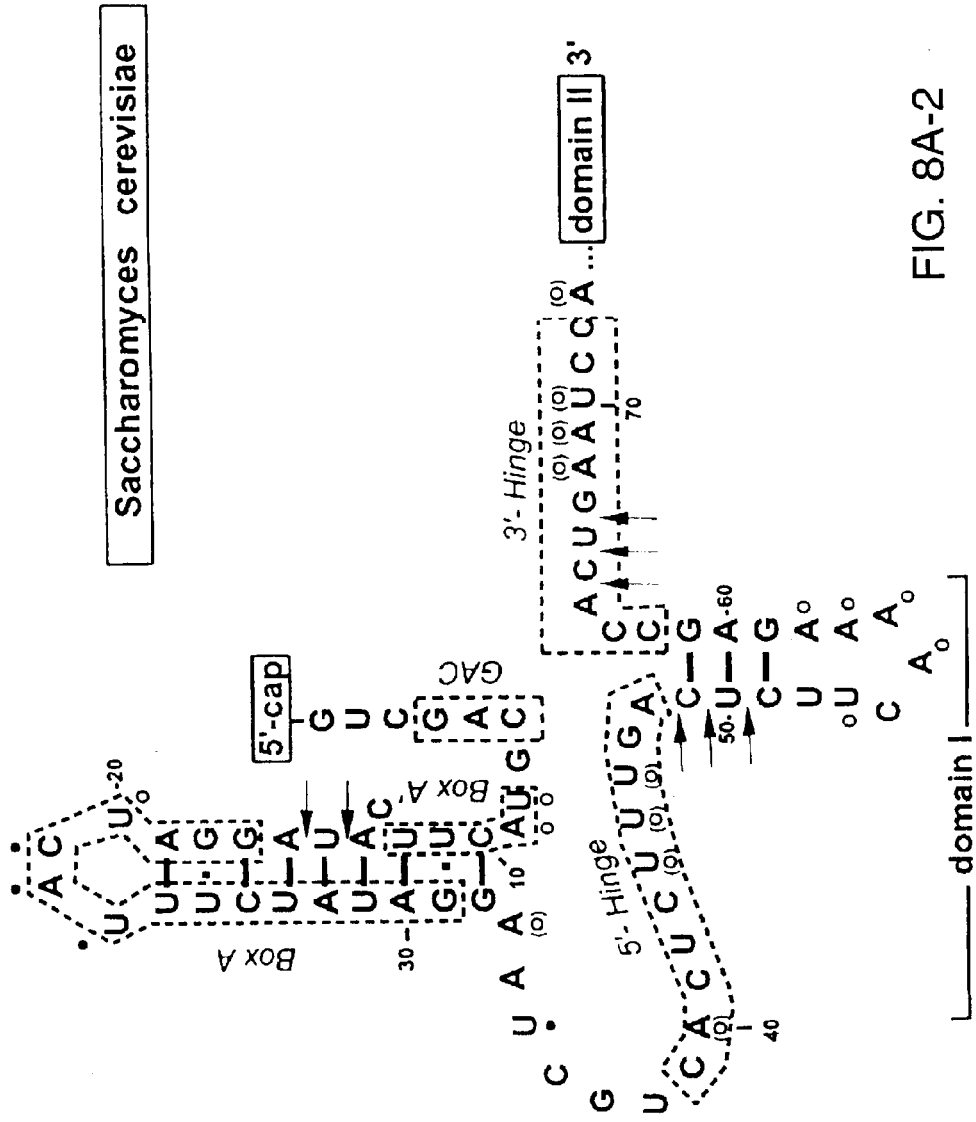

FIG. 8. Structure of U3 snoRNA in its unbound and bound forms.

(A). Postulated structure of domain I of U3 snoRNA when it is unbound in the nucleolus.

FIG. 8A-1 (SEQ ID NO: 113)
FIG. 8A-2 (SEQ ID NO: 114)

(B). Postulated base-pairing between U3 snoRNA and pre-rRNA.

Figures 1, 2D:
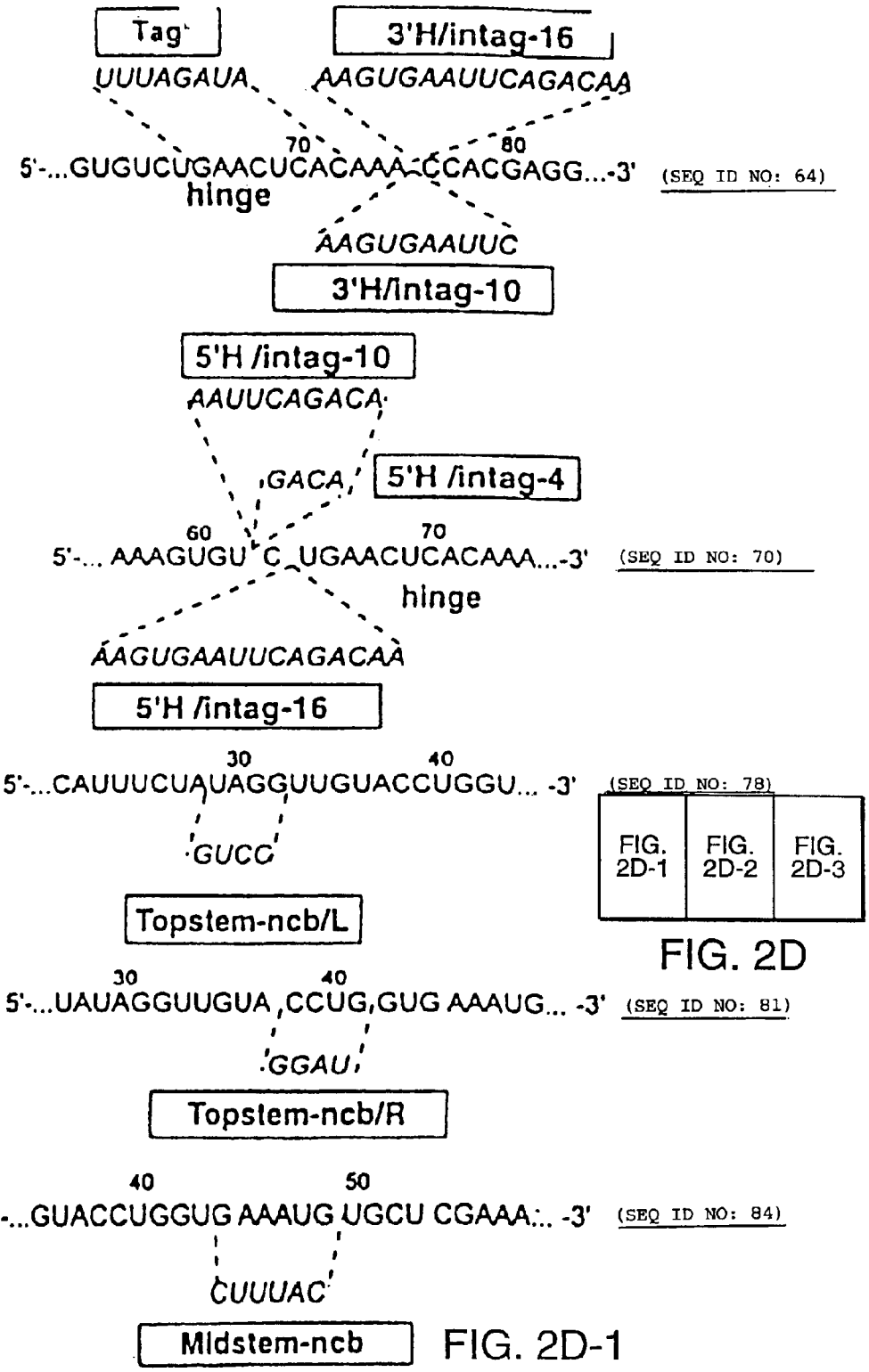
Figures 2, 8B:
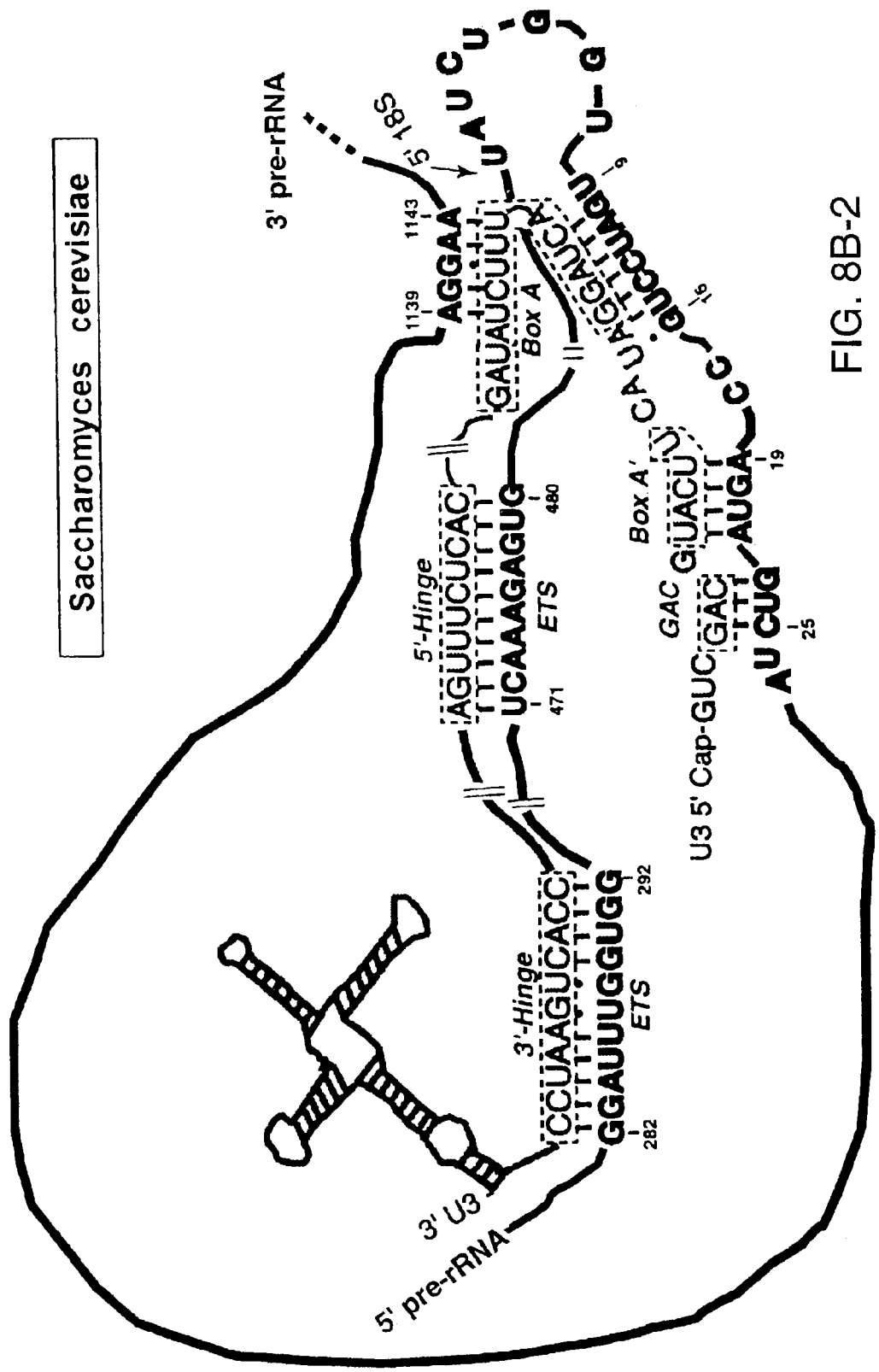

FIG. 8B-1:
5' pre-rRNA: ETS 311–381 (SEQ ID NO: 115)
   ETS 441–449 (SEQ ID NO: 116)
   5' 18S 1–27 (SEQ ID NO: 117)
   1158–1162 (SEQ ID NO: 118)
U3: 1–31 including GAC, Box A' and Box A (SEQ ID NO: 119)
   5'-Hinge (SEQ ID NO: 120)
   3'-Hinge (SEQ ID NO: 121)

FIG. 8B-2:
5' pre-rRNA: ETS 282–292 (SEQ ID NO: 122)
   ETS 471–480 (SEQ ID NO: 123)
   5' 18S 1–27 (SEQ ID NO: 124)
   1139–1143 (SEQ ID NO: 118)

U3: 1–31 including GAG, Box A' and Box A (SEQ ID NO: 125)
5'-Hinge (SEQ ID NO: 126)
3'-Hinge (SEQ ID NO: 127)

DESCRIPTION

The present invention is based on the discovery that the eukaryotic pre-rRNA processing into functional 18S rRNA, a subunit of cellular translation machinery, is dependent on binding of both 5' and 3' hinge regions of the domain I of U3 snoRNA with the complementary sequences in the pre-rRNA. The binding of 5' and 3' hinge regions allows binding of Boxes A' and A of U3 snoRNA to the pre-rRNA which results in processing of the pre-rRNA into a functional 18S rRNA. 18S rRNA is an essential component of ribosomes which translate the genetic information in the cells into proteins. Moreover, the invention is based on the observation that, because the 5' and 3' hinge regions are evolutionarily non-conserved sequences, specific inhibition of growth of a pathogenic agent may be achieved by targeting species specific 5' and 3' hinge regions and thereby disrupting cellular protein synthesis, without affecting pre-rRNA processing in cells of a host organism affected by a pathogen.

The present invention encompasses the identification and use of antibiotic agents that interfere with the binding of domain I of U3 snoRNA with pre-rRNA, thereby interfering with processing of pre-rRNA into functional 18S rRNA. 18S rRNA is an essential component of eukaryotic cell translation process or protein synthesis. The present invention provides methods for identifying compounds that specifically interfere with the function of 5' and 3' hinge regions of domain I of U3 snoRNA in vitro and in vivo. These methods are based on the finding that binding of the domain I of U3 snoRNA with pre-rRNA is dependent on the single-stranded and evolutionarily non-conserved 5' and 3' hinge regions and their spatial arrangement. The binding in turn allows interaction between U3 snoRNA and pre-rRNA such that the correct processing of pre-rRNA can occur. Once the 18S rRNA is processed, it can participate in forming a complex with 5S and 28S rRNA and allow protein translation in the cell. On the basis of these findings, compounds that interfere with U3 snoRNA binding are expected to partially or totally inhibit protein synthesis in a cell. Once a test compound has been identified in vitro as a candidate antibiotic agent, it is further tested in vitro and in vivo for its ability to inhibit protein synthesis and cell growth, for example, in cell culture and in animal model systems. Once an antibiotic agent affecting only pathogenic organisms has been identified it can be applied to treatment of opportunistic infections in higher eukaryotic animals, for example, humans or plants.

The practice of the present invention employs, unless otherwise indicated, conventional molecular and cell biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait. ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989).

The invention is illustrated by the following non-limiting examples wherein the following materials and methods are employed. The entire disclosure of each of the literature references cited hereinafter are incorporated by reference herein.

RNA Sequences Useful According to the Invention

Figure 1A:
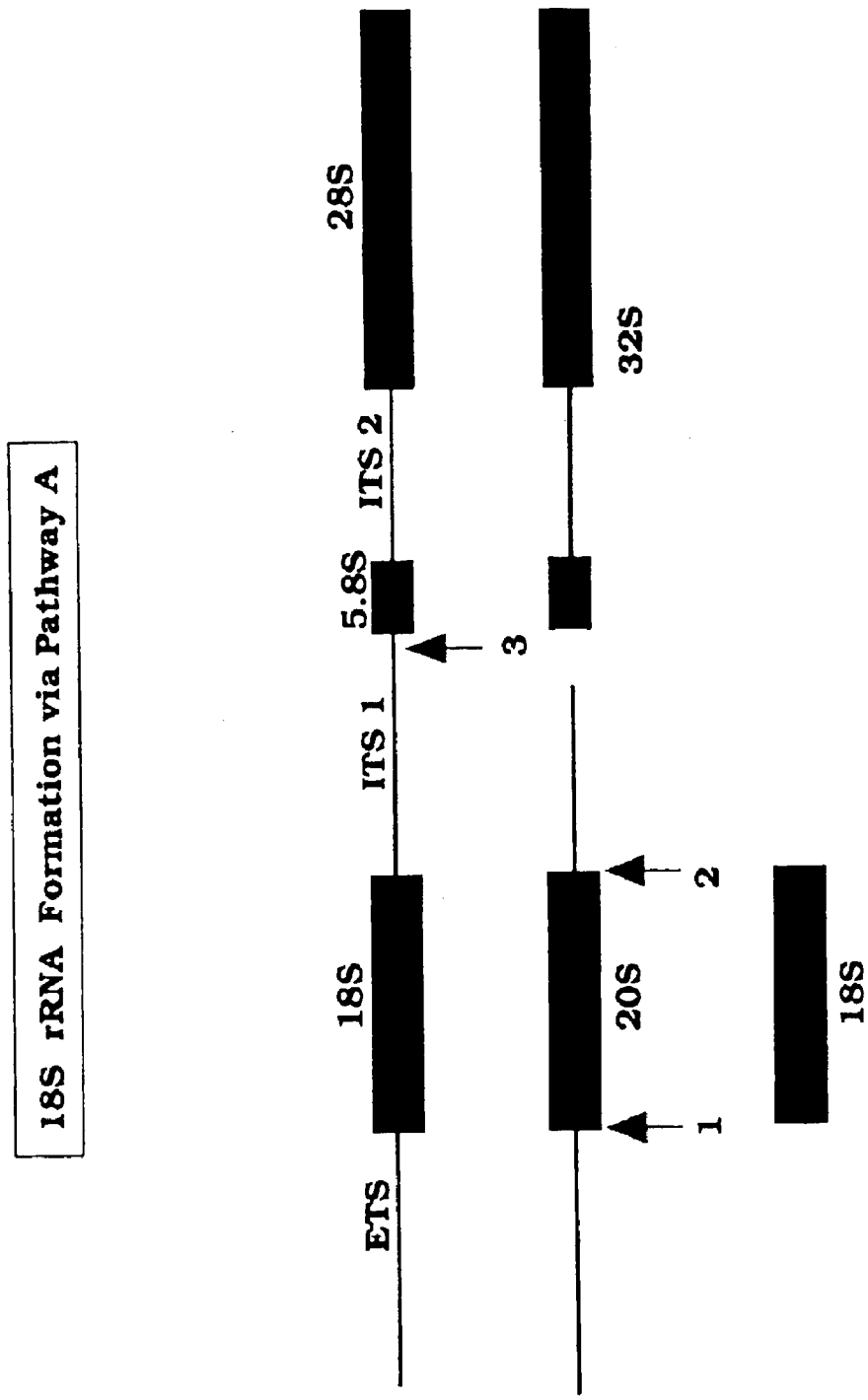
FIG. 1. 18S rRNA Processing requires U3 snoRNA.

A target for identifying agents which inhibit or prevent opportunistic infections is RNA, specifically processing of pre-rRNA to its mature form. U3 small nucleolar RNA (snoRNA) is the most abundant snoRNA in the cell (Reddy and Busch, 1983), and was the first metazoan snoRNA to be implicated in rRNA processing, both in vivo (Savino and Gerbi, 1990) and in a cell free system (Kass et al., 1990). In yeast, formation of 18S rRNA requires cleavage at several sites in pre-rRNA (A0, A1, A2) that is dependent on U3 snoRNA (Hughes and Ares, 1991) and U3 associated proteins ((Nop1p: Tollervey et al., 1991; Sof1p: Jansen et al., 1993; Mpp10: Dunbar et al., 1997; Nop5p: Wu et al., 1998; Nop58p: Lafontaine and Tollervey, 1999). In *Xenopus*, U3 dependent cleavage at sites 1+2 which flank the 18S coding region in pre-rRNA is needed to form mature 18S rRNA (FIG. 1A) (Lange et al., 1998; Borovjagin and Gerbi, 1999). In addition, U3 snoRNA is also needed for cleavage at site 3 (Savino and Gerbi, 1990), which is 5' to the 5.8S coding region in *Xenopus* pre-rRNA, to form 20S pre-rRNA (FIG. 1A). Two different rRNA processing pathways can occur in a single *Xenopus* oocyte (Savino and Gerbi, 1990); rRNA processing pathway A ensues when site 3 is the first to be cleaved. In contrast, sites 1+2 of pre-rRNA are cleaved first in pathway B (Savino and Gerbi, 1990). U3 snoRNA influences whether pathway A or pathway B will be taken in rRNA processing (Borovjagin and Gerbi, 1999). The 3' region (domain II) of U3 is required and sufficient for cleavage at site 3 (Borovjagin and Gerbi, 1999). However, pre-rRNA cleavage at sites 1+2 appears to require sequences throughout the whole U3 molecule (Borovjagin and Gerbi, 1999). Here we identify the features within *Xenopus* U3 snoRNA that are critical for cleavage at sites 1+2 to generate 18S rRNA.

Figure 1B:
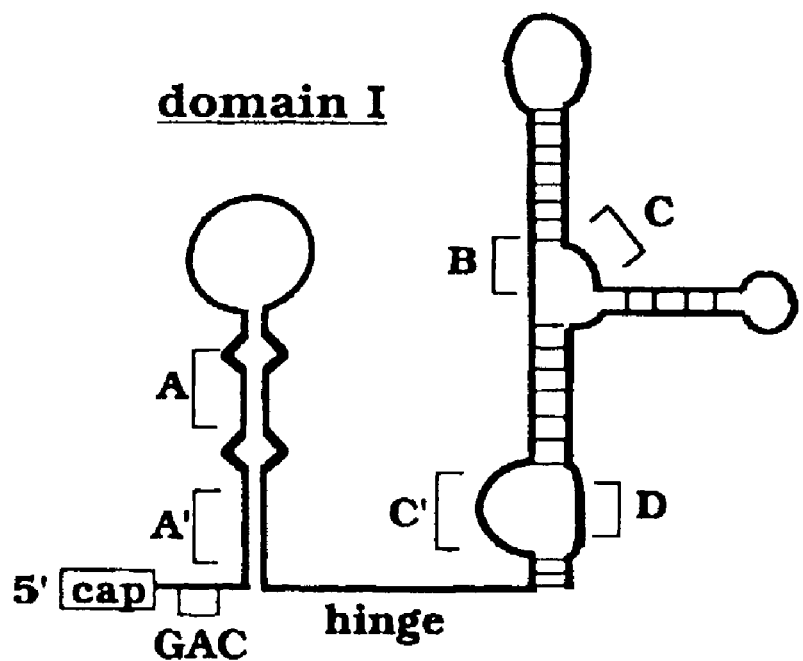

At the primary sequence level, U3 snoRNA has several stretches that are evolutionarily conserved between various organisms. The first of these to be discerned were Boxes A, B and C (Wise and Weiner, 1980; Hughes et al., 1987; Jeppesen et al., 1988). Subsequently, Box D (Tyc and Steitz, 1989), Box C' (Tycowski et al., 1993; also called Box A° by Marshallsay et al., 1992), Box A' (Myslinski et al., 1990) and the GAC element (Samarsky and Fournier, 1998) were discovered. The GAC element and Boxes A' and A reside in domain I of U3 snoRNA; Boxes C', B, C and D are in domain II (FIG. 1B).

In addition to studies on the primary sequence of U3 snoRNA, the secondary structure of this molecule has also been examined. Typically, both domains of metazoan U3 snoRNA are illustrated as base-paired stems separated by a single stranded "hinge" region (FIG. 1B). Chemical modification experiments performed on vertebrate U3 concurred that domain II is highly base-paired, and the hinge region is single-stranded (Parker and Steitz, 1987; Jeppesen et al., 1988). However, the results differed for domain I of vertebrate U3 snoRNA. The potential base-pairing of U3 domain I is further called into question since it is not rigorously supported by compensatory base changes in phylogenetic comparisons (Jeppesen et al., 1988). Moreover, the putative long 5' stem that can be identified for vertebrate U3 snoRNAs is considerably shorter when drawn for Tetrahymena (Ørum et al., 1993) and trypanosomes (Hartshorne and Agabian, 1994) and has been identified instead as two short stems in yeast (Porter et al., 1988; Ségault et al., 1992; Mougin et al., 1996; Méreau et al., 1997) and plants (Kiss and Solymosy, 1990; Marshallsay et al., 1990). Therefore, although many investigators depict U3 domain I as base-paired, until the present invention it has been unclear if this is the case.

To gain insight into the structural requirements of U3 for rRNA processing, we created mutants designed to alter U3 secondary structure and tested their effect on U3 function in 18S rRNA formation. We conclude that domain I does not need to be base-paired for U3 function. These results led us to re-evaluate the structure of U3 when it is not yet bound to pre-rRNA, and we conclude that domain I of vertebrate U3 should be drawn similar to the proposal of Méreau et al. (1997) for unbound yeast U3, rather than as a single base-paired stem.

Our mutagenesis studies uncovered a new element in domain I of U3 that we call the 5' hinge; it is important but not essential for 18S rRNA production. In contrast, we show that the single stranded hinge region, renamed here 3' hinge region, which abuts domain II is absolutely essential for 18S rRNA processing. Insertion and deletion analyses demonstrate that a defined distance between the 5' hinge and 3' hinge is required for U3 function, suggesting that they act in unison. We present here a model, which is consistent with the data shown here and with phylogenetic comparisons, in which the 5' hinge and the 3' hinge base-pair with the external transcribed spacer (ETS) of pre-rRNA to correctly position U3 on pre-rRNA for its function in rRNA processing.

It has been suggested that Boxes A' and A of U3 snoRNA base-pair with 18S rRNA sequences in pre-rRNA to prevent premature formation of the central pseudoknot found in mature 18S rRNA (Hughes, 1996). This proposed interaction is phylogenetically conserved (Hughes, 1996) and consistent with in vivo chemical modification (Méreau et al., 1997). The present invention is the first disclosure in any system documenting the importance of U3 Box A' for 18S rRNA formation. The sequence and/or its length between Box A and the 5' hinge of U3 appears to be important, since its deletion in yeast inhibited growth (mutant 443 in Méreau et al., 1997). Here, we show that the distance from Boxes A' and A to the 5' hinge is critical for 18S rRNA production in *Xenopus*, suggesting that the proposed interactions of pre-rRNA with the two hinge regions of U3 and with U3 Boxes A' and A occur at the same time.

RNA and DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal, (1984). Preferably, DNA segments corresponding to all or a portion of the nucleic acid regions and structures of this invention may be isolated individually using the polymerase chain reaction (PCR) with primers based on the sequences disclosed in the following Examples (See methods in M. A. Innis, et al., "PCR Protocols: A Guide To Methods and Applications," Academic Press, 1990).

The sequences according to this invention can be isolated from a cell, synthesized chemically or enzymatically, for example, by PCR, or they can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Sequences of U3 snoRNA 5' and 3' Hinge Regions of Pathogens Useful According to the Invention The U3 snoRNA sequences useful according to the present invention that are required for binding of U3 snoRNA with the pre-rRNA include minimally the 5' and 3' hinge regions. The following three sequences are examples of the hinge regions identified from selected pathogens. These example sequences are the minimal sequences required for binding. The nucleotide numbering is in accordance with the published sequences:

*Saccharomyces cerevisiae* 5' hinge region (5'-$^{39}$CACUCUUUGA$^{48}$-3') (SEQ ID NO: 3) and 3' hinge region (5'-$^{62}$CCACUGAAUCC$^{72}$-3') (SEQ ID NO: 4); *Hansenula wingei* 5' hinge region (5'-$^{39}$CCCUCUUUGUCU$^{50}$-3') (SEQ ID NO: 5) and 3' hinge region (5'-$^{59}$GAGCCACUGAAUCC$^{72}$-3') (SEQ ID NO: 6); *Schizosaccharomyces pombe* 5' hinge region (5'-$^{46}$UGGG-UU$^{51}$-3') (SEQ ID NO: 7) and 3' hinge region (5'-$^{66}$CAGAA$^{70}$-3') (SEQ ID NO: 8); and *Trypanosoma brucei* 5' hinge region (5'-$^{43}$U-UAAAU$^{48}$-3') (SEQ ID NO: 9) and 3' hinge region (5'-$^{52}$AAAUAACCAACA$^{63}$-3') (SEQ ID NO: 10)

One embodiment of the present invention is to screen for antibiotic agents by identifying agents that bind to the 5' and/or 3' hinge sequences thereby preventing the binding of U3 snoRNA with 18S pre-rRNA.

The following sequences are the Homo sapiens U3 snoRNA 5' and 3' hinge sequences: Homo sapiens 5' hinge region (5'-$^{39}$CUAGAGAAG$^{47}$-3') (SEQ ID NO: 11) and the 3' hinge region (5'-$^{63}$AGAGCAC$^{69}$-3') (SEQ ID NO: 12). One embodiment of the present invention is to screen for antibiotic agents that do not affect binding of Homo sapiens U3 snoRNA binding with pre-rRNA.

Cloning Sequences from Other Pathogens

The U3 snoRNA sequences according to the invention may be identified from other pathogens by conventional hybridization based or PCR based methods using probes or primers that are designed from the U3-specific evolutionarily conserved sequences such as box A or A' and box B of the U3 snoRNA. These methods are known to one skilled in the art (See, for example, methods in M. A. Innis, et al., "PCR Protocols: A Guide To Methods and Applications," Academic Press, 1990.). The non-conserved 3' and 5' hinge regions can then be identified by aligning the U3 snoRNA sequence with 18S pre-rRNA sequence using nucleic acid sequence comparison software such as DNAStar™ (DNAStar Inc., Madison Wis.) or GCG Sequence analysis package (UK HGMP Resource Centre, funded by MRC) according to the manufacturer's instructions, or the like systems designed for sequence comparison and identifying sequences that have about 80% or greater identity to Box A' or Box A on the 5' side of the sequence and Box B on the 3' side of the sequence. 5' to Box B there is another evolutionarily conserved sequence called Box C'. The newly identified sequence will be aligned with the known sequence for U3 snoRNA from a lower eukaryote, for example, yeast or a higher eukaryote, for example, *Xenopus* or human. The stretches of sequence identity to Boxes A' or A on the 5' side and C' and B on the 3' side will be aligned. The sequence between Box A and Box C' contains the 5' hinge and the 3' hinge regions. These 5' and 3' hinge regions are not conserved during evolution, but their position in the U3 snoRNA molecule remains constant. Once the primary sequence alignment has been performed, the secondary structure of domain I of the newly identified U3 snoRNA will be arranged according to the evolutionarily conserved structure shown for, for example, yeast or *Xenopus* (Borovjagin and Gerbi, J. Mol. Biol. in press). The secondary structure will further refine and confirm the identity of the 5' hinge and the 3' hinge regions as both are single stranded in the secondary structure of the molecule).

Total cellular or nuclear RNA is isolated from the pathogen using standard procedures known in the art. The isolated total RNA serves as the template for primer extension in the sequencing reaction. Oligonucleotides that can be used as primers are selected from a group of evolutionarily conserved U3 snoRNA domain II regions consisting of sequences complementary to box C' (5'-AGGAAGA-3') (SEQ ID NO: 13), box B (5'-AGCGUGAA-3') (SEQ ID NO: 14), box C (5'-AUUGAUGA-3') (SEQ ID NO: 15) or box D (5'-GCUGA-3') (SEQ ID NO: 16). Use of box B sequence is preferred because it is U3 snoRNA specific. The primer extension reaction is performed using reverse transcriptase enzyme to produce a complementary DNA copy of the U3 snoRNA template. The reaction is performed in the presence of dideoxynucleotides which allows DNA sequencing of the reverse transcript. The reverse transcript products are analyzed on sequencing gels known in the art.

Alternatively, the template in a sequencing reaction can be a PCR product. The PCR amplification to produce the template is performed using primers designed from evolutionarily conserved regions flanking the 3' and 5' hinge regions. The forward primer is designed using box A' or box A of U3 domain I as a template and box B sequence serves as a reverse primer template. The PCR product is sequenced using methods that are well known in the art (see, for example, methods in M. A. Innis, et al., "PCR Protocols: A Guide To Methods and Applications," Academic Press, 1990.).

The sequences that are obtained from the sequencing reactions are compared with known U3 snoRNA sequences to identify the 5' hinge region and the 3' hinge region. The secondary structure, or folding, of the domain I of the U3 snoRNA sequence from the pathogen is determined manually or using appropriate computer software as described above. The single-stranded, non-conserved 5' hinge and the 3' hinge regions are identified from the secondary structure by comparison to the folded structure for U3 snoRNA from *Xenopus* and from the yeast *Saccharomyces cerevisiae* when in the form not bound to pre-rRNA by aligning the conserved regions using the standard Watson-Crick base pairing rules. Once the conserved sequences are aligned, the non-conserved 5' and 3' hinge regions can be identified from the secondary structure of the RNA. Alternatively, if both pre-rRNA and U3 snoRNA have been cloned the sequence alignment may be performed between the pre-rRNA and the U3 snoRNA using sequence alignment software as described above.

Sequences of Pre-rRNA Useful According to the Present Invention

The pre-rRNA sequences useful according to the present invention that are required for binding of pre-rRNA with U3 snoRNA include minimally the sequences complementary to U3 snoRNA 5' and 3' hinge regions. The following three sequences are examples such complementary regions in the pre-rRNA identified from selected pathogens. These example sequences are the minimal sequences required for binding. The nucleotide numbering is in accordance to the published sequences:

*Saccharomyces cerevisiae* ETS complementary to U3 snoRNA 5' hinge region (5'-$^{471}$UCAAAGAGUG$^{480}$-3') (SEQ ID NO: 17) and ETS complementary to U3 snoRNA 3' hinge region (5'-$^{282}$GGAUUUGGUGG$^{292}$-3') (SEQ ID NO: 18); *Hansenula wingei* ETS complementary to U3 snoRNA 5' hinge region (5'-$^{788}$AAACAAAGAGGG$^{799}$-3') (SEQ ID NO: 19) and ETS complementary to U3 snoRNA 3' hinge region (5'-$^{603}$GGAUUUUAGUGGAUU$^{617}$-3') (SEQ ID NO: 20); *Schizosaccharomyces pombe* ETS complementary to U3 snoRNA 5' hinge region (5'-$^{1053}$AACCUCA$^{1059}$-3') (SEQ ID NO: 21) and ETS complementary to U3 snoRNA 3' hinge region (5'-$^{852}$UUCUG$^{856}$-3') (SEQ ID NO: 22); and *Trypanosoma brucei* ETS complementary to U3 snoRNA 5' hinge region (5'-$^{936}$AUUUAUA$^{943}$-3') (SEQ ID NO: 23) and ETS complementary to U3 snoRNA 5' hinge region (5'-$^{862}$UGUUGGUUGUGU$^{873}$-3') (SEQ ID NO: 24).

One embodiment of the present invention is to screen for antibiotic agents by identifying agents that bind to or cleave the ETS sequences thereby preventing the binding of U3 snoRNA 3' and/or 5' hinge regions with pre-rRNA.

The following sequences present the Homo sapiens ETS sequences in the pre-rRNA:

pre-rRNA ETS sequence complementary to the U3 snoRNA 5' hinge region (5'-$^{1403}$CUUCUCUAG$^{1411}$-3') (SEQ ID NO: 25) and the pre-rRNA ETS sequence complementary to the U3 snoRNA 3' hinge region (5'-$^{439}$GUGCUCU$^{445}$-3') (SEQ ID NO: 26).

One embodiment of the present invention is to screen for antibiotic agents that do not cleave or disrupt binding of Homo sapiens U3 snoRNA with complementary ETS sequences in pre-rRNA.

Cloning Additional Pre-rRNA Sequences Useful According to the Present Invention

The pre-rRNA sequences according to the invention may be identified from other pathogens by conventional hybridization based or polymerase chain reaction (PCR) based methods using probes or primers that are designed from the evolutionarily conserved sequences such as 18S rRNA. These methods are known to one skilled in the art (See, for example, methods in M. A. Innis, et al., "PCR Protocols: A Guide To Methods and Applications," Academic Press, 1990.). The non-conserved regions of pre-rRNA that are complementary to 3' and 5' hinge regions can be identified by aligning the pre-rRNA sequence with U3 snoRNA sequence by using nucleic acid sequence comparison software such as DNA-Star or GCG or other systems designed for analysis of nucleic acid sequences.

Total cellular or nuclear RNA from the pathogen is isolated from the pathogen using standard procedures known in the art. The isolated total RNA serves as the template for primer extension in the sequencing reaction. Oligonucleotides that can be used as primers are selected from a group of evolutionarily conserved U3 snoRNA domain II regions consisting of sequences complementary to box C' (5'-AGGAAGA-3') (SEQ ID NO: 13), box B (5'-AGCGUGAA-3') (SEQ ID NO: 14), box C (5'-AUUGAUGA-3') (SEQ ID NO: 15) or box D (5'-GCUGA-3') (SEQ ID NO: 16). Use of box B sequence is preferred because it is U3 snoRNA specific. The primer extension reaction is performed using reverse transcriptase enzyme to produce a complementary DNA copy of the U3 RNA template. The reaction is performed in the presence of dideoxynucleotides which allows DNA sequencing of the reverse transcript. The reverse transcript products are analyzed on sequencing gels known in the art.

Alternatively, the template in a sequencing reaction can be a PCR product. The PCR amplification to produce the template is performed using primers designed from evolutionarily conserved regions flanking the 3' and 5' hinge regions. The forward primer is designed using box A' or box A of U3 domain I as a template and box B sequence serves as a reverse primer template. The PCR product is sequenced using methods that are well known in the art.

The sequences that are obtained from the sequencing reactions are compared with known U3 snoRNA sequences to identify the 5' hinge region and the 3' hinge region. The secondary structure, or folding, of the domain I of the U3 snoRNA sequence from the pathogen is determined manually or using appropriate computer software as described above. The single-stranded 5' hinge and the 3' hinge regions are identified from the secondary structure by comparison to the folded structure for U3 snoRNA from *Xenopus* and from the yeast *Saccharomyces cerevisiae* when in the form not bound to pre-rRNA using same approach as described above.

Confirmation that the 5' Hinge and 3' Hinge of U3 snoRNA from the Pathogen are Complementary to Sequences in the ETS of Pre-rRNA of the Pathogen According to the Present Invention Labelled oligonucleotides containing the 5' hinge or 3' hinge sequence of U3 snoRNA from the pathogen are used in a Northern blot hybridization analysis as a probe against the nuclear RNA from the pathogen. The probes that contain the correct 5' and 3' hinge regions will bind and consequently label the 40S and 20S pre-rRNAs both of which contain the ETS and the putative complementary sequences present in the nuclear RNA preparation.

In Vitro Binding Assay According to the Present Invention

An in vitro binding assay according to the invention is performed by first labeling either a synthetic oligoribonucleotide containing the sequence of the 5' hinge region or the 3' hinge region of U3 snoRNA from the pathogen of interest. The labelled oligonucleotide is mixed with and allowed to bind to a synthetic complementary oligonucleotide under appropriate annealing conditions where the temperature is determined by the base composition and length of the annealing oligonucleotides, as specified in Sambrook et al.; the buffer can be 2×SSC=0.3 M NaCl, 0.03 M Na-citrate, pH 7.0 or any of the alternative standard conditions. In a parallel reaction the antibiotic agent is added to the reaction mixture before mixing the labeled oligonucleotide and synthetic complementary oligoribonucleotide.

The mixtures and the individual labeled component are separated in parallel wells on a non-denaturing gel. The bound sequences are identified as slower moving fragments, or "gel-shifts", on the gel compared to faster moving unbound oligonucleotides. The inhibition of binding by the antibiotic agent is observed by, for example, 5%, 10%, 25%, 50%, 75%, or 100% decrease in the appearance of gel-shift as compared to the control with no addition of antibiotic agent, or 5%, 10%, 25%, 50%, 75%, or 100% of increase in the appearance of unbound, faster-moving fragments, as compared to the control with no addition of antibiotic agent.

Nucleic Acid Constructs Useful in the Cellular Assays According to the Present Invention The effects of the antibiotic agents according to the present invention on rRNA processing as well as on cell growth, cell division and cell viability can be tested in living cells. The 5' and 3' hinge region of U3 and the complementary sequences in the ETS of pre-rRNA are replaced by those from the pathogenic eukaryote. The remainder of the U3 snoRNA sequence and the pre-rRNA sequence will be from a model eukaryotic test system such as *Xenopus* oocytes.

The 5' and 3' hinge region of U3 snoRNA of the *Xenopus* and the corresponding complementary sequences in the ETS of pre-rRNA will be replaced by those from the pathogenic eukaryote using standard PCR-based mutagenesis methods known in the art. The remainder of the U3 snoRNA sequence and the pre-rRNA sequence will be from a model eukaryotic test system, such as *Xenopus* oocyte. An additional "tag", a recognition sequence with a neutral mutation such as inserted additional nucleotides may be added to the recombinant mutant U3 snoRNA of, for example, *Xenopus* U3 snoRNA to distinguish it from the endogenous U3 snoRNA.

In addition, a clone of rDNA, comprising the normal RNA polymerase I promoter; the ETS; 18S coding region containing a tag placed in a non-essential expansion segment; the ITS1; and optionally the 5.8S, ITS2 and a tagged 28S coding region will be constructed by standard techniques to replace the complementary sequences in the ETS to the U3 5' and 3' hinge regions of the model organism, such as *Xenopus*, with novel sequences that are complementary to the 5' and 3' hinge region sequences created above.

Analysis of Pre-rRNA Processing According to the Present Invention

The rDNA construct is injected into the nucleus of *Xenopus* oocytes or other eukaryotic cells where the rDNA has been cloned and sequenced and which can be injected by standard methods. After a period of time, preferably about 12–24 hours, the nuclear RNA will be isolated and the separated according to its size on an agarose gel and subjected to a Northern blot hybridization using labeled 18S tag as a probe. The label may be any radioactive or non-radioactive label which are well known in the art. The probe should not detect the 40S pre-rRNA because the endogenous ETS sites complementary to the U3 snoRNA 5' and 3' hinge regions result in inability of the endogenous U3 snoRNA to dock on the mutant pre-rRNA.

In a parallel experiment, U3 snoRNA containing the 5' and/or 3' hinge substitutions or alternatively, the cloned U3 gene containing these substitutions in the 5' hinge and/or 3' hinge will be co-injected. A subsequent agarose gel size separation and Northern blot hybridization as described above reveals if the 5' hinge region mutant of U3 snoRNA, the 3' hinge region mutant of U3 snoRNA, or both mutations together in one U3 snoRNA molecule are able to rescue rRNA processing in which case the 18S tag detects a fragment of newly synthesized and thereby tagged 18S rRNA.

Finally, in a parallel experiment, the antibiotic agent will also be introduced in varying concentrations, in addition to the tagged rDNA clone and the mutated U3 snoRNA, to analyze by the Northern blot hybridization using a probe against the 18S tag. If the antibiotic agent has prevented 18S rRNA formation, about 5%, 10%, 15%, 25%, 50%, 75% up to and including 100% reduction, compared to the control, in the amount of the label recognizing the mature 18S rRNA on the gel after Northern blot hybridization will be observed. Comparison of the incorporated label can be performed using, for example, a phosphorimager or x-ray film followed by densitometry.

Analysis of Protein Synthesis According to the Present Invention

In experiments where protein synthesis is monitored in a cell free system, the ribosomes of the cell free system, for example, rabbit reticulocyte lysate or wheat germ lysate, will be centrifuged out and discarded. The discarded ribosomes will be replaced by the large and small subunits of, for example, Xenopus ribosomes. Xenopus ribosomes can be obtained from a sucrose gradient and enriched for ribosomal subunits that were newly synthesized in the experiment described above. The ribosomes are precipitated from the sucrose gradient by streptavidin immunoprecipitation using a biotinylated oligonucleotide complementary to tag sequences in nonessential expansion segments of 18S and 28S rRNA. If 18S rRNA formation is inhibited by the antibiotic agent, no newly formed small ribosomal subunits can be observed and hence no protein synthesis will occur. Protein synthesis is assayed using exogenous mRNA, for example, BMV RNA (Promega, Madion, Wis.) which is added to the cell free system in the presence of radioactive amino acids, and the labeled protein will be analyzed by SDS-PAGE.

Analysis of Pre-rRNA Processing in Living Cells According to the Present Invention A plasmid comprising DNA encoding yeast U3 snoRNA and a plasmid of yeast rDNA that encodes yeast pre-rRNA with sequence tags in nonessential expansion segments of 18S and 28S rRNA are introduced into, for example, Saccharomyces cerevisiae yeast using the system described by Beltrame and Tollervey (1995). The transforming DNA comprises the 5' and 3' hinge regions of U3 snoRNA of the pathogen rather than of yeast or alternatively other hosts. Similarly, the sequences in the ETS of the transforming rDNA that normally are complementary to the 5' hinge and 3' hinge regions of yeast U3 snoRNA are replaced with sequences complementary to the 5' hinge and the 3' hinge regions of the pathogen. The episomal U3 snoRNA is transcribed from its own natural promoter, while the transforming rDNA is under the control of an inducible promoter (Beltrame and Tollervey, 1995).

After transformation, the transcription from the plasmids is induced as described by Beltrame and Tollervey (1995). At the same time, these inducible conditions, for example, galactose inducible medium, will prevent transcription of endogenous rDNA. Therefore, just the tagged rRNA will be produced. The total RNA is isolated by standard methods and separated according to the size on an agarose gel. The Northern blot hybridization using probes against the 18S and 28S tags is performed to observe synthesized and processed pre-rRNA. The tagged pre-rRNA containing the pathogen's ETS sequences complementary to the pathogen's 5' and 3' hinge regions of U3 snoRNA can only be processed to give mature 18S rRNA in the presence of the episomal U3 snoRNA whose 5' hinge and 3' hinge sequences have been replaced by those of the pathogen and hence are complementary to the replaced sequences in the rRNA plasmid. In a parallel reaction the cells are treated with a candidate antibiotic agent after the transformation. Reduction in the amount of processed 18S compared to the untreated control sample indicates inhibition of processing and therefore antibiotic activity.

Analysis of the Ribosome Synthesis According to the Present Invention

The same reaction described above can be used to collect and analyze ribosome synthesis. For example, transformed yeast cells are lysed and the cell lysates are separated using sucrose gradients known in the art. The ribosomes are collected from sucrose gradients and hybridised with the 18S and 28S tags to indicate that the transforming rRNA is incorporated into functional ribosomes. The functional ribosomes can be observed by their presence in polysomes which are detected as a faster migrating fraction compared to single ribosomes or ribosomal subunits on a standard sucrose gradient, for example, 5–20% or 15–30% sucrose gradient. The detection is performed by Northern blot hybridization with probes complementary to the 18S and 28S tags. Tagged 18S rRNA and small ribosomal subunit production will only occur when the rRNA plasmid with the substituted ETS sequences is grown and transcribed in the presence of the U3 plasmid described above with the substituted 5' and 3' hinges. In a parallel reaction, a candidate antibiotic agent is added and the inhibition of ribosome synthesis is observed by at least and up to 10%, 20%, 50%, 75%, or 100% decrease of 18S rRNA as detected by Northern blot hybridization as described above.

Analysis of the Protein Synthesis in the Living Cells According to the Present Invention After transformation and activation of transcription of the inducible plasmids, also yeast protein synthesis can be monitored by culturing the transformed yeast in the inducing medium with or without the antibiotic agent and with labelled amino acids to analyze newly made proteins by SDS-PAGE. Reduced amount of incorporated label in the samples treated with candidate antibiotic agent compared to the untreated sample indicates antibiotic properties of the candidate agent.

Analysis of Cell Growth According to the Present Invention

Moreover, the cell growth can be assessed after transformation and activation of transcription of the inducible plasmids by, for example, light microscopically observing the size of the cells in grown with or without the antibiotic agent. The lack of increase of at least about 20% in cell size from the size of the cell after cell division, as judged by microscopy, is indicative of inhibition of cell growth by the candidate antibiotic agent.

Analysis of Cell Division According to the Present Invention

Also, cell division can be assessed after transformation and activation of transcription of the inducible plasmids, for example, by periodical cell counting over a specified time intervals and by comparing the increase of cell number between the antibiotic agent treated and untreated cell cultures. Up to and including 10%, 15%, 20%, 50%, 75%, and 100% fewer cells in the candidate antibiotic agent treated sample compared to the control sample indicated antibiotic activity.

Analysis of Cell Viability According to the Present Invention

Finally, yeast cell viability can be assayed by, for example, Trypan Blue dye which is actively excluded from living cells but readily enters and stains dead cells. The staining can be monitored, for example, by light microscopy. Up to and including 10%, 15%, 20%, 50%, 75%, and 100% increase in the number of the stained cells in the candidate antibiotic agent treated sample compared to the untreated control is indicative of reduced cell viability and thereby antibiotic activity of the candidate agent.

Analysis in the Effects of Candidate Antibiotic Agents on Pathogens According to the Present Invention The pathogen, is cultured in the absence or presence of the candidate antibiotic agent. At a variety of time points after treatment, 18S rRNA formation, incorporation into ribosomes, protein synthesis, cell growth, cell division and cell viability will be assayed as described above for living cell-based assays. The only difference is that endogenous rather than tagged rDNA will be expressed, and at the start of the experiment label will be present in the medium to label the newly synthesized RNA, thereby distinguishing it from pre-existing rRNA rather than distinguishing it by hybridization to a tag in rRNA.

Candidate Antibiotic Agents According to the Present Invention

A candidate antibiotic agent that can be tested for according to the invention include any recombinant, modified or natural nucleic acid molecule including anti-sense oligonucleotides; library of recombinant, modified or natural nucleic acid molecules; organic or inorganic compound; library of organic or inorganic compounds where the agent has the capacity to inhibit binding between a first recombinant RNA comprising 5' and 3' hinge regions of domain I of U3 snoRNA and a second recombinant pre-rRNA comprising ETS region by binding to one of the 5' or 3' hinge regions or both of the first recombinant RNA; binding to the complementary sequences of 5' or 3' hinge regions in the second recombinant RNA; destroying the 5' and/or 3' hinge regions of the first recombinant RNA by cleaving such regions; or destroying the complementary sequences of 5' or 3' hinge regions in the second recombinant RNA by cleaving them. Preferably, the inhibition of binding or cleavage will also result in inhibiting processing of functional 18S rRNA, and may also thereby inhibit ribosome synthesis, and may further inhibit protein synthesis, and may additionally result in inhibition of cell growth, cell division, and ultimately cell viability.

Test compounds for use in high-throughput screening methods may be found in large libraries of synthetic or natural substances. Numerous means are currently used for random and directed synthesis of saccharide, peptide, and nucleic acid-based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). In addition, there exist methods for generating combinatorial libraries based on peptides, oligonucleotides, and other organic compounds (Baum, C&EN, Feb. 7, 1994, page 20–26). Alternatively, libraries of natural compounds in the form of bacterial, fungal, plant and animal extracts are available from e.g. Pan Labs (Bothell, Wash.) or MycoSearch (NC), or are readily producible. Additionally, natural and synthetically produced libraries and compounds are readily modified through conventional chemical, physical, and biochemical means.

Dosage and Mode of Administration

An antibiotic agent such as an antisense oligonucleotide or organic or inorganic small molecule may be administered in a eukaryotic host infected with a pathogenic agent as necessary. The antibiotic agent may be adminsitered to, for example, a mammal, orally, cutaneously, subcutaneously, intramuscularly, intravenously, or may be inhaled as aerosols in pharmacologically suitable media daily, weekly, monthly as determined necessary in varying dosages. Administration of an antibiotic agent to, for example, a plant, may be direct spraying onto a plant or into the soil in a suitable liquid or solid medium.

Administration of, for example, small organic or inorganic molecule therapeutic agents in an individual infected with a pathogenic agent will vary depending on the potency of the small organic or inorganic molecule. For a very potent small organic or inorganic molecule inhibitor, nanogram (ng) amounts kilogram (kg) of patient, or microgram ($\mu$g) amounts per kg of patient may be sufficient. Thus, for small organic molecules, peptides, or peptoids (also called peptodimimetics), the dosage range can be for example, from about 100 ng/kg to about 500 mg/kg of patient weight, or the dosage range can be a range within this broad range, for example, about 100 ng/kg to 400 ng/kg, from about 500 ng/kg to about 1 $\mu$g/kg, from about 5 $\mu$g/kg to about 100 $\mu$g/kg, from about 150 $\mu$g/kg to about 500 $\mu$g/kg, from about 600 $\mu$g/kg to about 1 mg/kg, or from about 25 mg/kg, to about 500 mg/kg of patient weight.

The individual doses for viral gene delivery vehicles for delivery of polynucleotide inhibitors, such as antisense molecules, normally used are $10^7$ to $10^9$ colony forming units (c.f.u of neomycin resistance titered on HT1080 cells) per body. Dosages for, for example, adeno-associated virus (AAV) containing delivery systems are in the range of about $10^9$ to about $10^{11}$ particles per body. Dosages for nonviral gene delivery vehicles for delivering polynucleotide inhibitors of 3' or 5' hinge regions of domain I of U3 snoRNA are described for example in U.S. Pat. Nos. 5,589,466 and 5,580,859. Dosage of nonviral gene delivery vehicles can be 1 $\mu$g, preferably at least 5 or 10 $\mu$g, and more preferably at least 50 or 100 $\mu$g of polynucleotide, providing one or more dosages.

In all cases, routine experimentation in clinical trials will determine specific ranges for optimal therapeutic effect, for each therapeutic and each administrative protocol, and administration to specific patients will also be adjusted to within effective and safe ranges depending on the patients' condition and responsiveness to initial administrations.

All of the antibiotic agents discovered by the methods according to the present invention can be incorporated into an appropriate pharmaceutical composition that includes a pharmaceutically acceptable carrier for the agent. The pharmaceutical carrier for the agents may be the same or different for each agent. Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; an the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier. Liposomes are described in U.S. Pat. Nos. 5,422,120 and 4,762,915, WO 95/13796, WO 94/23697, WO 91/144445 and EP 524,968, and in Starrier, Biochemistry, pages 236–240 (1975) W. H. Freeman, San Francisco, Shokai, Biochem. Biophys. Acct. 600:1 (1980); Bayer, Biochem Biophys Acct 550:464 (1979); Rivet, Meth. Enzyme. 149:119 (1987); Wang, Proc. Natl. Acad. Sci. 84:785: (1987); and Plant, Anal. Biochem 176:420 (1989).

The pharmaceutically acceptable carrier or diluent may be combined with other agents to provide a composition either as a liquid solution, or as a solid form (e.g., lyophilized) which can be resuspended in a solution prior to administration. The composition can be administered by parenteral or nonparenteral routes. Parenteral routes can include local injection into an organ or space of the body or systemic injection including intravenous, intraarterial injections or other systemic routes of administration. Nonparenteral routes can include oral administration.

All types of pathogenic eukaryotic cells including fungal, yeast, and protozoa may be used as targets for antibiotic agents according to the invention.

EXAMPLE 1

U3 snoRNA Does not Require a Base-paired Stem in Domain I to Produce 18S rRNA To investigate whether the putative base-paired stem of U3 domain I is important for U3 snoRNA function in 18S rRNA processing, we created a series of mutations to open the putative stem or compensatory mutations to close the stem. The U3 mutants were tested for their ability to rescue 18S rRNA processing after endogenous U3 snoRNA had been disrupted by injecting an antisense oligonucleotide into *Xenopus* oocyte nuclei. Endogenous RNase H cleaves U3 snoRNA at the position where it hybridizes with the DNA oligonucleotide, and exonucleases subsequently trim the cleaved U3 molecule back to the base of the stem of domain II (Borovjagin and Gerbi, 1999). The residual fragment of U3 containing just domain II is stable but is unable to function in cleavage of sites 1+2 in pre-rRNA (Borovjagin and Gerbi, 1999). FIG. 2 presents the mutations to be discussed below; panels A–C show the position of the mutations on the putative stem of U3 domain I. FIG. 2D indicates the results of the U3 mutations on 18S rRNA production; also, where the mutations map relative to sites of proposed base-pairing with 18S and ETS sequences in pre-rRNA is indicated. All the U3 snoRNA mutants studied here were stable 18 hours after injection into *Xenopus* oocytes, as judged by the ratio of mutant U3 snoRNA to U2 snRNA, co-injected as a control; this ratio did not change significantly between 0 and 18 hours after injection (FIG. 3). Therefore, failure of a U3 mutant to function in rRNA processing was not due to degradation of the mutant U3 snoRNA.

EXAMPLE 2

The 5' Hinge Region of Domain I of U3 snoRNA Must Contain Box A' and be Single-Stranded for U3 Function in 18S rRNA Production We showed that the base of the putative stem of U3 domain I is required for the U3 snoRNA function in the *Xenopus* oocyte model system. *Xenopus* oocytes were isolated and treated as described previously (Borovjagin and Gerbi, 1999). Briefly, endogenous U3 snoRNA was depleted by two sequential injections spaced 4 hours apart of an antisense oligonucleotide complementary to U3 nt 39–54. Newly synthesized pre-rRNA was in vivo labeled by injection of 0.5 $\mu$Ci-$^{32}$P-UTP (4000 Ci/mmol; New England Nuclear, Boston, Mass.). Capped snoRNAs were transcribed in vitro by T7 RNA polymerase (Ambion Megashortscript kit, Austin, Tex.) and 9.2 nl of 0.5 ng/nl to 1.5 ng/nl was injected 4 hours after the last depletion of endogenous U3 to assay its ability to restore 18S rRNA processing. Total nuclear RNA was extracted from 5–10 oocytes by the Rapid Total RNA Isolation kit (5 Prime-3 Prime, Boulder, Colo.) 18 hours later. Radioactive rRNA precursors were resolved on a 1.2% agarose gel containing 6% formaldehyde. SnoRNA stability was assayed as described previously (Lange et al., 1998; Borovjagin and Gerbi, 1999).

Various U3 snoRNA mutants were created by PCR, using primers from Gibco BRL Life Technologies (Gaithersburg, Md.) containing the T7 promoter sequence at its 5' end (shown below in italics). For one step PCR mutagenesis, or as the final reaction for multi-step PCR, the following "conventional" PCR primer sequences were used:

```
5' (sense) primer:
5' TAA TAC GAC TCA CTA TAG GGA AGA CTA TAC TTT CAG
GGA TCA 3'
(SEQ ID NO: 27)

3' (anti-sense) primer:
5' TAA AAC CAC TCA GCC TGT GTT CTC TCC CTC C 3'.
(SEQ ID NO: 28)
```

The conventional 3' PCR primer used for amplification of the wild type U3 and all the mutants carried 5 extra nucleotides at its 5' end. This resulted in a tail of 5 extra nucleotides at the 3' termini of all the U3 snoRNA transcripts to enhance their stability in oocytes.

The mutations (substitutions are shown in bold, as are insertions to be presented later) in the 5' portion of U3 snoRNA were created by including a mutant sequence as a part of the 5' (sense) PCR primer:

```
5'-ncb:
5' TAA TAC GAC TCA CTA TAG GGA AGA CTA ATG AAA GTC
GGA TC 3'
(SEQ ID NO: 29)

5'-cb:
5' TAA TAC GAC TCA CTA TAG GGA AGA CTT GTC TGA ATT
GGA TC 3'
(SEQ ID NO: 30)
```

The double mutants 5'-ncb/subtag and 5'-cb/subtag were created by using the same 5' mutant primers shown above but with U3 subtag (see below) as the template.

Several U3 snoRNA mutants were made by a two-step procedure. In these cases, the "conventional" 3' primer was used with the following 5' (sense) PCR primers in the first step:

```
4 nt sub/loop I:  5' CAG GGA TCA TTT CTA TAG GTA CAT CCT GGT GAA ATG 3'
                  (SEQ ID NO: 31)

Δ4 nt/loop I:     5' CAG GGA TCA TTT CTA TAG GTC CTG GTG AAA TG 3'
                  (SEQ ID NO: 32)

4 nt ins/loop I:  5' CAG GGA TCA TTT CTA TAG GTT ATG TAT TCC TGG 3'
                  (SEQ ID NO: 33)
```

-continued

```
Topstem-ncb/R:   5' CAG GGA TCA TTT CTA TAG GTT GTA GGA TGT GAA ATG 3'
                 (SEQ ID NO: 34)

Topstem-ncb/L:   5' CAG GGA TCA TTT CTA GTC CTT GTA CCT G 3'
                 (SEQ ID NO: 35)

Topstem-cb:      5' CAG GGA TCA ITT CTA GTC CTT GTA GGA TGT GAA ATG 3'
                 (SEQ ID NO: 36)

Δ (2 + 2):       5' CAG GGA TCA TTT CTA TAG GTT GTA CCT GGA AAT GCT CG 3'
                 (SEQ ID NO: 37)
```

Cloned wild type U3 snoRNA from *Xenopus laevis* (pX1U3A: Savino et al., 1992) was used as the template. For the second step, the PCR products from the first step were used as templates and were extended at their 5' end. The "conventional" primers were used for the second PCR step, but the sequence of the 5' conventional PCR primer had 9 bases added that overlapped the sequence of the 5' primer (see above) used for the first step.

In order to create the U3 5'H/intag-16 mutant a different two-step PCR procedure was used. For the first step, the 5' and 3' "conventional" PCR primers were used individually as the external primers along with internal, partially overlapping primers of opposite polarities to create partially overlapping PCR products comprising the 5' and 3' portions of the U3 snoRNA sequence. The insertion sequence (bold upper case letters) was present in the internal primer sequences and contained a restriction site for EcoRI restriction enzyme (bold italics). The internal PCR primers had the following sequences:

```
sense primer:
5' gga aGA ATT CAG ACA ATG AAC TCA CAA ACC ACG 3'
(SEQ ID NO: 38)

anti-sense primer:
5' aag gGA ATT CAC TTG ACA CTT TCG AGC ACA TTT C 3'
(SEQ ID NO: 39)
```

The lower case bold nucleotides were not present in the final mutation, having been discarded by digestion of both of the PCR products with EcoRI and subsequent sticky-end ligation. This produced a full-size U3 snoRNA with a 16 nt insertion containing the EcoRI restriction site. The ligation mixture was PCR re-amplified by using the "conventional" 5' and 3' primers. A similar strategy was used to create the U3 3'H/intag mutants, using the following internal PCR primers were used in the first step of the procedure for 3'/H/intag-16:

```
sense primer:
5' CTG AAC TCA CAA AAA GTG AAT TCA GAC AAC CAC GAG
GAA G 3'
(SEQ ID NO: 40)

anti-sense primer:
5' TCC TCG TGG GAA TTC ACT TTT TGT GAG TTC AGA C 3'
(SEQ ID NO: 41)
```

Creation of 3'H/intag-10 was the same but used: sense primer: 5' CTG AAC TCA CAA AAA GTG AAT TCC CAC GAG GAA G 3' (SEQ ID NO: 42)

Another two-step procedure was used to create the U3 subtag-16 mutant, with a 16 nt substitution immediately preceding the hinge region (FIG. 2C). The pair of primers for the first step were the 5' "conventional" PCR primer (as the sense primer) and 3' (anti-sense) primer: 5' GAG TTC AGA CAC TGA ATT CAC TTT TTC ACC AGG TAG AAC 3' (SEQ ID NO: 43)

Wild type U3 was used as the template. The product of this first step PCR was restricted with EcoRI (bold italics above) and the 5' fragment after restriction was ligated to the 3' EcoRI fragment of the U3 mutant 5'/intag-16.

The U3 subtag-10 mutant (FIG. 2C) was made by a three-step approach. In the first step, the 3' "conventional" primer was used with the following:
5' (sense) primer: 5' <u>TAT AGG TTG TAC CTG</u> GTG AAA TGT GCT AAT TCA GAC ACT GA 3' (SEQ ID NO: 44)
The resulting PCR product was a 5' truncated U3 with a 10 nucleotide substitution preceding the hinge region, and was used as the template in the second PCR step where the 3' "conventional" primer was used with the following:
5' (sense) primer: 5' CAG GGA TCA TTT C<u>TA TAG GTT GTA CCT G</u> 3' (SEQ ID NO: 45)
There was overlap in the 15 underlined nucleotides between the first and second step.

The product of the second step was used as the template for the third step of PCR, using the "conventional" 5' and 3' primers to create the full length mutant U3, subtag-10.

A similar three-step PCR approach was used to create additional mutants in U3 domain I. For the first step, the 3' conventional primer was used with the following 5' (sense) primers:

```
sub/2 + 2:
5'-TAT AGG TTG TAC CTG CCG AAA TGA CCT CGA-3'
(SEQ ID NO: 46)

ins/2 + 2:
5'-TAT AGG TTG TAC CTG CCG TGA AAT GTG CAC TCG A-3'
(SEQ ID NO: 47)

Midstem-ncb:
5'-TAT AGG TTG TAC CTG GTC TTT ACT GCT CGA AAG-3'
(SEQ ID NO: 48)

no bulge:
5'-TAT AGG TTG TAC CTG TAG AAA TGA TCT CGA-3'
(SEQ ID NO: 49)

Δ 4nt/Bottom:
5'-TAT AGG TTG TAC CTG GTG AAA TGT GCT CGA AA/C
TGA AC-3'
(SEQ ID NO: 50)

5' Wintag-10:
5'-TAT AGG TTG TAC CTG GTG AAA TGT GCT CGA AAG TGT
AAT TCA GAC ACT GAA CTC ACA AA-3'
(SEQ ID NO: 51)

5' H/intag-4:
5'-TAT AGG TTG TAC CTG GTG AAA TGT GCT CGA AAG TGT
GAC ACT GAA C-3'
(SEQ ID NO: 52)
```

The second and third steps of PCR were the same as for creation of subtag-10 described above, utilizing overlap in the underlined nucleotides between first and second step 5' primers. The Tag* mutant was prepared as in Lange et al. (1998).

All the PCR reactions were carried out with 50–100 pmol of each primer and 10 ng of U3: wild type plasmid DNA as template. PCR conditions were as follows: denaturation at 94° C. for 3 min, 5 cycles of 94° C. for 30 sec, 55° C. for 30 sec, 72° C. for 1 min, followed by 35 cycles of 94° C. for 30 sec, 60° C. for 30 sec, 72° C. for 1 min. The PCR fragments were gel purified, ligated into PT7blue-T and sequenced as described previously (Lange et al., 1998). The U3 mutant plasmids were used as PCR templates to produce templates for T7-transcription (as in Lange et al., 1998).

A U3 mutant with a 10 nucleotide substitution at the bottom right of the putative stem (subtag 10: FIG. 2C) was able to restore 18S rRNA production fully (FIG. 4, lanes 7 and 11), indicating that the sequence which had been replaced was unnecessary for U3 function. The U3 mutant subtag-10 prevents potential base-pairing at the base of the putative stem and the results indicate that this base-pairing is not essential for U3 snoRNA function in 18S rRNA processing.

The opposite side of the base of the putative stem, which contains evolutionarily conserved Box A', was also mutated by substitution with two different sequences to prevent potential base-pairing. One of these, 5'-cb, was complementary to subtag-10, whereas the other substitution, 5'-ncb, was not complementary (FIG. 2C). When either of these substitutions was tested alone, the substituted U3 snoRNA was not able to rescue 18S rRNA processing (FIG. 4, lanes 18–19 and 15–16, respectively). Instead, a novel intermediate, 19S pre-rRNA, was found, which extends from a site in the ETS about 200 nt from the 5' end of 18S rRNA to a site in the ITS1 about 100 nt from the 5' end of 5.8S RNA (Borovjagin and Gerbi, manuscript in preparation). Since the subtag-10 substitution on the right side of the base of the putative stem of U3 snoRNA had no effect on 18S rRNA production, these data suggest that it is not the absence of base-pairing but rather the sequence itself on the left side of the putative stem which was important for function in rRNA processing and whose mutation (5'-cb and 5'ncb) led to accumulation of 19S pre-rRNA instead of 18S rRNA. This is the first experimental evidence in any system which implicates the importance of U3 Box A' in rRNA processing.

When the U3 double mutant 5'-ncb/subtag-10, where the base of the putative stem remains open, was injected into U3 depleted oocytes, the outcome was the same as for 5'-ncb or 5'-cb alone: no newly synthesized 18S rRNA appeared and the novel 19S pre-rRNA was present (FIG. 4, lane 6). In contrast, when the U3 double mutant 5'-cb/subtag-10 was tested, neither 18S rRNA nor 19S pre-rRNA was formed (FIG. 4, lanes 13–14). In this case, base-pairing at the bottom of the putative stem of domain I is possible due to the compensatory mutation. Results of dimethyl sulfate chemical modification of U3 mutants (data not shown) confirmed that the base of the putative stem was base-paired (5'-cb/subtag-10 mutant) or open (in the 5'-cb, 5'-ncb, subtag-10 and 5'-ncb/subtag-10 mutants). Taken together, the data from these experiments suggest that base-pairing at the bottom of the putative stem is not important for U3 dependent production of 18S rRNA, for example, no base-pairing in the subtag-10 mutant U3 fully rescues 18S, and that to pair this area is, in fact, deleterious for U3 function because neither 19S nor 18S rRNA are formed by 5'-cb/subtag.

EXAMPLE 3

Base-pairing at the Top of the Putative Stem in Domain I of U3 snoRNA is Unnecessary for rRNA Processing We also inquired whether base-pairing at the top of putative stem of domain I of U3 snoRNA is needed for function in rRNA processing. When either side of the top of the putative stem was mutated to disrupt potential base-pairing (FIG. 2A: Topstem-ncb/L and Topstem-ncb/R), 18S rRNA was still produced (FIG. 5, lanes 3 and 5), although at slightly lower levels (75–80%) than with wild type U3 snoRNA. Thus, a base-paired structure at the top of the putative stem is not essential for U3 function in 18S rRNA processing, nor are the sequences on either side of the putative stem important. The compensatory mutation was created (Topstem-cb) which is a U3 double mutation containing Topstem-ncb/R and Topstem-ncb/L. In this double mutant, the wild type sequences of U3 snoRNA at the top of the putative stem are swapped and base-pairing is still possible. When the double mutant Topstem-cb was injected into U3 depleted oocytes, it also was able to almost completely (80% of wild type U3 rescue) restore 18S rRNA production (FIG. 5, lane 4). Therefore, it appears not to matter whether the top of the putative stem of domain I has the ability to pair or not.

EXAMPLE 4

The 5' Hinge Sequence in the Middle of the Putative Stem of Domain I of U3 snoRNA is Important for 18S rRNA Formation Several lines of evidence indicate that a sequence in the middle (right side) of the putative stem of domain I is important for U3 function in rRNA processing. First, only inefficient rescue of 18S rRNA was seen with the U3 mutant subtag-16 (FIG. 4, lanes 3–4). Since the 10 nt at the 3' end of this substitution were identical to those in subtag-10 that had no adverse effect (FIG. 4, lane 7), it seemed that mutation of the 6 nt at the 5' end of subtag-16 was responsible for impairing U3 snoRNA function. These sequences invade the middle of the putative stem of domain I (FIG. 2C: subtag-16), and the results suggest their importance for U3 function. To investigate this region further, the U3 mutation Midstem-ncb was created in which the right side of the middle of the putative stem of domain I of U3 snoRNA was replaced by another sequence (FIG. 2A). As can be seen in FIG. 5, lanes 14–15, this mutation was very inefficient in the rescue of 18S rRNA processing.

Because sequences on the right side of the middle of the putative stem of domain I are important for rRNA processing (data from subtag-16 and Midstem-ncb mutants) and evolutionarily conserved Box A on the 5' side is essential for viability in yeast (Hughes, 1996; Méreau et al., 1997) and 18S rRNA formation in Xenopus (Borovjagin and Gerbi, manuscript in preparation), we did not create substitutions to disrupt their potential base-pairing, as 18S rRNA production would become impaired by mutation of these functional elements. Instead, we created a mutation to increase the potential for base-pairing in this region. Two pairs of bulged nucleotides occur on both the right and left sides of the putative stem of domain I; the former were mutated to permit their pairing with the latter (FIG. 2B: "no bulge"). This "no bulge" U3 mutant was unable to produce 18S rRNA (FIG. 5, lanes 7–8), suggesting that stabilization of base-pairing in the middle portion of the putative stem of domain I may be deleterious for U3 function. The mutated nucleotides were themselves not critical for U3 function, as 18S rRNA was still produced when another substitution (FIG. 2B: sub/2+2) that did not permit pairing of the putative bulges was tested (FIG. 6, lanes 13–14).

The importance of the sequence in the middle right side of the putative stem led us to examine this region more closely. We noticed that although this sequence is not conserved between different species, it is comparable in location relative to the 5' end of U3 (see U3 snoRNA sequence alignment in FIG. 9 of Samarsky and Fournier, 1998) to the U3 sequence shown to base-pair with the 5' external transcribed spacer (5' ETS, hereafter simply referred to as the ETS) in pre-rRNA from the yeast *Saccharomyces cerevisiae* (Beltame and Tollervey, 1992 and 1995; Beltrame et al., 1994). Sequence analysis revealed that the *Xenopus* U3 snoRNA sequence, which is homologous to the ETS pairing sequence in yeast U3, is also able to base-pair with the ETS (Table I). We name this area of U3 snoRNA the "5' hinge." Further analysis showed that base-pairing potential between the U3 5' hinge and the ETS is phylogenetically conserved in a wide range of organisms.

EXAMPLE 5

The 3' Hinge Region of U3 snoRNA is Essential for 18S rRNA Formation

We next asked if the region previously identified as the "hinge" region renamed here as the "3' hinge", to distinguish it from the 5' hinge, is also important for 18S rRNA production. We tested this by assaying the function of the U3 Tag* mutant where sequences of the U3 3' hinge region are substituted by a foreign sequence (FIG. 2A). As can be seen in FIG. 5, lanes. 17–19, the Tag* mutant was unable to rescue 18S rRNA production. Therefore, we conclude that the sequences normally found in the wild type U3 3' hinge region are essential for 18S rRNA processing. The importance of both the 5' hinge and 3' hinge of U3 snoRNA for 18S rRNA formation may reflect their potential to base-pair with the ETS of pre-rRNA.

EXAMPLE 6

The Spacing Between Functionally Important Cis-Elements in U3 snoRNA is Critical for 18S rRNA Processing We have shown above that sequences in Box A' and the 5' and 3' hinge regions of U3 snoRNA are needed for production of 18S rRNA. If these cis-elements of U3 snoRNA act in concert, then their position relative to one another and to the rest of the molecule should be important. This turned out to be the case. We assayed the function of U3 with insertions or deletions between the cis-elements, and conclude that the spacing between these elements is critical for 18S rRNA production.

A U3 mutant carrying a deletion of 4 nucleotides between the 5' hinge region and Boxes A'+A (FIG. 2C: Δ4 nt/loop I) was unable to restore 18S rRNA formation (FIG. 6, lanes 7–8). The deleted sequences were themselves not critical, as U3 with a substitution of these sequences (FIG. 2C: Δ4 nt sub/loop I) was able to restore 18S rRNA processing (FIG. 6, lanes 3–4). Therefore, decreasing the distance between the 5' hinge region and Boxes A'+A appears to be deleterious for 18S rRNA processing. In contrast, alteration of this distance by a 4 nucleotide insertion (FIG. 2B: 4 nt ins/loop I) can be tolerated, as some 18S rRNA was formed (FIG. 6, lanes 5–6).

Next, mutations were tested that change the spacing at both ends of the 5' hinge region. The U3 mutant Δ(2+2) (FIG. 2B), where both two nucleotide bulges nucleotides on the right side of the putative stem of U3 domain I had been deleted, was unable to rescue 18S rRNA processing (FIG. 6, lanes 15–16). In contrast, the U3 mutant ins/2+2 (FIG. 2B) that had an insertion of two nucleotides in each of the two bulges allowed some 18S rRNA to be made (FIG. 6, lanes 11–12). As stated above, the sequence identity of the bulged nucleotides is not important for U3 function in 18S rRNA processing (FIG. 6, lanes 13–14: sub/2+2).

Mutations involving deletion or insertion between the 5' hinge and 3' hinge of U3 snoRNA were deleterious, indicating that the distance between the 5' end of U3 snoRNA (including Boxes A'+A and the 5' hinge region) and the 3' hinge is important for 18S rRNA processing. Specifically, no 18S rRNA was produced (FIG. 6, lanes 18–19) when 4 nucleotides in this area were deleted (FIG. 2B: Δ4 nt/Bottom), even though sequence substitution in this region of U3 allowed normal levels of 18S rRNA to be made, as discussed above (FIG. 4, lane 7: subtag-10). Also, U3 mutants with insertions of 16 or 10 nucleotides in this location (FIG. 2A: 5'H/intag-16 and 5'H/intag-10) were unable to function in 18S rRNA processing (FIG. 7, lanes 3–4 and 7–8), and only inefficient processing occurred (FIG. 7: lanes 12–13) with a U3 mutant carrying a 4 nucleotide insertion here (FIG. 2A: 5'H/intag-4).

Similarly, 18S rRNA formation was obliterated or inefficient (FIG. 7, lanes 15–16 and 19–20) after oocyte injection of U3 mutants with a 16 or 10 nucleotide insertion immediately downstream of the 3' hinge (FIG. 2A: 3'H/intag-16 and 3'H/intag-10). These two insertions alter the spacing between the 5' portion of the U3 molecule and domain II, which contains the nucleolar localization elements of *Xenopus* U3 snoRNA (Lange et al., 1998; Narayanan et al., 1999).

EXAMPLE 7

Analysis of Antibiotic Effect of Antisense Oligonucleotides Against a Pathogen *Trypanosoma brucei*

$^{32}$P-labeled and capped, synthetic T7 polymerase transcript of Trypanosome U3 snoRNA produced from the pGB.2 Trypanosome U3 plasmid (Hartshorne and Agabian, Mol. Cell. Biol. 13: 144–154, 1993) is injected into *Xenopus* oocytes in two parallel reactions, one with and one without antisense oligonucleotides which are complementary to the *Trypanosoma brucei* U3 snoRNA 5' and 3' hinge regions. After incubation for few hours, for example about 2–15 hours, or until U3 snoRNA is destroyed, the nuclear RNA is isolated and separated electrophoretically on an acrylamide gel. The size of U3 snoRNA is determined by detecting the radioactive fragment on the gel. The effect of the antisense oligonucleotides can be determined by comparing the fragment from the reaction without antisense oligonucleotides that shows the full length or normal in size. The antibiotic effect of the antisense oligonucleotide treated samples show shorter than full-length RNA product. This shows that the antisense oligonucleotide which is the putative antibiotic agent, can work against its target U3.

Tagged *Xenopus* rDNA where sequences in the ETS have been replaced with sequences complementary to the *Trypanosoma brucei* U3 snoRNA 5' and 3' hinge regions is injected into a *Xenopus* oocyte. When the tagged rDNA is injected and transcribed by the oocyte the 40S pre-rRNA will not be processed because endogenous U3 snoRNA cannot dock on it. The pre-rRNA will only be processed into 20S pre-rRNA and 18S rRNA in the presence of the Trypanosome U3 plasmid. Alternatively, one may use a *Xenopus* U3 plasmid in which 5' and 3' hinge regions have been replaced with the corresponding Trypanosome U3 5' and 3' hinge region sequences. The nuclear RNA is isolated about 18 hours later and run on a denaturing agarose gel. The RNA is transferred to a filter for a Northern blot hybridization analysis using a labeled probe which is complementary to the 18S tag and allows detection of 40S, 20S and 18S species.

The above described reaction is performed in parallel in the presence of the antisense oligonucleotide targeted against the *Trypanosoma brucei* 5' and 3' hinge regions described above and the blocking effect of the antisense oligonucleotide for the production of the tagged 18S rRNA can be seen in the Northern blot hybridization as a diminished or totally absent fragment identified by the probe.

A recombinant *Trypanosoma brucei* U3 snoRNA including the 5' and 3' hinge regions was prepared by in vitro transcription using T7 RNA polymerase (Ambion Megashortscript kit, Austin, Tex.) according to the manufactrer's protocol. The nucleotide concentration was 7.5 mM, except for dGTP which was added in 1 mM concentration. A 4 mM sample of cap analog $^7$mGpppG (Ambion, Austin, Tex.) was included into the transcription mixture so that the resulting T7 transcripts carried a 5' cap. The template for T7 transcription was a PCR product made from the pGB.2 Trypanosome U3 plasmid (Hartshorne and Agabian, Mol. Cell. Biol. 13: 144–154, 1993). After transcription, the samples were treated with about 50 Units/ml DNase I (Ambion, Austin, Tex.) to destroy the template DNA. The RNA was extracted with phenol-chloroform extraction and unincorporated nucleotide were separated using a Sephadex G-25 column (Amersham Pharmacia Biotech, Piscataway, N.J.). The RNA was precipitated in ethanol and washer twice with 70% ethanol before it was used for oocyte injections.

The *Xenopus* oocytes were prepared and the endogenous snoRNA depleted as described in Borovjagin and Gerbi (1999). About 0.1–2 ng/nl of the capped recombinant *Trypanosoma brucei* U3 snoRNAs were injected into *Xenopus* oocytes using a single nuclear injection about 4 hours after depletion.

EXAMPLE 8

Preparation of Antisense Oligonucleotides Against *Trypanosoma brucei* 5' and 3' Hinge Regions and use of Such Antisense Oligonucleotides A mixture of antisense oligonucleotides were designed to include complementary sequences to *Trypanosoma brucei* U3 snoRNA 5' hinge (5'-ATTTAA-3') (SEQ ID NO: 53) and 3' hinge regions (5'-TGTTGGTTGTGT-3') (SEQ ID NO: 54). These antisense oligonucleotides were used as a candidate antibiotic agent. The antisense oligonucleotides were mixed with the *Xenopus* oocytes injected with the capped RNA comprising the *Trypanosoma brucei* 5' and 3' hinge regions. The concentration of the antisense oligonucleotides was about 1–10 ng/nl and the injections of about 8–10 nl were made into oocytes using 1–10 sequential injections.

After approximately 10–20 hours of incubation the oocytes were isolated in 75 mM KCl, 70 mM MgCl$_2$, 20 mM Tris-HCl (pH 7.5), 2 mM dithiotreitol, 0.1 mM EDTA, 2% (w/v) polyvinylpyrrolidone. Total nuclear RNA was extracted from 5–10 oocytes by the Rapid Total RNA Isolation kit (5 Prime-3 Prime, Boulder, Colo.) according to the manufacturer's instructions. For analysis of in vivo-labeled rRNA, an equal number of counts/minute (cpm) from different samples was loaded in each lane. The RNA was separated by gel electrophoresis in acrylamide gels to detect the Trypanosome U3 snoRNA which is present when the antisense oligonucleotide is not added, but will be shorter than its wild type form or completely absent after injection of the antisense oligonucleotide. RNA was analyzed with a Fuji X phosphorimager using BAS1000 MacBas software. Alternatively, the radioactively labeled rRNA can be detected by x-ray film and consequently quantified by a densitometer. Also, a Northern blot hybridization can be performed with labeled probe against the pre-rRNAs.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

---

What is claimed is:

1. A method of screening for an antibiotic agent comprising the steps of
   (a) providing a mixture of a first recombinant RNA comprising 5' and 3' hinge regions of domain I of U3 snoRNA and a second recombinant RNA comprising pre-rRNA under conditions that allow binding of said first and second recombinant RNAs; and
   (b) contacting said mixture with a candidate antibiotic agent under conditions which permit inhibition of said binding wherein inhibition of said binding is indicative of an antibiotic agent.

2. A method of screening for an antibiotic agent comprising the steps of
   (a) providing in a living cell a mixture of a first recombinant RNA comprising 5' and 3' hinge regions of domain I of U3 snoRNA and a second recombinant RNA comprising pre-rRNA under conditions that allow processing of said second recombinant ribonucleic acid; and
   (b) contacting said cell with a candidate antibiotic agent under conditions which permit inhibition of processing of said second recombinant RNA wherein said inhibition of processing is indicative of the antibiotic agent.

3. The method of claim 2 wherein the cell is an eukaryotic cell.

4. The method of claim 2 wherein the cell grows as a single cell.

5. The method of claim 2 wherein the cell is a yeast cell.

6. The method of claim 2 wherein the cell is a *Xenopus* oocyte.

7. A method of screening for an antibiotic agent comprising the steps of
   (a) providing in a living cell a mixture of a first recombinant RNA comprising 3' and 5' hinge regions of domain I of U3 snoRNA and a second recombinant RNA comprising pre-rRNA under conditions that allow ribosome synthesis; and
   (b) contacting said cell with a candidate antibiotic agent under conditions which permit inhibition of said ribosome synthesis wherein said inhibition of ribosome synthesis is indicative of the antibiotic agent.

8. The method of claim 7 wherein the cell is an eukaryotic cell.

9. The method of claim 7 wherein the cell grows as a single cell.

10. The method of claim 7 wherein the cell is a yeast cell.

11. The method of claim 7 wherein the cell is a *Xenopus* oocyte.

12. A method of screening for an antibiotic agent comprising the steps of
   (a) providing in a living cell a mixture of a first recombinant RNA comprising 5' and 3' hinge regions of domain I of U3 snoRNA and a second recombinant RNA comprising pre-rRNA under conditions that allow protein synthesis; and
   (b) contacting said cell with a candidate antibiotic agent under conditions which permit inhibition of protein synthesis wherein said inhibition of protein synthesis is indicative of the antibiotic agent.

13. The method of claim 12 wherein the cell is an eukaryotic cell.

14. The method of claim 12 wherein the cell grows as a single cell.

15. The method of claim 12 wherein the cell is a yeast cell.

16. A method of screening for an antibiotic agent comprising the steps of
   (a) providing in a living cell a mixture of a first recombinant RNA comprising 5' and 3' hinge regions of domain I of U3 snoRNA and a second recombinant RNA comprising pre-rRNA under conditions that allow growth of said cell; and
   (b) contacting said cell with a candidate antibiotic agent under conditions which permit inhibition of growth of said cell wherein said inhibition of inhibition of growth is indicative of the antibiotic agent.

17. The method of claim 16 wherein the cell, is an eukaryotic cell.

18. The method of claim 16 wherein the cell grows as a single cell.

19. The method of claim 16 wherein the cell is a yeast cell.

20. A method of screening for an antibiotic agent comprising the steps of
   (a) providing in a living cell a mixture of a first recombinant RNA comprising 5' and 3' hinge regions of domain I of U3 snoRNA and a second recombinant RNA comprising pre-rRNA under conditions that allow division of said cell and thereby increase in the cell number; and
   (b) contacting said cell with a candidate antibiotic agent under conditions which permit inhibition of said cell division wherein said inhibition of cell division is indicative of the antibiotic agent.

21. The method of claim 20 wherein the cell is an eukaryotic cell.

22. The method of claim 20 wherein the cell grows as a single cell.

23. The method of claim 20 wherein the cell is a yeast cell.

24. A method of screening for an antibiotic agent comprising the steps of
   (a) providing in a living cell a mixture of a first recombinant RNA comprising 5' and 3' hinge regions of domain I of U3 snoRNA and a second recombinant RNA comprising pre-rRNA under conditions that allow said cell to live; and
   (b) contacting said cell with a candidate antibiotic agent under conditions which permit inhibition of cell viability wherein said inhibition of cell viability is indicative of the antibiotic agent.

25. The method of claim 24 wherein the cell is an eukaryotic cell.

26. The method of claim 24 wherein the cell grows as a single cell.

27. The method of claim 24 wherein the cell is a yeast cell.

* * * * *

UNITED STATES PATENT AND TRADEMARK OFFICE
CERTIFICATE OF CORRECTION

PATENT NO. : 6,913,889 B2
DATED : July 5, 2005
INVENTOR(S) : Gerbi et al.

It is certified that error appears in the above-identified patent and that said Letters Patent is hereby corrected as shown below:

<u>Column 1,</u>
Line 12, add the following paragraph:
-- This invention was made with government support from NIH under grant/ contract no. GM20261. The United States Government has certain rights in this invention. --.

Signed and Sealed this

Sixth Day of September, 2005

JON W. DUDAS
*Director of the United States Patent and Trademark Office*